US008912535B2

(12) United States Patent
Polander et al.

(10) Patent No.: US 8,912,535 B2
(45) Date of Patent: Dec. 16, 2014

(54) NAPHTHALENE-DIIMIDE-HETEROCYCLE-NAPHTHALENE DIIMIDE OLIGOMERS AS ORGANIC SEMICONDUCTORS AND TRANSISTORS THEREFROM

(71) Applicant: Georgia Tech Research Corporation, Atlanta, GA (US)

(72) Inventors: Lauren E. Polander, Atlanta, GA (US); Shree Prakash Tiwari, Atlanta, GA (US); Seth Marder, Atlanta, GA (US); Bernard Kippelen, Decatur, GA (US); Raghunath R. Dasari, Atlanta, GA (US); Yulia A. Getmanenko, Atlanta, GA (US); Do Kyung Hwang, Duluth, GA (US); Mathieu Fenoll, Atlanta, GA (US)

(73) Assignee: Georgia Tech Research Corporation, Atlanta, GA (US)

(*) Notice: Subject to any disclaimer, the term of this patent is extended or adjusted under 35 U.S.C. 154(b) by 0 days.

(21) Appl. No.: 13/942,642

(22) Filed: Jul. 15, 2013

(65) Prior Publication Data
US 2014/0021448 A1 Jan. 23, 2014

Related U.S. Application Data

(63) Continuation-in-part of application No. PCT/US2012/033590, filed on Apr. 13, 2012.

(51) Int. Cl.
*H01L 21/44* (2006.01)
*H01L 51/00* (2006.01)

(52) U.S. Cl.
CPC ........ *H01L 51/0072* (2013.01); *H01L 51/0067* (2013.01); *H01L 51/0074* (2013.01); *H01L 51/0068* (2013.01); *H01L 51/0071* (2013.01)
USPC .............. 257/40; 257/E51.006; 257/E51.024; 438/99; 438/149; 438/151

(58) Field of Classification Search
CPC ........................................ H01L 51/067–51/072
USPC ........ 257/40, E51.006, 24; 438/99, 149–151, 438/161
See application file for complete search history.

(56) References Cited

U.S. PATENT DOCUMENTS

| 8,530,270 B2 * | 9/2013 | Shukla et al. .................... 438/99 |
| 2011/0291076 A1 * | 12/2011 | Shukla et al. .................... 257/40 |
| 2011/0294257 A1 * | 12/2011 | Shukla et al. .................... 438/99 |
| 2014/0042369 A1 * | 2/2014 | Huang et al. .................. 252/500 |

* cited by examiner

*Primary Examiner* — Michael Lebentritt
(74) *Attorney, Agent, or Firm* — Foley & Lardner LLP

(57) ABSTRACT

The various inventions and/or their embodiments disclosed herein relate to certain naphthalene diimide (NDI) compounds wherein the NDI groups are bonded to certain subclasses of bridging heteroaryl (hAr) groups, such as the "NDI-hAr-NDI" oligomeric compounds, wherein hAr is a heteroaryl group chosen to provide desirable electronic and steric properties, and the possible identities of the "$R^z$" terminal peripheral substituent groups are described herein. Transistor and inverter devices can be prepared.

17 Claims, 57 Drawing Sheets

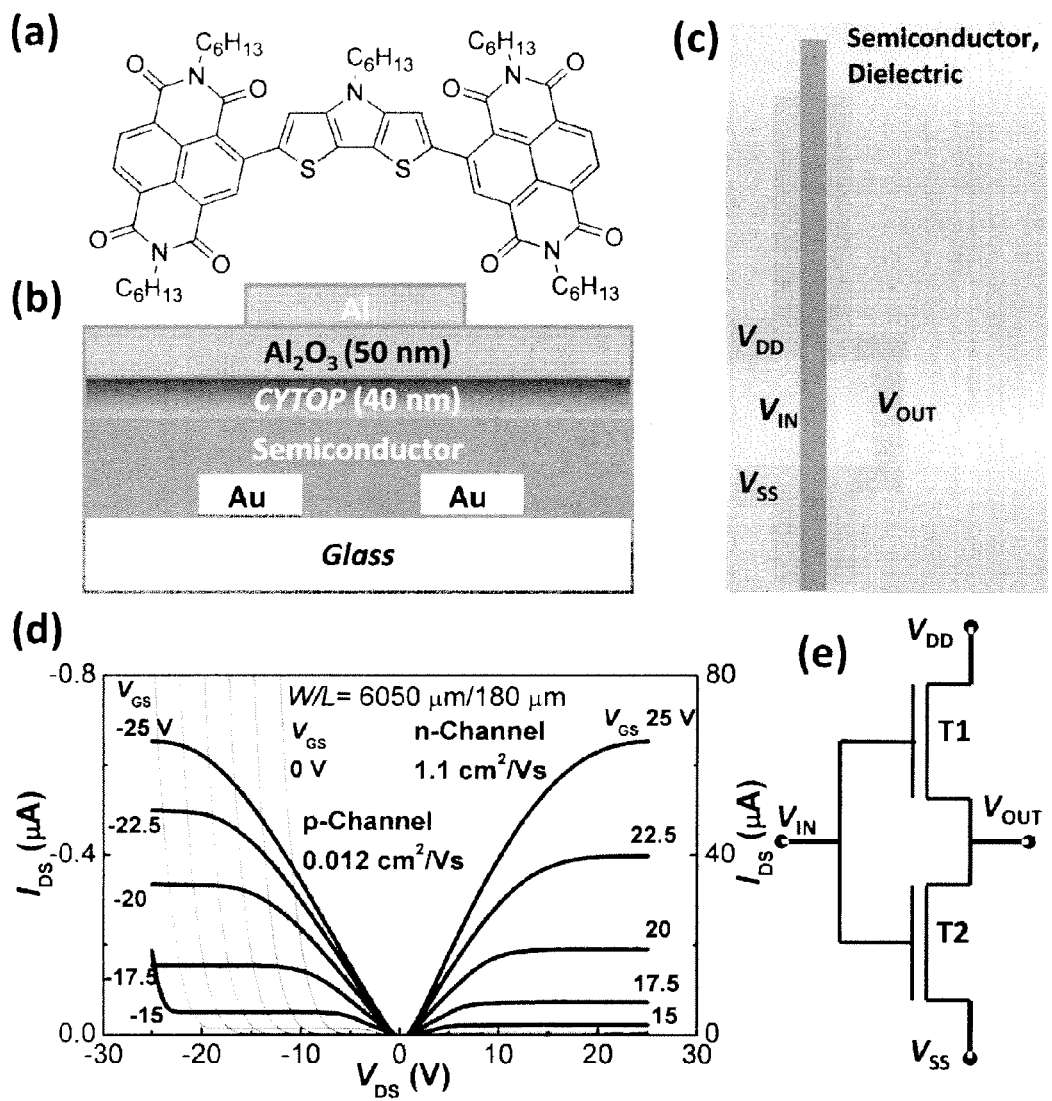
Figures 10a-e

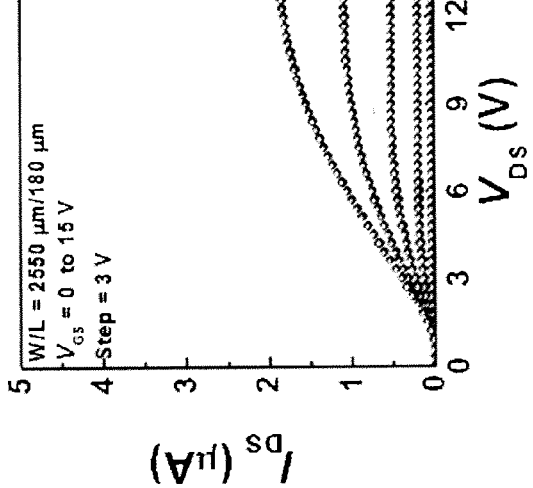
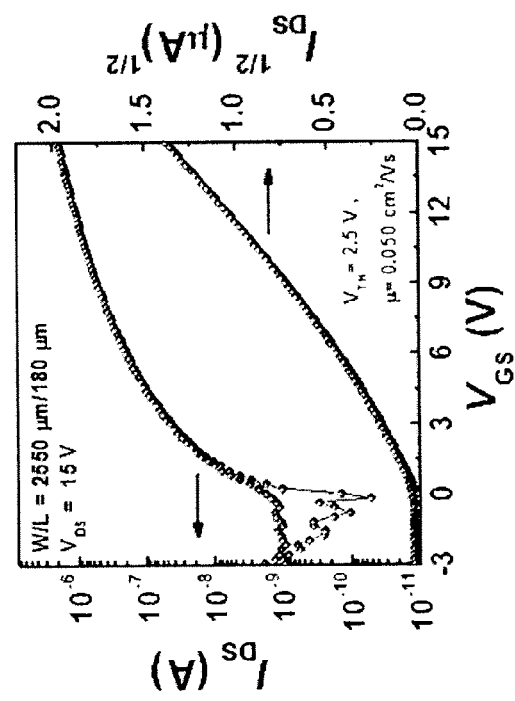
Figure 14

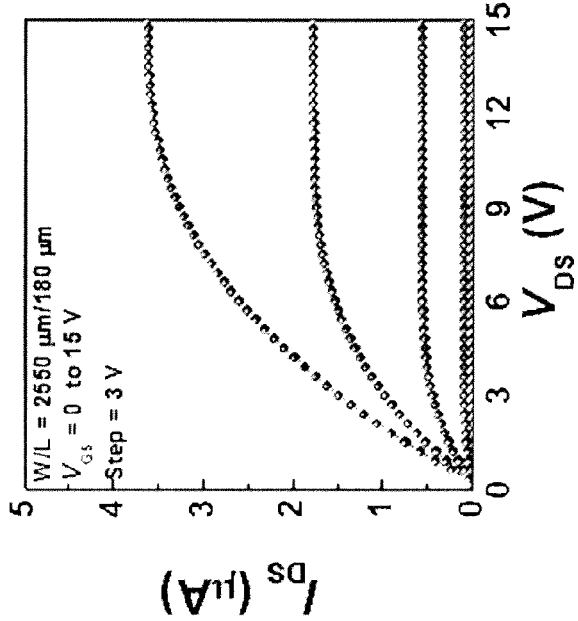
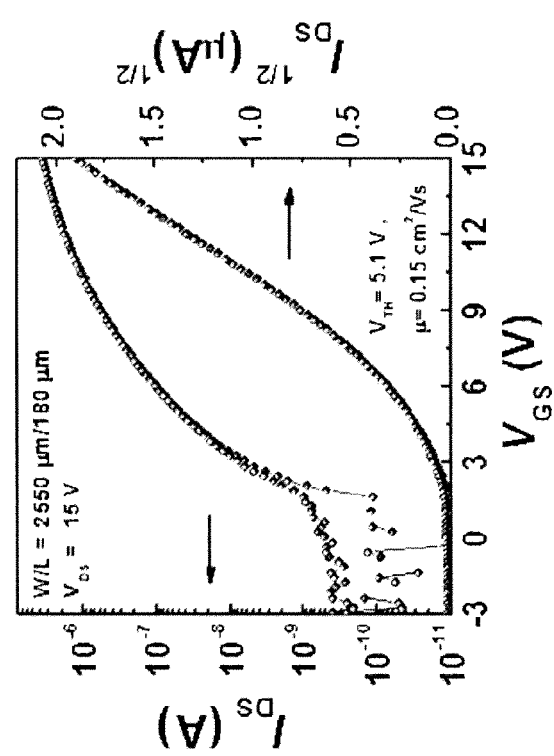
Figure 15

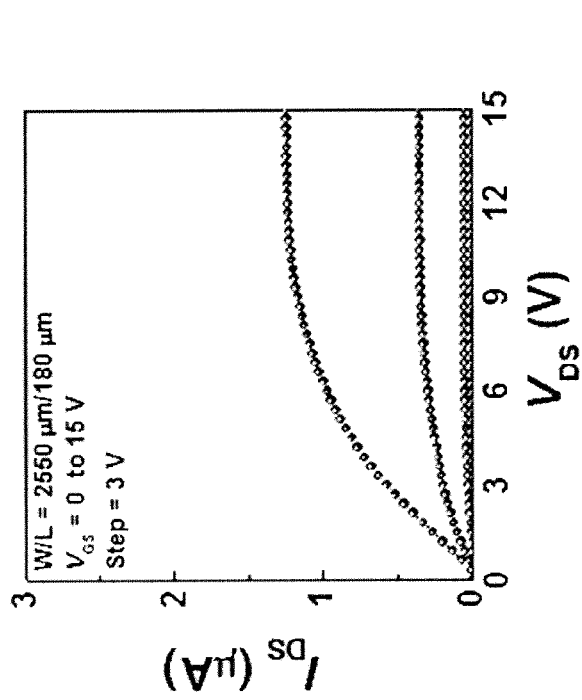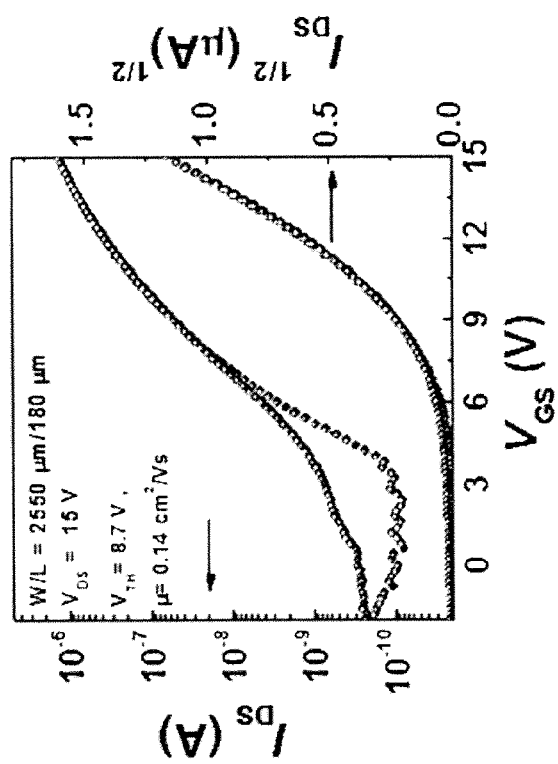
Figure 16

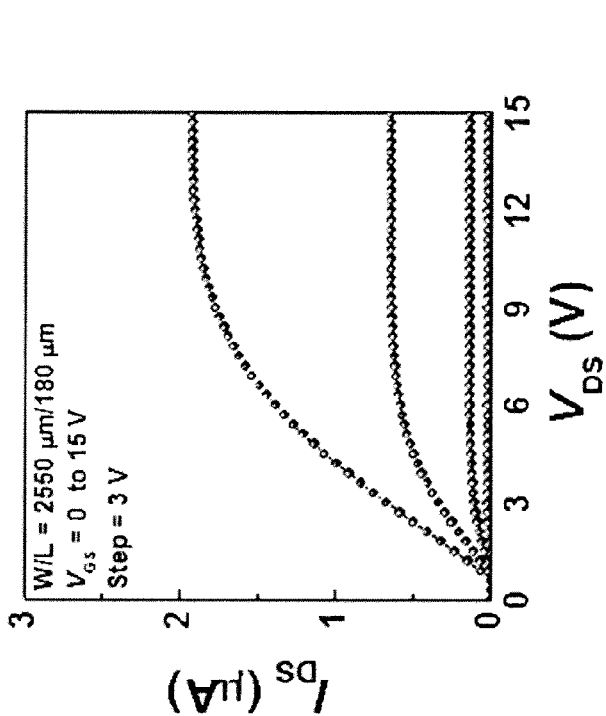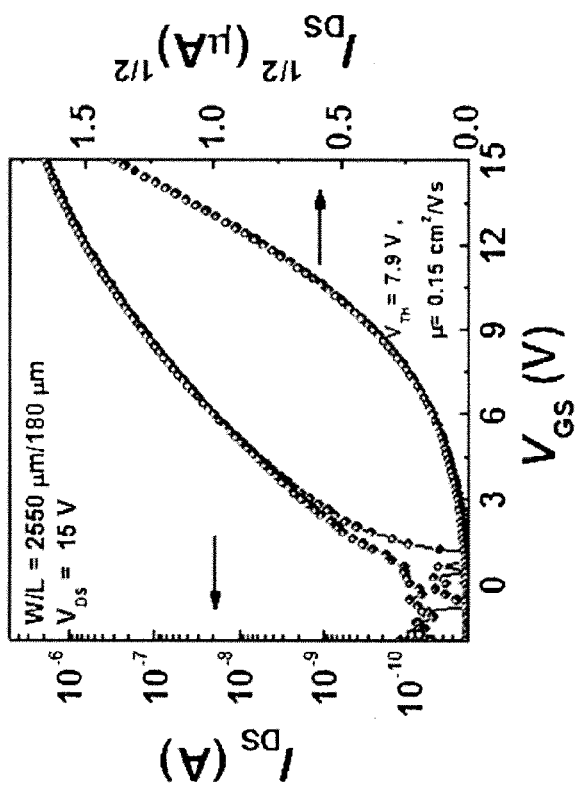
Figure 17

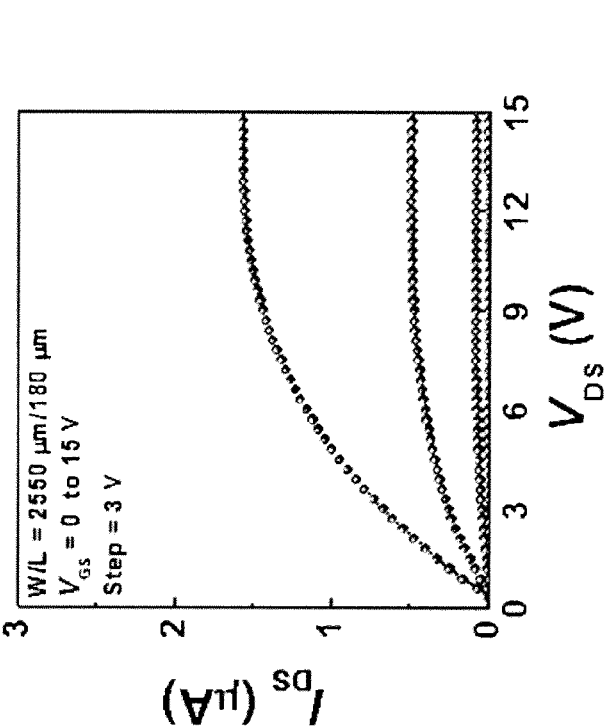
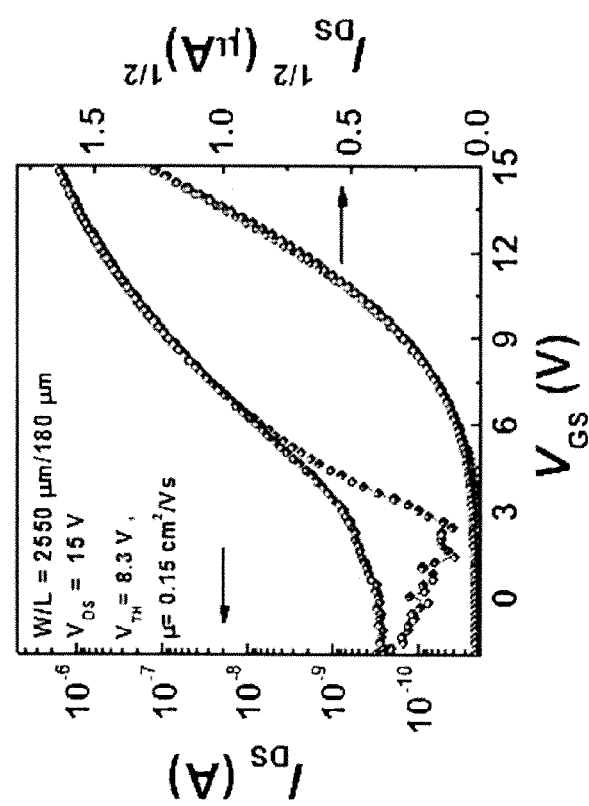
Figure 18

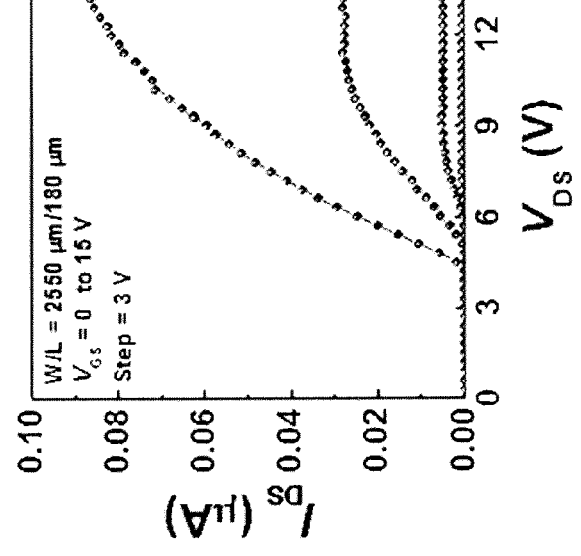
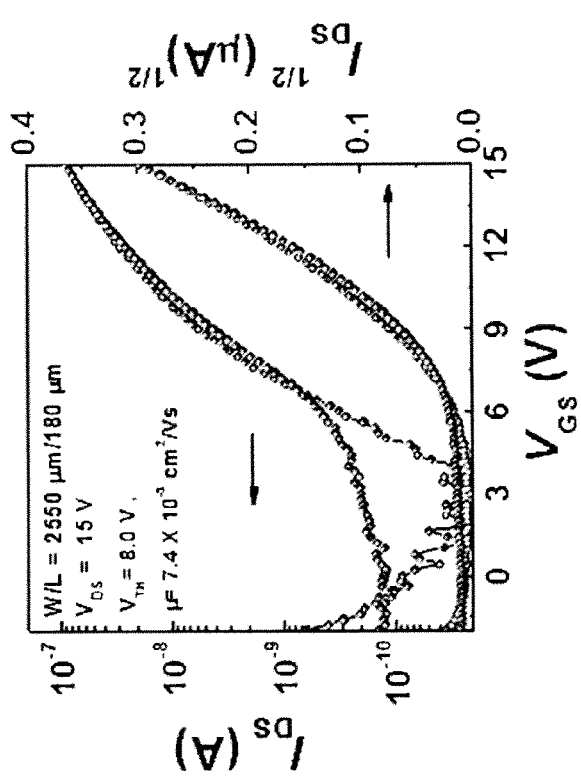
Figure 19

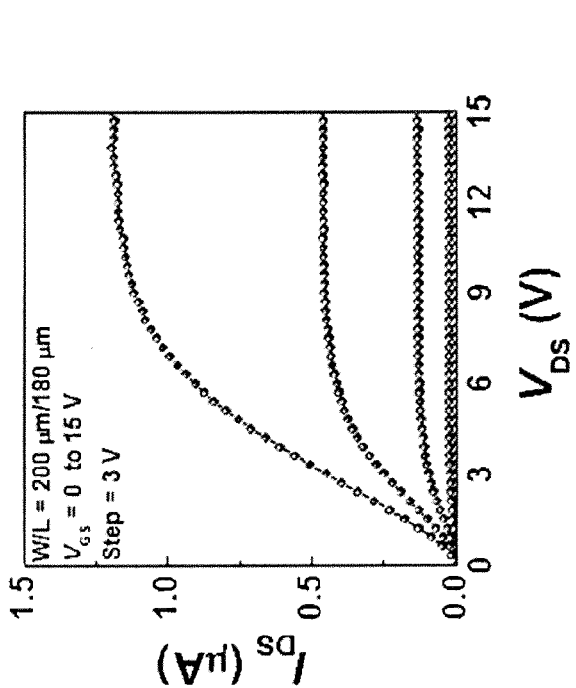
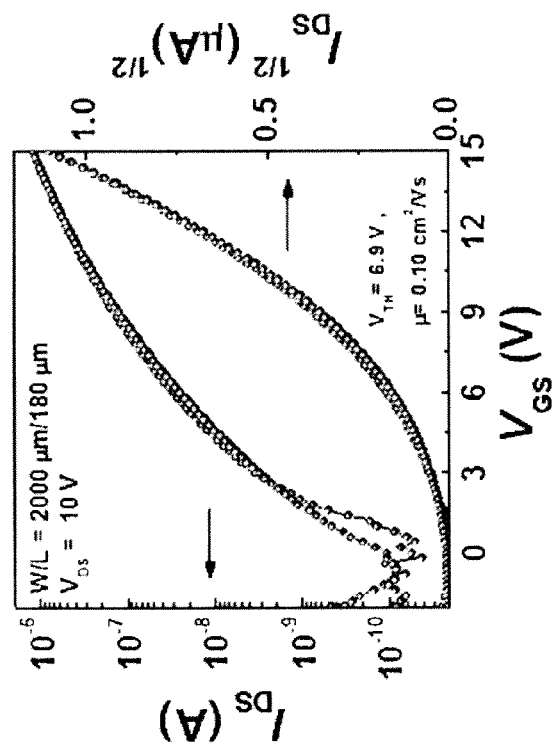
Figure 22

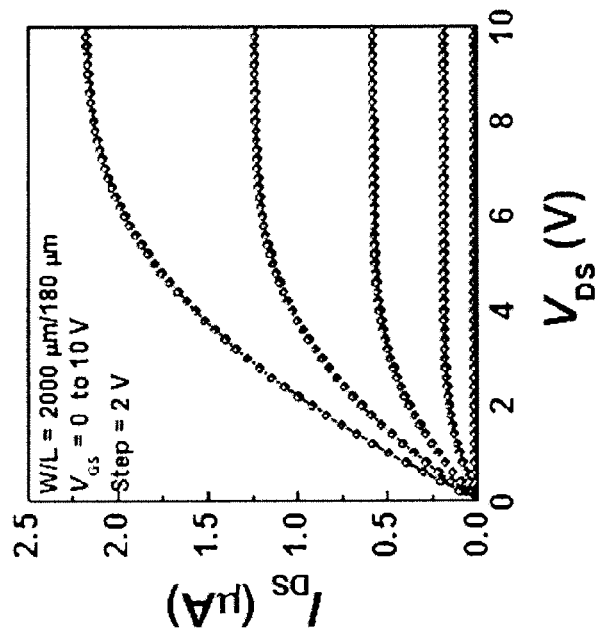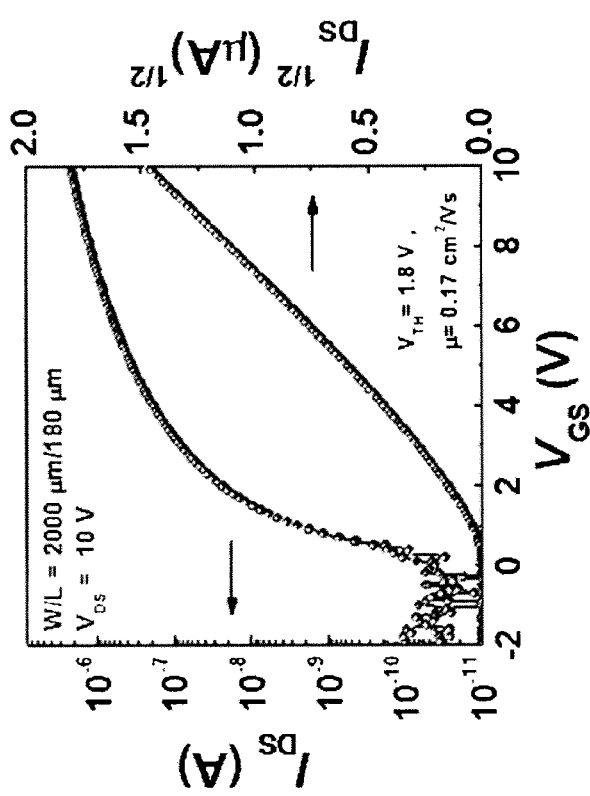
Figure 24

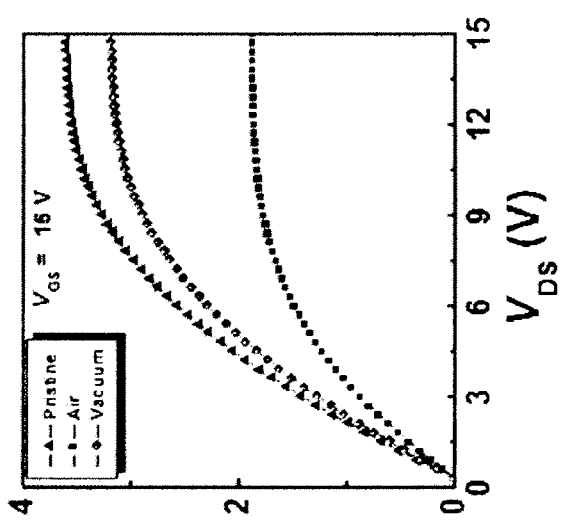
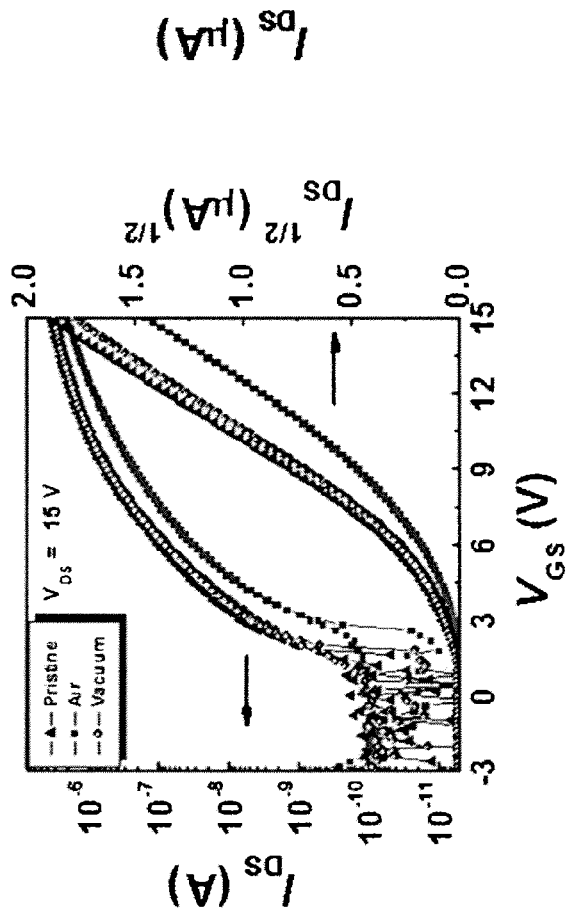
Figure 27

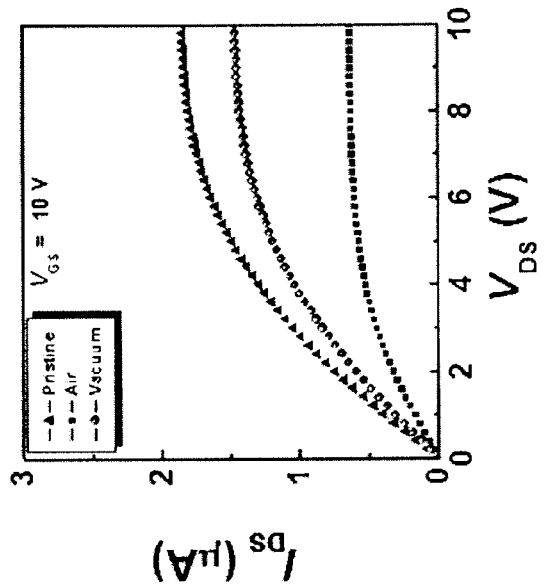
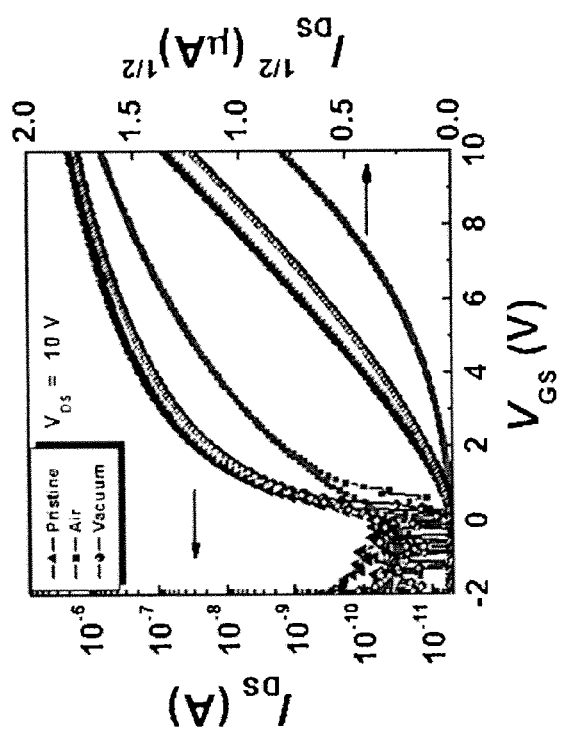
| Exposure condition | $C_{in}$ (nF/cm²) at 1kHz | $\mu$ (cm²/Vs) | $V_{TH}$ (V) |
|---|---|---|---|
| Pristine | 35.2 | 0.14 ± 0.02 | 1.7 ± 0.3 |
| Air | 35.2 | 0.09 ± 0.03 | 4.5 ± 0.7 |
| Vacuum | 35.2 | 0.12 ± 0.02 | 2.6 ± 0.2 |
Figure 30

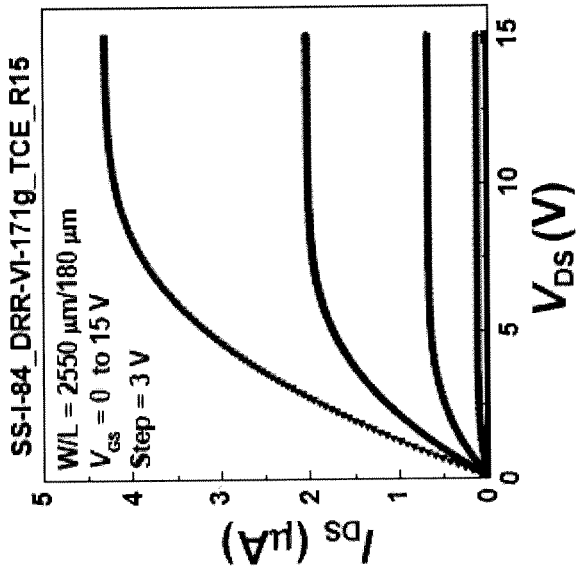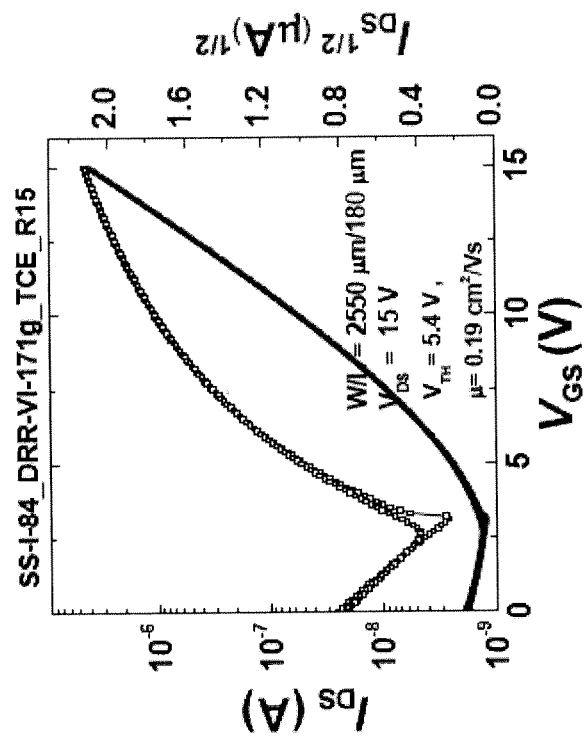
Figure 32a

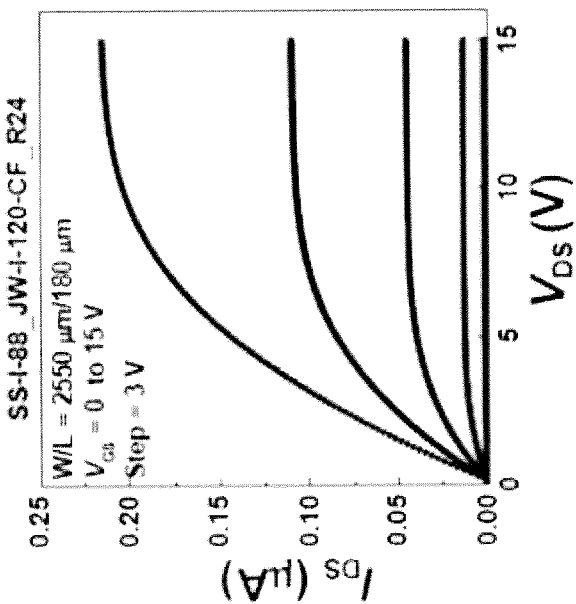
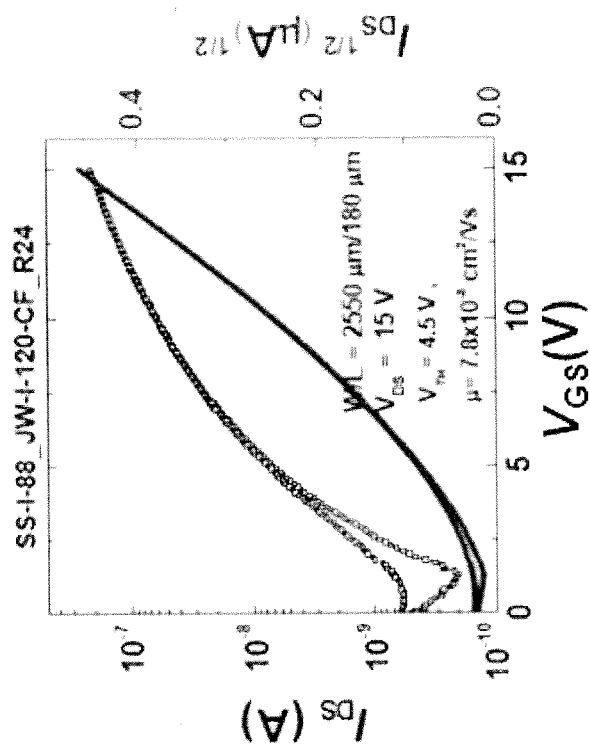
Figure 32b

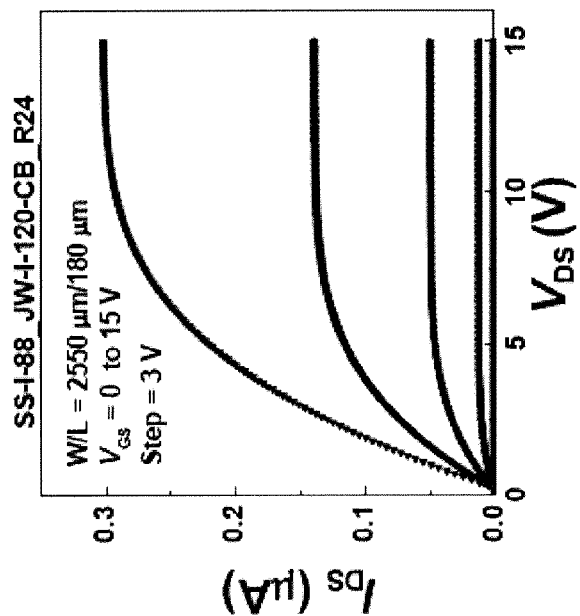
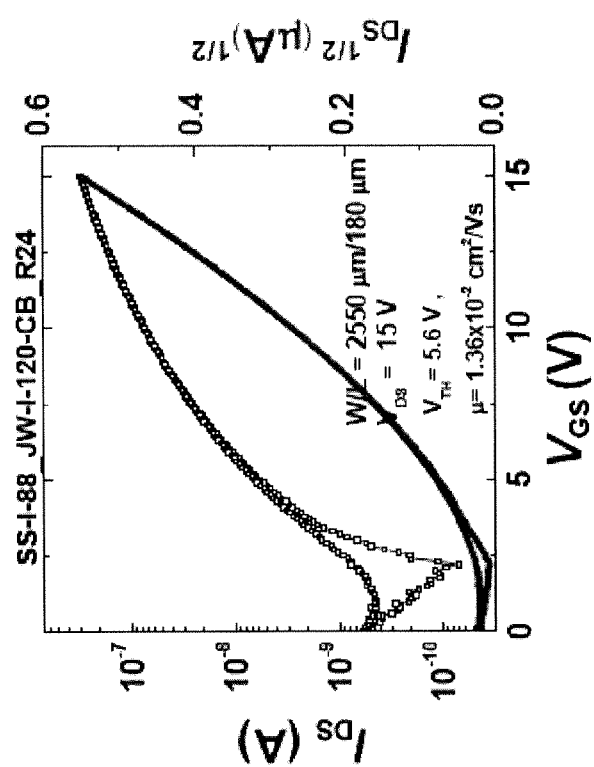
Figure 32c

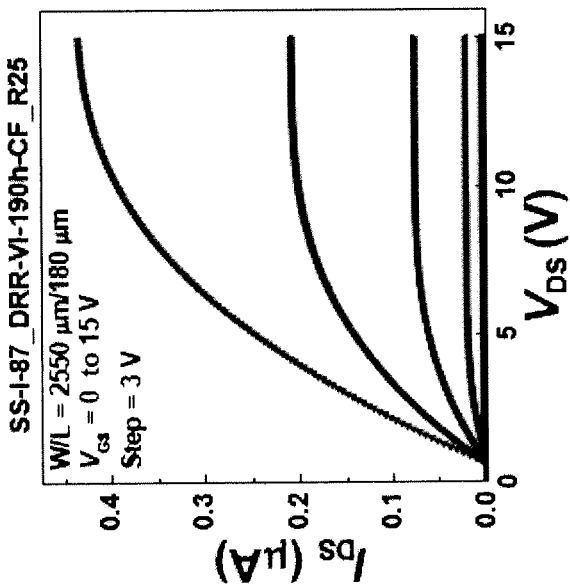
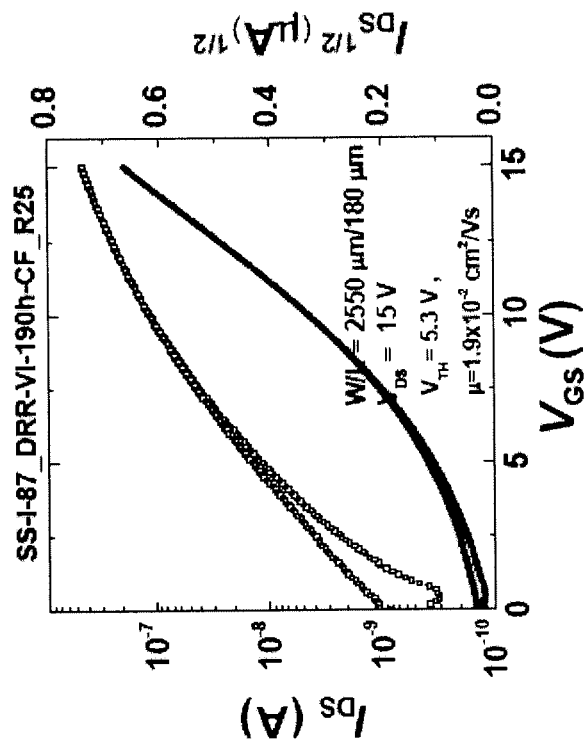
Figure 33a

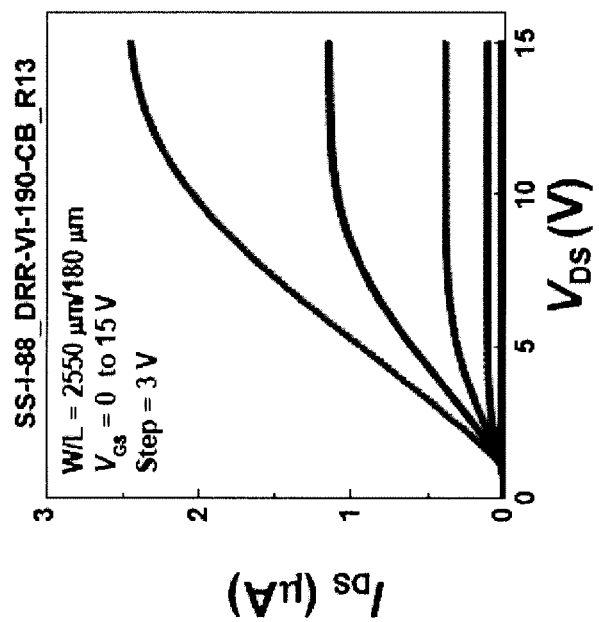
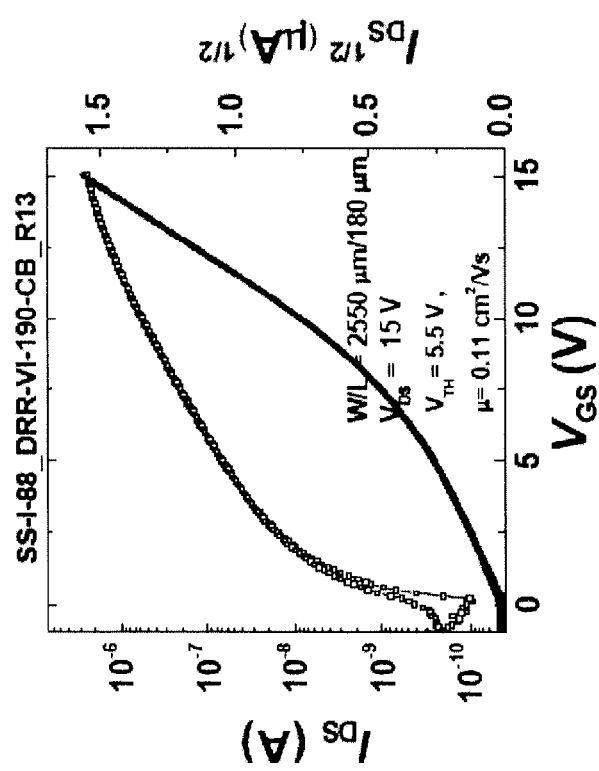
Figure 33b

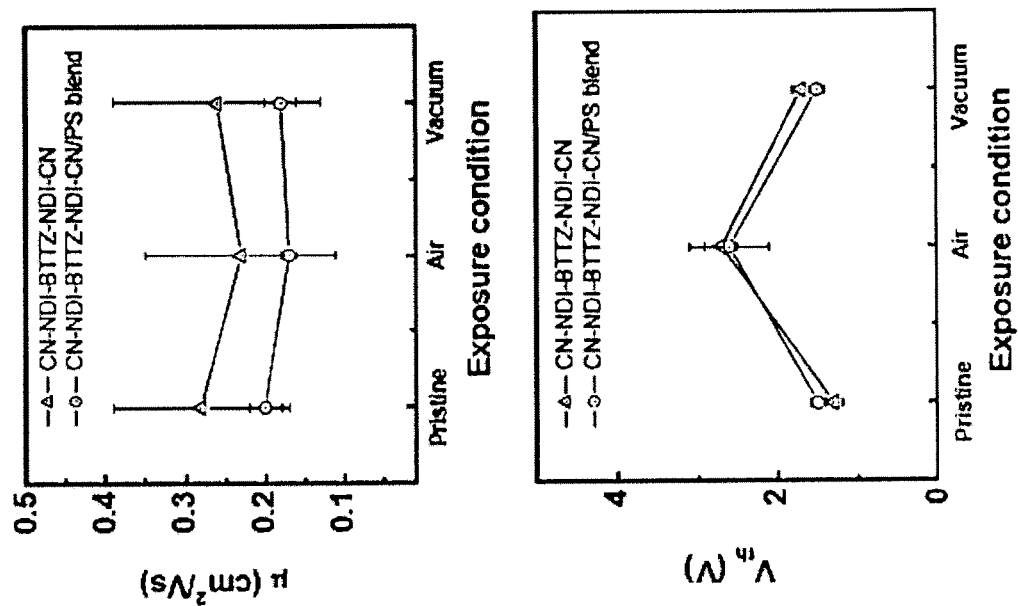
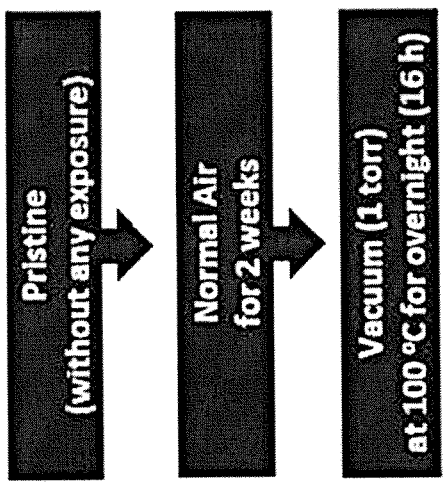
Figure 37

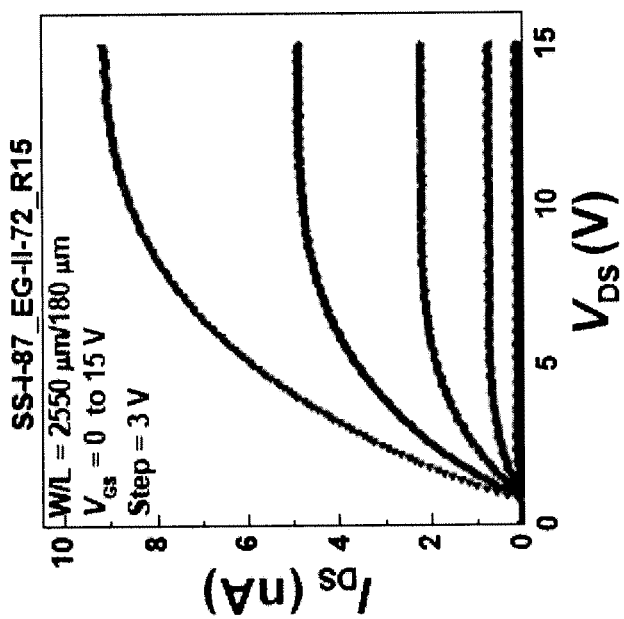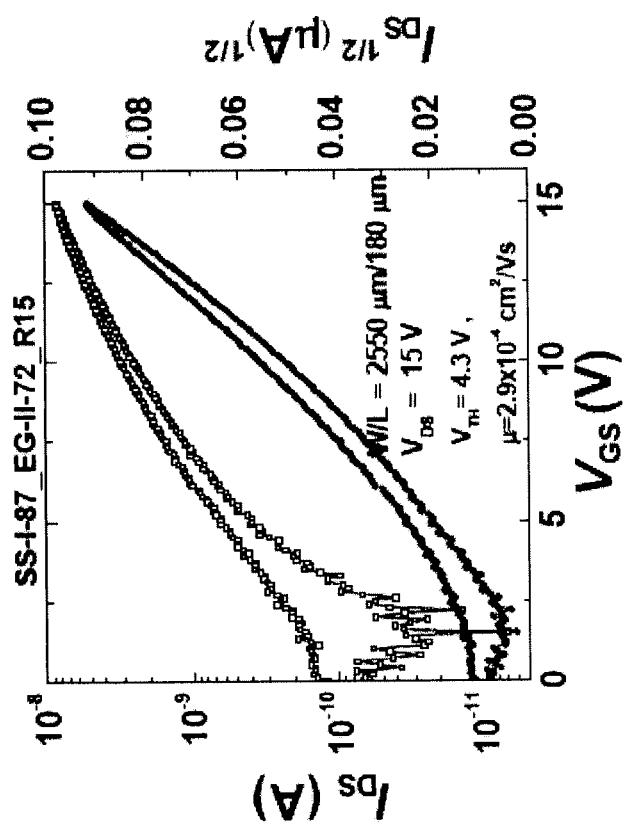
Figure 39a

NAPHTHALENE-DIIMIDE-HETEROCYCLE-NAPHTHALENE DIIMIDE OLIGOMERS AS ORGANIC SEMICONDUCTORS AND TRANSISTORS THEREFROM

CROSS REFERENCE TO RELATED APPLICATIONS

This application is a Continuation-In-Part of International Application No. PCT/US2012/033590, filed Apr. 13, 2012, the contents of which is hereby incorporated by reference in its entirety.

TECHNICAL FIELD OF THE INVENTION

The inventions disclosed and described herein relate to oligomers comprising a combination of naphthalene diimide-heterocycle-naphthalene diimide groups, and their synthesis and uses as organic semiconductors in organic electronic devices such as transistors.

BACKGROUND OF THE INVENTION

Organic semiconductors have attracted attention in the art due to their potential applications in making large area, flexible, and low-cost electronic devices, including organic light-emitting diodes (OLEDs), solar cells and/or transistors. Such organic semiconductors can be relatively low molecular weight "small molecules" that can be vapor deposited. Alternatively, semiconducting organic oligomers or polymers can be solution processed to form organic semiconductor films at the low costs necessary to enable many new and desirable end use applications. See for example a review article by Shirota and Kageyama (Chem. Rev. 2007, 107, 953-1010).

While quite a number of organic semiconductor small molecules, oligomers, and/or polymers have been reported in the prior art that can transport holes reasonably efficiently, the identification, synthesis, and uses of organic semiconductor compounds that can efficiently transport electrons, especially in the presence of air and/or water, has proven much more difficult, especially if solution processability is also desired.

Among the best examples of electron transporting compounds from the prior art that are vapor processable are monomeric "small molecule" naphthalenediimide ("NDI") and perylenediimide ("PDI") compounds having the structures shown below;

It is known that measured "field-effect" electron mobility values, current on/off ratios, and threshold voltages measured from organic field effect transistors "OFETs" cannot be considered representative of the intrinsic mobility values of a given material, but rather are a measure of their ability to function in a given device configuration that can vary very significantly with the selection of electrode, dielectric, the channel width, the channel length, the mode of deposition, the processes of post-deposition treatment such as but not limited to thermal annealing, and other transistor device structure details used in such OFET devices, as well as the specific compatibility and suitability of the selection of the other components of such OFETs with the physical and electronic properties of each organic semiconductor. Nevertheless, Table 1 below summarizes the best prior art results known to Applicants for vapor deposited "small molecule" OFETs in specific device configurations.

TABLE 1

OFET device data for select rylene diimide small molecules (vacuum deposited).

| Operation | Field Effect Mobility $\mu_e$ (cm$^2$V$^{-1}$s$^{-1}$) | $I_{ON}/I_{OFF}$ | $V_T$ (V) | Device structure |
|---|---|---|---|---|
| 1a | Vac. | 0.16 | | | TC gold on Si/SiO$_2$ |
| | Air | | 10$^{-6}$ | | |
| 1b | H$_2$ | 1.7 | 10$^7$ | 10-15 | BC Ag on Si/SiO$_2$ coated with poly(α-methylstyrene) |
| 1b | Air | 0.11 | 10$^5$ | 11 | TC gold on Si/SiO$_2$ coated with PMMA; |
| 2a | Air | 0.1 | 10$^5$ | | TC gold on Si/SiO$_2$ |
| 2b | Air | 0.51 | 10$^6$ | 28-43 | TC gold on Si/SiO2 treated with OTS |
| 3a | Air | 0.11 | 10$^3$ | −55 | TC gold on Si/SiO$_2$ |
| 3b | Air | 0.10 | 10$^5$ | 15 | TC gold on Si/SiO$_2$ treated with HMDS |
| 4 | Air | 0.64 | 10$^4$ | −20 | TC gold on Si/SiO$_2$ treated with HMDS |

$V_T$ = threshold voltage; TC = top contact; BC = bottom contact; OTS = octadecyltrichlorosilane; HMDS = hexamethyldisilazane; PMMA = poly(methyl methacrylate); Vac. = vacuum.

NDI compound 1a was reported (see Katz, H.; Johnson, J.; Lovinger, A.; Li, W. *Journal of the American Chemical Society* 2000, 122, 7787) to exhibit a measured field-effect electron mobility of 0.16 cm$^2$ V$^{-1}$ s$^{-1}$ in vacuum, but almost no field-effect electron mobility was measurable in air. PDI

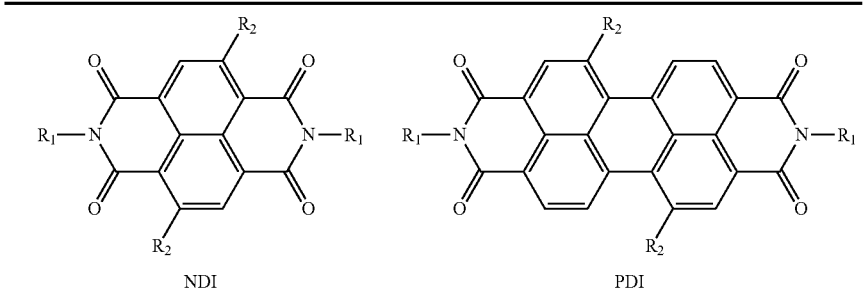

| | R$_1$ | R$_2$ | | R$_1$ | R$_2$ |
|---|---|---|---|---|---|
| 1a | C$_8$H$_{17}$ | H | 1b | C$_8$H$_{17}$ | H |
| 2a | CH$_2$C$_7$F$_{15}$ | H | 2b | CH$_2$C$_3$F$_7$ | H |
| 3a | C$_8$H$_{17}$ | CN | 3b | C$_6$H$_{12}$ | CN |
| | | | 4 | CH$_2$C$_4$F$_7$ | CN | compound 1b was reported to achieve a maximum field-effect mobility of 1.7 cm$^2$ V$^{-1}$ s$^{-1}$ in an H$_2$ atmosphere, but, the field-effect mobility was dramatically reduced to 0.11 cm$^2$ V$^{-1}$ s$^{-1}$ when the device was exposed to air (Chesterfield, R.; McKeen, J.; Newman, C.; Ewbank, P.; da Silva, D.; Bredas, J.; Miller, L.; Mann, K.; Frisbie, C. *Journal of Physical Chemistry B* 2004, 108, 19281). PDI compound 4 was reported to have an air-stable field-effect electron mobility of 0.64 cm$^2$ V$^{-1}$ s$^{-1}$ (see Jones, B.; Ahrens, M.; Yoon, M.; Facchetti, A.; Marks, T.; Wasielewski, M. *Angew Chem Int Ed* 2004, 43, 6363), but only produced an on/of ratio of 1×10$^4$ in the reported OFET, and suffered from an undesirable threshold voltage of −20 volts.

It is believed in the art that the mobility of electrons through materials comprising such NDI and/or PDI compounds results from a combination of the electronic properties of the highly conjugated compounds, as well as (at least in some favorable cases) face-to-face π-stacking interactions between neighboring NDI or PDI small molecules in the solid state.

Yan and Zhao (Org. Lett. 2009, 11(15) 3426-3419) reported the synthesis and characterization of several solution processable bis(PDI) oligomeric compounds bridged by phenyl or acetylene groups, as shown below:

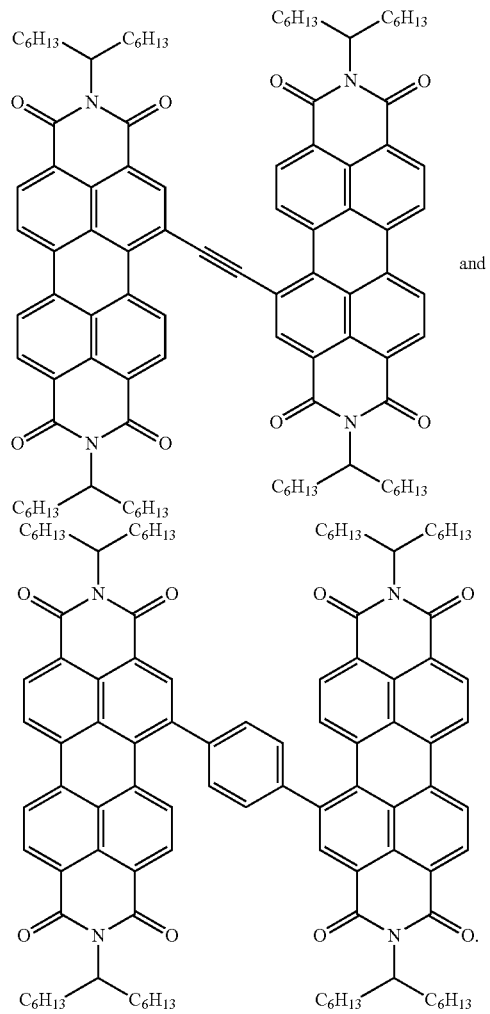

Yan and Zhao noted that in some such PDI oligomers (connected at the bay positions) reported in the prior art, some bridging groups appeared to induce an electronic effect on the LUMOs of the PDI groups. With respect to the PDI-X-PDI oligomers they described, Yan and Zhao concluded that an acetylene bridge permitted electronic conjugation between the two perylenediimide groups, but that phenyl bridges did not permit such electronic conjugation, probably because of steric interactions between the PDI and phenyl groups that induced highly twisted/non-coplanar conformations of the PDI and bridging groups. Yan and Zhao did not report measurements of the electrical conductivity properties of the PDI-X-PDI oligomers they described as electron carrier semiconductors.

Recently in 2009, PCT Patent Publications WO 2009/144205 and WO 2009/144302 described a very wide genus of bridged bis(rylene) compounds having the formula Q-L-Q', wherein Q and Q' could be a wide variety of rylene groups that included NDI, PDI and many other groups. L was also described as including a very wide variety of cyclic and non-cyclic bridging groups. From the extremely broad genus of Q-L-Q' compounds broadly disclosed in the publications, both WO 2009/144205 and WO 2009/144302 more specifically described the specific solution processable PDI-bis-thiophene-PDI compound whose structure is shown below (where Rb is 2-ethyl-hexyl), and reported that bottom-gate, top contact field effect transistors employing that compound (and tested in air) gave measured field effect mobility values as high as 0.05 cm$^2$V$^{-1}$sec$^{-1}$, on/off ratios of 2.4×10$^6$, but suffered from undesirable threshold voltages of −15 volts. It was not clear whether or not the reported transistors were stable in air past the short time required for the electronic measurements.

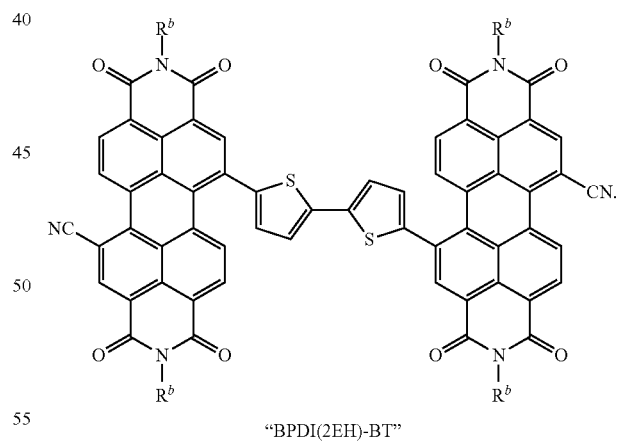

"BPDI(2EH)-BT"

However, in order to provide practically useable transistor device performance, and employ solution processing so as to reduce manufacturing costs so as to enable practical new commercial applications in organic electronic devices such as OFETs, solution processable and long-term air-stable electron transport materials having much better performance, such as low barriers for charge injection, high field-effect mobility of charge carriers (>1 cm$^2$V$^{-1}$s$^{-1}$), large $I_{ON}/I_{OFF}$ ratios (>10$^6$), and low threshold voltage (<±2.5 V) are still needed.

Accordingly, there remains a need in the art for improved solution processable organic semiconducting materials that can transport holes, and/or electrons in transistor applications in air, with high carrier mobility, high current on/off ratios, and/or threshold voltages close to zero. It is to that end that the various embodiments of the inventions described herein relate.

SUMMARY OF THE INVENTION

The various inventions and/or their various embodiments disclosed herein relate to certain naphthalene diimide (NDI) oligomers wherein the NDI groups are bonded to certain subclasses of bridging heteroaryl (hAr) groups. Examples of such "NDI-hAr-NDI" oligomeric compounds include compounds having the structures shown below:

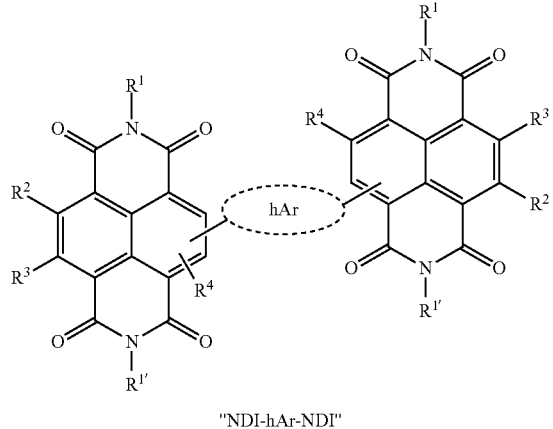

"NDI-hAr-NDI"

wherein hAr is a heteroaryl group chosen to provide desirable electronic and steric properties, and the possible identities of the "R$^z$" terminal peripheral substituent groups will be further described below.

Such oligomeric NDI-hAr-NDI, oligomers are typically electron transport semiconductors in the solid state, though they can sometimes (depending on the nature of the bridging groups and details of the transistors in which they are utilized, such as electrode materials) also transport holes, so as to also be capable of performing as ambipolar semiconductors. Such NDI-hAr-NDI, oligomers can be and often are solution processable and film forming materials. Films comprising such NDI-hAr-NDI oligomers can exhibit unexpectedly high and/or superior electron mobility values and unexpectedly low threshold voltages when they are employed in suitable OFET configurations. Furthermore, some such oligomers can potentially provide unexpectedly stable performance in the presence of air and/or water vapor.

In many embodiments, the bridging hAr heteroaryl groups (which include many fused heteroaryl groups) are bonded to the NDI groups through five-membered heteroaryl groups with few or no sterically demanding substitutents that would undesirably interact sterically with the NDI groups to induce undesirable highly non-planar "twisted" conformations that would inhibit electronic conjugation between the NDI and hAr groups. In many embodiments, the bridging hAr heterocycle groups are relatively electron rich hAr heterocycles that can provide relatively high energy highest occupied molecular orbitals ("HOMOs"), producing "low bandgap" NDI-hAr-NDI" oligomers that can have low energy charge transfer characteristics within the oligomers.

Both the electron carrying characteristics and air stability of the NDI-hAr-NDI oligomeric compounds can also be significantly altered and/or sometimes improved when the hAr groups are relatively electron withdrawing heteroaryl groups with stabilized HOMO and/or LUMO energies. Examples of NDI-hAr-NDI oligomeric compounds having such electron withdrawing heteroaryl bound thereto appear to be unexpectedly rare and/or absent from the prior art, perhaps because such compounds can be difficult or impossible to practically synthesize via typical known coupling methods.

In addition, the Applicants have unexpectedly discovered a simple and efficient method for making naphthalene diimide organotin compounds having the structure

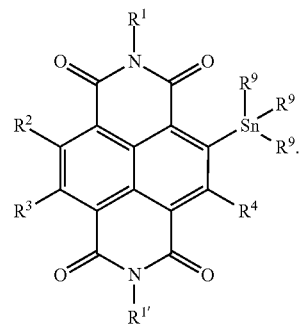

Such naphthalene diimide organotin compounds, now unexpectedly available as synthetic intermediates in view of Applicants new method for making them, can be readily coupled with functionalized precursors of a wide variety of electron withdrawing hAr heterocycles, such as heteroaryl dibromides or diiodides, to give new and previously unknown NDI-hAr-NDI oligomers wherein hAr is an electron withdrawing heterocycle. Such compounds can provide unexpectedly superior performing and ambient stable electron transport semiconductors.

Further detailed description of preferred embodiments of the various oligomers and precursors, and OFET devices comprising will be provided in the Detailed Description section below.

In particular, one embodiment provides a bis(naphthalene diimide) compound or a mixture thereof having the structure

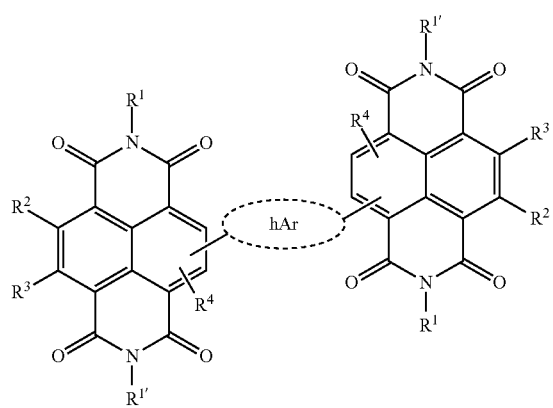

wherein
a) hAr is a heteroaryl selected from

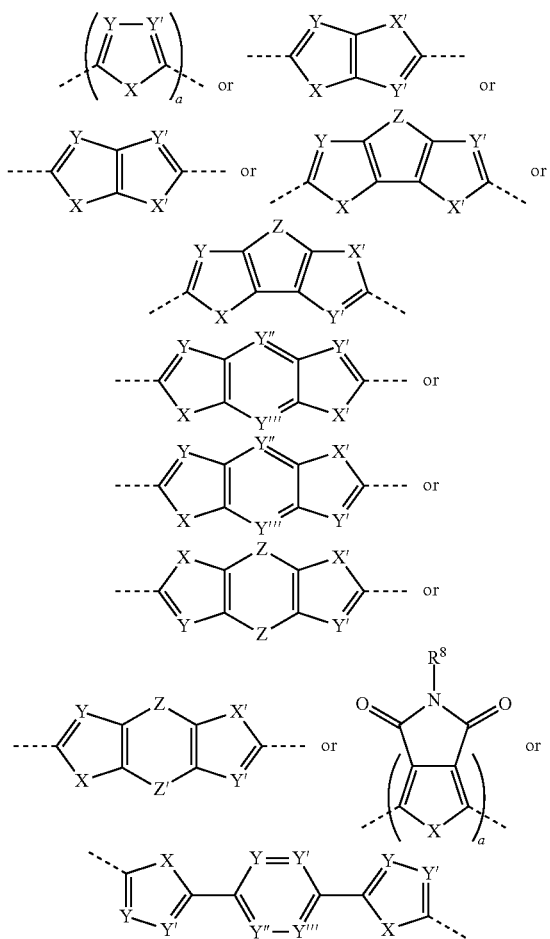

wherein
i) "a" is an integer 1, 2, 3, or 4;
ii) each X and X' is independently selected from O, S, Se, or NR$^6$, wherein R$^6$ is a C$_1$-C$_{30}$ organic group independently selected from normal, branched, or cyclic alkyl, fluoroalkyl, aryl, heteroaryl, alkyl-aryl, and alkyl-heteroaryl groups optionally substituted with one or more fluoro, cyano, alkyl, alkoxy groups;
iii) each Y, Y', Y" and Y''' is independently selected from N, and CR$^7$, where R$^7$ is hydrogen, fluoro, or a C$_1$-C$_{30}$ organic group independently selected from cyano, normal, branched, or cyclic alkyl, perfluoroalkyl, alkoxy, perfluoroalkoxy, aryl, heteroaryl, alkyl-aryl, and alkyl-heteroaryl groups, optionally substituted with one or more fluoride, cyano, alkyl, alkoxy groups;
iv) each Z and Z' is independently selected from O, S, Se, C(R$^8$)$_2$, Si(R$^8$)$_2$, NR$^8$, (CO), (CO), or C=C(CN)$_2$, wherein R$^8$ is a C$_1$-C$_{30}$ organic group independently selected from normal, branched, or cyclic alkyl, perfluoroalkyl, aryl, heteroaryl, alkyl-aryl, and alkyl-heteroaryl groups, optionally substituted with one or more fluoro, cyano, alkyl, alkoxy groups;
b) each R$^1$ and R$^{1'}$ is a C$_1$-C$_{30}$ organic group independently selected from a normal, branched, or cyclic alkyl, aryl, heteroaryl, alkyl-aryl, or alkyl-heteroaryl group optionally substituted with one or more halide, cyano, alkyl, or alkoxy groups;
c) R$^2$, R$^3$, and R$^4$ are independently selected from hydrogen, halide, or a C$_1$-C$_{30}$ organic group independently selected from cyano, normal, branched, or cyclic alkyl, fluoroalkyl, aryl, heteroaryl, alkyl aryl, acyl- and alkyl-heteroaryl groups, optionally substituted with one or more fluoro, cyano, alkyl, alkoxy groups.

In another embodiment, R$^1$, R$^{1'}$ is a C$_1$-C$_{30}$ normal, branched, or cyclic alkyl or fluoroalkyl group.

In another embodiment, R$^2$, R$^3$, and R$^4$ are independently selected from hydrogen, fluoro and cyano.

In another embodiment, hAr is a heteroaryl selected from

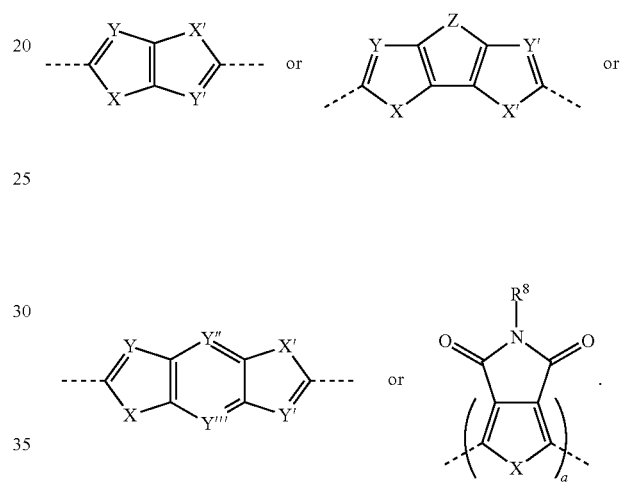

In another embodiment, hAr is a heteroaryl selected from

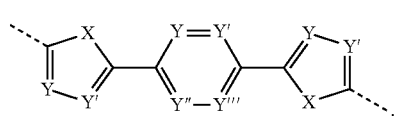

In another embodiment, X and X' are S.
In another embodiment, Y, Y', Y" and Y''' are N or CH.
In another embodiment, Y, Y', Y" and Y' are N or CH.
In another embodiment, hAr has one of the structures

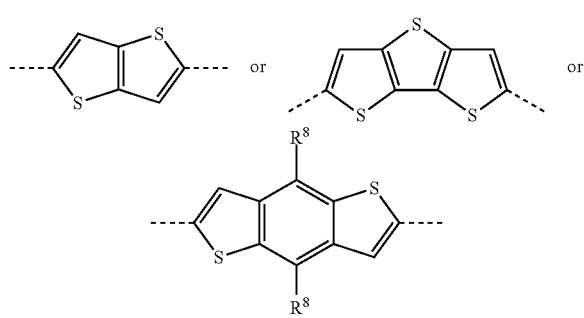

-continued

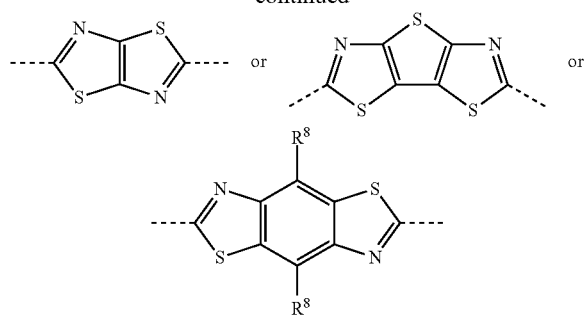

wherein $R^8$ is hydrogen, cyano, or a $C_1$-$C_{12}$ normal, branched alkyl, perfluoroalkyl, alkoxy, or perfluoroalkoxy group;

or

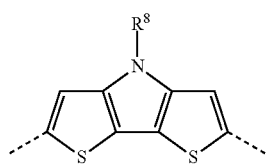

wherein $R^8$ is a $C_1$-$C_{20}$ normal or branched, alkyl, perfluoroalkyl, aryl, heteroaryl, alkyl-aryl, and alkyl-heteroaryl group, optionally substituted with one or more fluoro, cyano, alkyl, alkoxy groups, preferably a $C_1$-$C_{20}$ normal or branched, alkyl or perfluoroalkyl group;

or

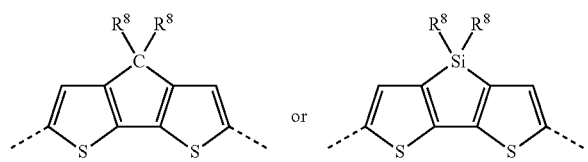

or wherein $R^8$ is hydrogen, or a $C_1$-$C_{12}$ normal or branched alkyl or perfluoroalkyl group;

or

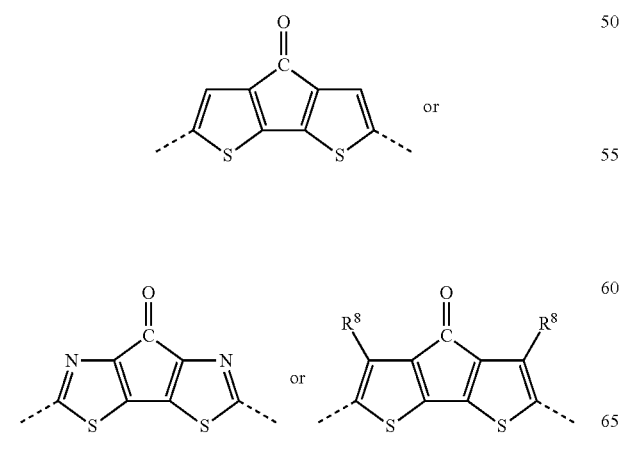

wherein $R^8$ is a $C_1$-$C_{12}$ normal or branched alkyl or perfluoroalkyl group;

or

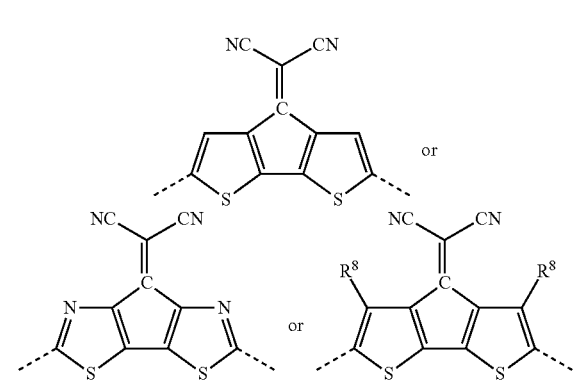

wherein $R^8$ is a $C_1$-$C_{12}$ normal or branched alkyl or perfluoroalkyl group;

or

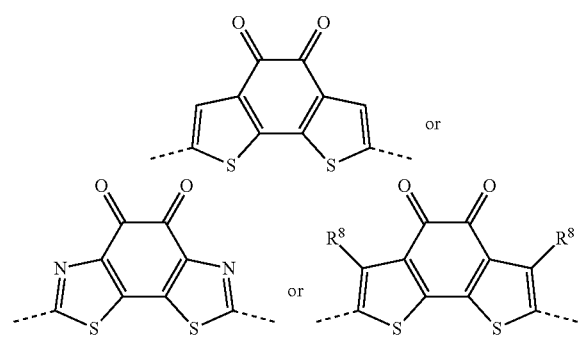

wherein $R^8$ is a $C_1$-$C_{12}$ normal or branched alkyl or perfluoroalkyl group;

or

-continued

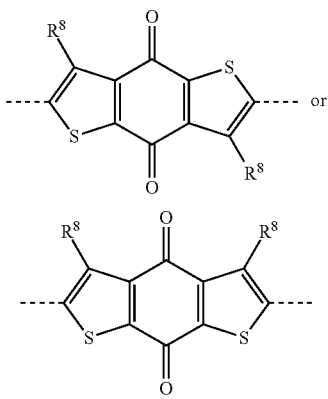

wherein $R^8$ is a $C_1$-$C_{12}$ normal or branched alkyl or perfluoroalkyl group;
or

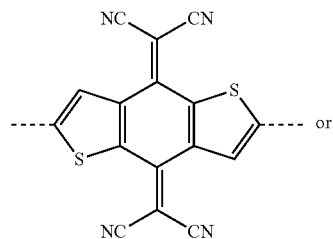

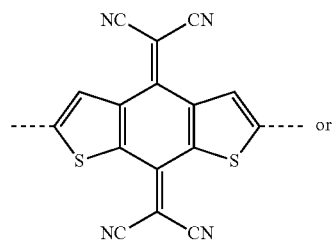

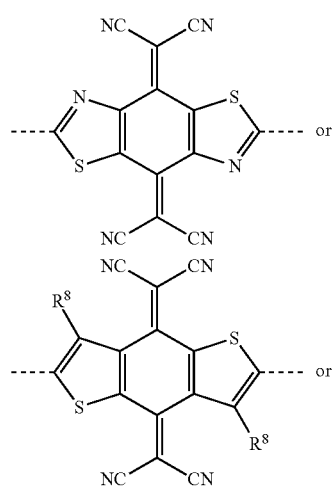

-continued

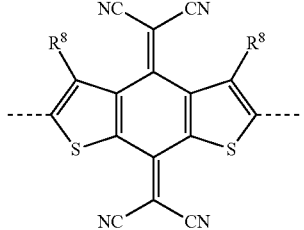

wherein $R^8$ is a $C_1$-$C_{12}$ normal or branched alkyl or perfluoroalkyl group;
or

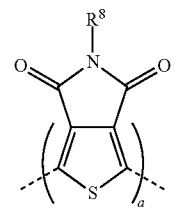

wherein $R^8$ is a $C_1$-$C_{20}$ normal or branched, alkyl or perfluoroalkyl group, wherein the alkyl group is optionally substituted with one or more fluoro, cyano, alkyl, alkoxy groups.

In another embodiment, hAr has the structure;

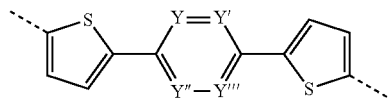

wherein Y, Y', Y" and Y'" are N or $CR^7$, and $R^7$ is hydrogen or a $C_1$-$C_{20}$ normal or branched, alkyl or perfluoroalkyl group, wherein the alkyl group is optionally substituted with one or more fluoro, cyano, alkyl, alkoxy groups. In one embodiment, Y, Y', Y" and Y'" are N.

Other embodiments provide an electronic device comprising one or more compounds as described herein. For example, the electronic device can be a transistor, including a top gate-bottom contact transistor. In one embodiment, the top gate comprises an organic polymer dielectric layer in contact with the one or more compounds, and a high dielectric constant metal oxide dielectric layer in contact with the organic polymer dielectric layer. In another embodiment, the electronic device is a complementary-like inverter.

Another embodiment provides a method for making the electronic device from the compounds described herein, wherein the method of making comprises at least one step comprising depositing an organic semiconductor layer by inkjet printing. In one embodiment, the organic semiconducting layer is deposited on a flexible substrate by inkjet printing.

BRIEF DESCRIPTION OF THE FIGURES

FIG. 10a shows the chemical structure of NDI-DTP-NDI, FIG. 10b shows device structure of a top-gate OFET, FIG. 10c shows the structure of a complementary-like inverter with two ambipolar OFETs, FIG. 10d shows output characteristics of a representative OFET with NDI-DTP-NDI exhibiting an electron mobility of 1.1 $cm^2$/Vs and a hole mobility of 0.01 $cm^2$/Vs in the saturation regime, and FIG. 10e shows a schematic of a complementary-like inverter, with T1 acting as a p-channel device and T2 as an n-channel device.

FIG. 14 illustrates OFET results for 1,4-dioxane solvent and Au electrode.

FIG. 15 illustrates OFET results for dichlorobenzene solvent and Au electrode.

FIG. 16 illustrates OFET results for dichlorobenzene solvent and Ag electrode.

FIG. 17 illustrates OFET results for mesitylene-tetralin solvent and Au electrode.

FIG. 18 illustrates OFET results for mesitylene-tetralin solvent and Ag electrode.

FIG. 19 illustrates OFET results for tetrachloroethane solvent and Au electrode.

FIG. 22 illustrates printed OFET results for dichlorobenzene solvent and Au electrode.

FIG. 24 illustrates printed flexible OFET results for dichlorobenzene solvent and pAg electrode.

FIG. 27 illustrates air stability testing for rigid OFETs.

FIG. 30 illustrates air stability testing for flexible and printed OFETs.

FIG. 32a illustrates OFET results for Bis(CN-NDI)DTP in Table 2a, No. 1; FIG. 32b illustrates OFET results for in Table 2a, No. 3; FIG. 32c illustrates OFET results for in Table 2a, No. 4.

FIG. 33a illustrates OFET results for NDI-Tz-Tz-NDI in Table 2a, No. 4;

FIG. 33b illustrates OFET results for NDI-Tz-Tz-NDI in Table 2a, No. 5.

FIG. 35a illustrates OFET results for Bis (CN-NDI)DTP/PS blend in Table 3a, No. 4.

FIG. 37 illustrates the air stability of Bis(CN-NDI12) BTTZ and Bis(CN-NDI12) BTTZ/PS blend.

FIG. 39a illustrates OFET results for Bis(NDI-F7)DTP in Table 5a;

DETAILED DESCRIPTION OF THE INVENTION

Figure 1A:
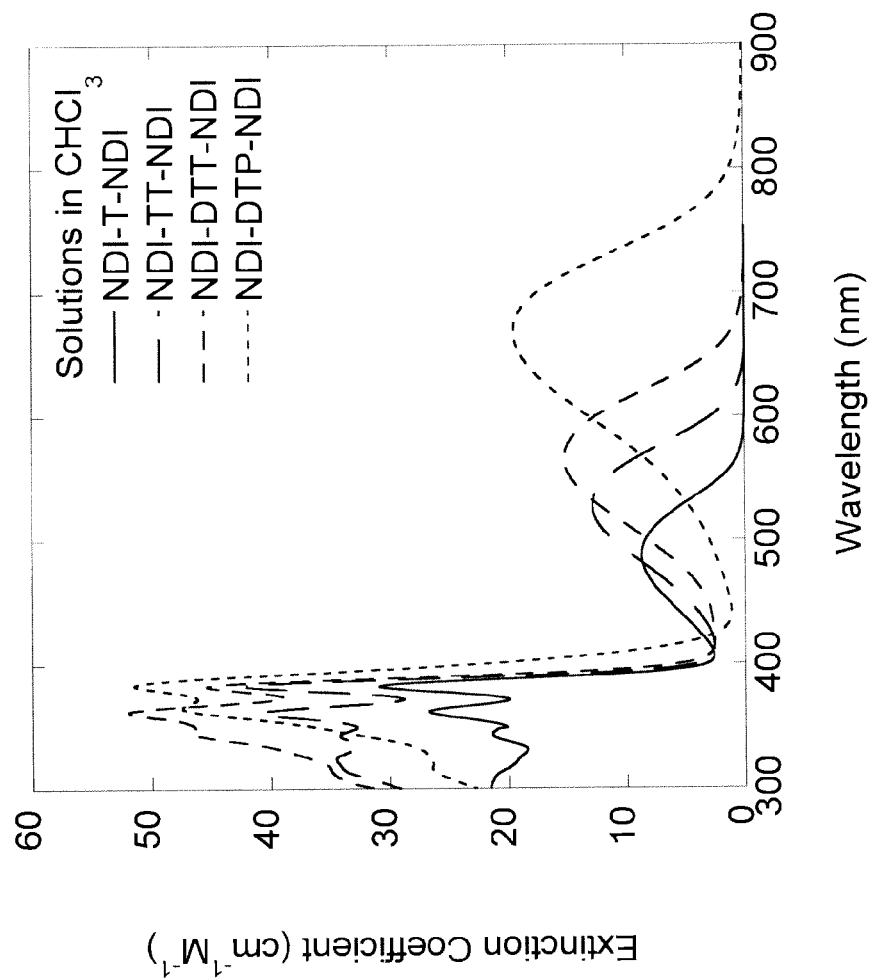
FIG. 1a shows UV-vis absorption of the NDI-T-NDI, NDI-TT-NDI, NDI-DTT-NDI, and NDI-DTP-NDI oligomers in chloroform.

The Detailed Description, examples and data herein provide exemplary description of the synthesis and use of the various compounds and/or oligomers described herein, and various electronic devices such as OFETs comprising the various compounds and/or oligomers descriptions, and methods for their manufacture and use. In view of those disclosures, one of ordinary skill in the art will be readily able to envision many additional embodiments or sub-embodiments of the broader inventions disclosed and claimed herein to be obvious, and understand that the specification disclosures herein are not intended to limit the claims herein, and that many such alternative embodiments and sub-embodiments can be made without departing from the intended scope of the broad inventions disclosed herein.

Priority U.S. provisional application 61/475,888 filed Apr. 15, 2011; priority U.S. provisional application 61/579,608 filed Dec. 22, 2011; and priority provisional application 61/591,767 filed Jan. 27, 2012 are incorporated by reference in their entirety.

Definitions

In the application, where an element or component is said to be included in and/or selected from a list of recited elements or components, it should be understood that in related embodiments explicitly contemplated here, the element or component can also be any one of the individual recited elements or components, or can also be selected from a group consisting of any two or more of the explicitly listed elements or components. Further, it should be understood that elements and/or features of a composition, an apparatus, or a method described herein can be combined in a variety of ways without departing from the scope and disclosures of the present teachings, whether explicit or implicit herein.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a +−10% variation from the nominal value.

As used herein, an "electron-transport semiconductor" refers to a semiconductor material that employs electrons as the majority current carriers. Preferably, electron-transport semiconductors effectively exclusively employ electrons as current carriers (i.e. the ratio of electron mobility to hole mobility for the material is at least $10^4$). When an electron-transport semiconductor material is deposited on a substrate, it can provide an electron mobility in excess of about $10^{-6}$ $cm^2/Vs$. In the case of field-effect devices, an electron-transport semiconductor can also exhibit a field-effect electron mobility in excess of about $10^{-6}$ $cm^2/Vs$ and/or a current on/off ratio of greater than about 10, or $10^2$, or $10^3$, or $10^4$. However, it should be understood that the experimentally measured values of field effect electron and hole mobility, current on/off ratios, and the like measured from OFETS can be very significantly dependent on the identity and physical arrangement of the other components in such an OFET.

As used herein, an "ambipolar semiconductor material" or an "ambipolar semiconductor" refers to a semiconductor material employing both electrons and holes as current carriers, wherein the ratio of electron mobility to hole mobility is less than about $10^4$. In many embodiments, when an electron transport semiconductor material is deposited on a substrate, it can provide an electron mobility in excess of about $10^{-6}$ $cm^2/Vs$.

As used herein, a compound (such as the NDI-hAr-NDI oligomers) can be considered "ambient stable" or "stable at ambient conditions" when the carrier mobility, threshold voltage, or current on/off ratio of an OFET comprising the compound is maintained at about its initial measurement when the compound is exposed to ambient conditions, for example, air, ambient temperature, and humidity, over a period of time. For example, a compound can be described as ambient stable if its carrier mobility, and/or threshold voltage, and/or on/off ratio of an OFET comprising the compound does not vary more than 20%, or more than 10%, from its initial value after exposure to ambient conditions, including, air, humidity and temperature, for example over a 3 day, 5 day, or 10 day period.

As used herein, "solution-processable" refers to compounds, oligomers (e.g., bispolycyclic compounds), polymers materials, or compositions that can be used in various solution-phase processes including spin-coating, printing (e.g., inkjet printing, screen printing, pad printing, offset printing, gravure printing, flexographic printing, lithographic printing, and the like), spray coating, electrospray coating, drop casting, dip coating, and blade coating.

As used herein, a "fused ring" or a "fused ring moiety" refers to a polycyclic or polyaryl or polyheteroaryl ring group having at least two rings where at least one of the rings is aromatic and such aryl or heteroaryl ring has a bond in common with at least one other ring that can be aromatic or non-aromatic, and carbocyclic or heterocyclic. These polycyclic ring systems are often planar and π-conjugated, and include optionally substituted bicyclic and tricyclic fused heteroaryl compounds. In many embodiments of the various inventions disclosed herein, the oligomers and/or compounds described comprise within their structure fused heteroaryl groups that can include the π-conjugated bicyclic and tricyclic heteroaryl groups shown below, wherein a dashed line represents a bond to another group.

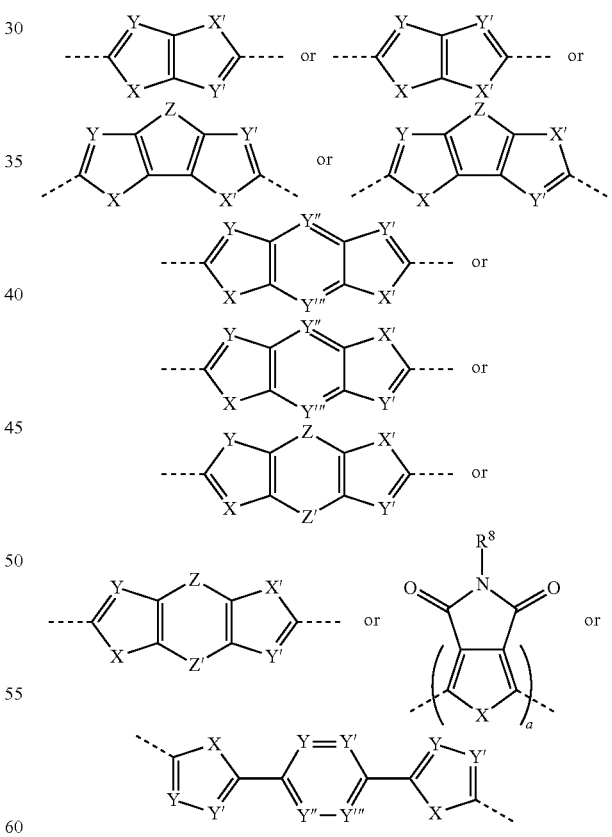

wherein
i) each X and X' is independently selected from O, S, Se, or $NR^6$, wherein $R^6$ is a terminal organic group;
ii) each Y, Y', Y" and Y''' is independently selected from N, and $CR^7$, where $R^7$ is hydrogen, halide, or a terminal organic group;

iii) each Z and Z" is independently selected from O, S, Se, $C(R^8)_2$, $Si(R^8)_2$, $NR^8$, (CO), $(CO)_2$ or $C=C(CN)_2$, wherein $R^8$ is a terminal organic group.

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and iso-propyl), butyl (e.g., n-butyl, iso-butyl, sec-butyl, tert-butyl), pentyl groups (e.g., n-pentyl, iso-pentyl, neopentyl), and the like. In various embodiments, an alkyl group can have 1 to 30 carbon atoms, for example, 1-20 carbon atoms (i.e., Ci-20 alkyl group). In some embodiments, an alkyl group can have 1 to 6 carbon atoms, and can be referred to as a "lower alkyl group." Examples of lower alkyl groups include methyl, ethyl, propyl (e.g., n-propyl and iso-propyl), and butyl groups (e.g., n-butyl, iso-butyl, sec-butyl, tert-butyl). In some embodiments, alkyl groups can be substituted with 1-5 $R^1$ groups and $R^1$ is as defined herein.

As used herein, "haloalkyl" refers to an alkyl group having one or more halogen substituents. At various embodiments, a haloalkyl group can have 1 to 20 carbon atoms, for example, 1 to 10 carbon atoms (i.e., $C_1$-$C_{10}$ haloalkyl group). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups where all of the hydrogen atoms are replaced with halogen atoms (e.g., perfluoroalkyl groups such as $CF_3$ and $C_2F_5$), are included within the definition of "haloalkyl."

As used herein, "alkoxy" refers to —O-alkyl group. Examples of alkoxy groups include, but are not limited to, methoxy, ethoxy, propoxy (e.g., n-propoxy and isopropoxy), t-butoxy groups, and the like. The alkyl group in the —O-alkyl group can be substituted with 1-5 $R^1$ groups and $R^1$ is as defined herein.

As used herein, "heteroatom" refers to an atom of any element other than carbon or hydrogen and includes, for example, nitrogen, oxygen, silicon, sulfur, phosphorus, and selenium.

As used herein, "heteroaryl" refers to an aromatic monocyclic ring system containing at least one ring heteroatom selected from oxygen (O), nitrogen (N), sulfur (S), silicon (Si), and selenium (Se), or a polycyclic ring system wherein at least one of the rings present in the ring system is aromatic and contains at least one ring heteroatom. A heteroaryl group, as a whole, can have, for example, from 5 to 16 ring atoms and contain 1-5 ring heteroatoms (i.e., 5-16 membered heteroaryl group). In some embodiments, heteroaryl groups can be substituted with one or more terminal $R^1$ groups, where $R^1$ is as defined herein. Both substituted and unsubstituted heteroaryl groups described herein can comprise between 1-30, or 1-20 carbon atoms, including the $R^1$ substituents.

Naphthalene Diimide Oligomers

The various inventions and/or their embodiments disclosed herein relate to various embodiments and subembodiments of certain naphthalene diimide (NDI) oligomers wherein the NDI groups are bonded to heteroaryl (hAr) and/or linking groups. Examples of such NDI oligomers include compounds having the structures shown below, wherein the conventional substituent numbering schemes for the NDI groups are indicated, as well as an "NDI-hAr-NDI" acronym labels for the oligomers as a class:

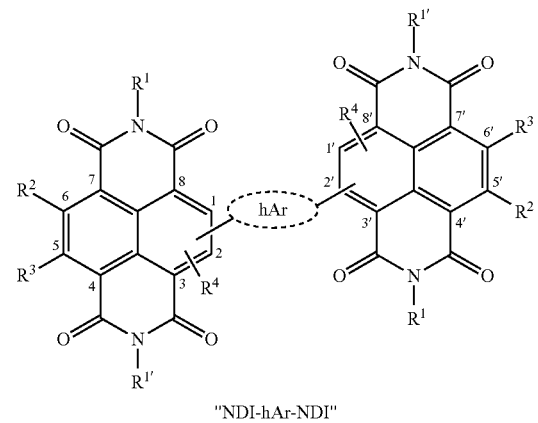

"NDI-hAr-NDI"

wherein, hAr is a heteroaryl group, and the possible identities of the various "$R^z$" terminal peripheral substituent groups will be further described below.

As will be further detailed below, such NDI-hAr-NDI, oligomers are typically solution processable and film forming materials.

As will be further described and exemplified below, such NDI-hAr-NDI, oligomers are typically electron transporting semiconductors in the solid state. However, unexpectedly, and depending upon the other materials employed in electronic devices comprising those compounds, it has also been discovered that such compounds can sometimes also simultaneously transport holes, so as to sometimes serve as ambipolar semiconductors.

Films comprising such NDI-hAr-NDI, oligomers often exhibit unexpectedly high and/or superior field effect electron mobility values and low threshold voltages when they are employed in OFET applications and/or devices. Furthermore, such oligomers can provide devices with unexpectedly superior performance and ambient stability (i.e. in the presence of air and/or water vapor).

NDI-hAr-NDI Oligomeric Compounds

In some embodiments, the inventions described herein relate to novel NDI-hAr-NDI oligomers or a mixture thereof having the generic structure

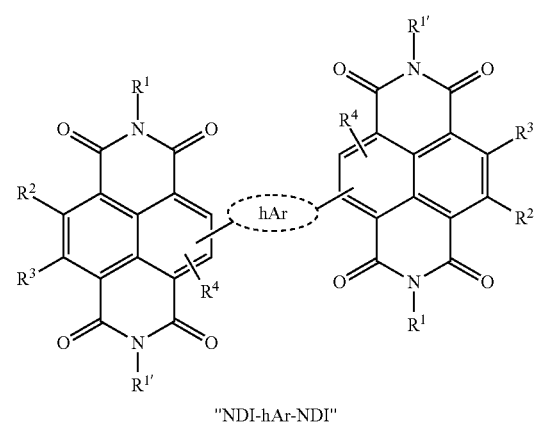

"NDI-hAr-NDI"

wherein
a. hAr is a heteroaryl that bridges the two NDI group, selected from

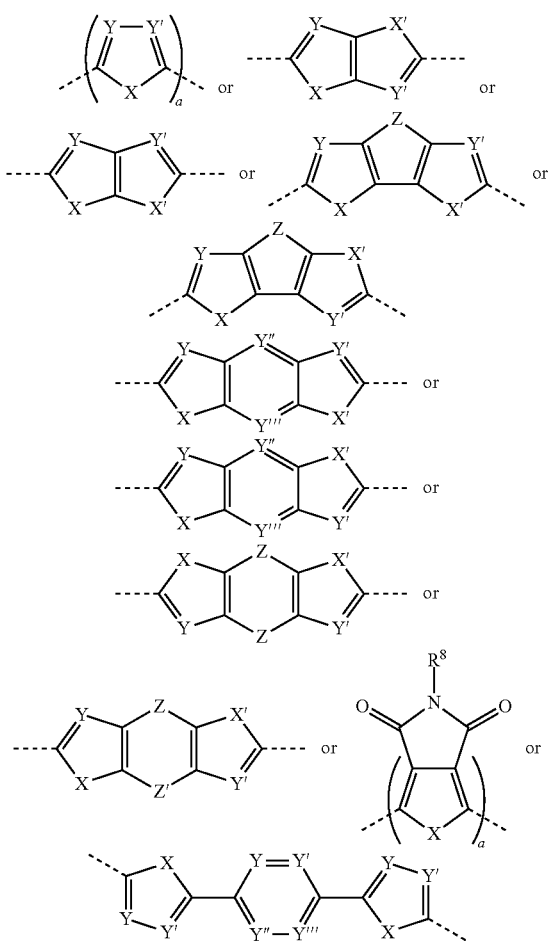

often selected from a normal, branched, or cyclic alkyl, aryl, heteroaryl, alkyl-aryl, or alkyl-heteroaryl group optionally substituted with one or more halide, cyano, alkyl, or alkoxy groups. In many embodiments, $R^1$ and $R^{1'}$ can be normal, branched, or cyclic alkyl or perfluoroalkyl groups.

In one embodiment, $R^1$ and $R^{1'}$ are each independently a $C_1$-$C_{30}$ or $C_1$-$C_{20}$ or $C_1$-$C_{10}$ alkyl group optionally substituted by one or more fluoro, cyano, alkyl, alkoxy groups. In one embodiment, the $C_1$-$C_{30}$ or $C_1$-$C_{20}$ or $C_1$-$C_{10}$ alkyl group is substituted by one or more fluoro groups.

The $R^2$, $R^3$, and $R^4$ groups are typically independently selected terminal substituent groups for ring carbon atoms of the NDI groups. The $R^2$, $R^3$, and $R^4$ groups can be independently selected from hydrogen, halide, or a $C_1$-$C_{30}$, $C_1$-$C_{20}$, or $C_1$-$C_{12}$ organic group, such as for example independently selected cyano, normal, branched, or cyclic alkyl, fluoroalkyl, aryl, heteroaryl, alkyl-aryl, acyl- and alkyl-heteroaryl groups, optionally substituted with one or more fluoro, cyano, alkyl, alkoxy groups. Variation of the $R^2$, $R^3$, and $R^4$ groups can also be used to "tune" the electronic characteristics of the NDI groups, as well as the solubility, solution processability, and solid state properties of the final resulting compounds.

In many embodiments of the NDI-hAr-NDI oligomers, $R^4$ which is near the bridging "hAr" heteroaryl groups, is hydrogen, a halogen, or another sterically small and undemanding group, so as minimize unfavorable steric interactions with the bridging hAr groups, which could inhibit the ability of the NDI and bridging hAr groups to adopt coplanar or nearly coplanar conformations that maximize electronic conjugation between the NDI and bridging hAr groups. In many embodiments, $R^2$, $R^3$, and $R^4$ are independently selected from hydrogen, fluoro and cyano groups. In many embodiments, the $R^1$ groups are the same, $R^4$ is hydrogen, and the point of attachment to the hAr ring relative to the $R^2$ and $R^3$ groups is the same in both NDI groups, as shown in the diagram below:

wherein
i. "a" is an integer 1, 2, 3, or 4;
ii. each X and X' is independently selected from O, S, Se, or $NR^6$, wherein $R^6$ is a organic group, which preferably is a $C_1$-$C_{30}$ or $C_1$-$C_{20}$ or $C_1$-$C_{10}$ organic group;
iii. each Y, Y', Y" and Y''' is independently selected from N, and $CR^7$, where $R^7$ is hydrogen, fluoro, or an organic group, which preferably is a $C_1$-$C_{30}$ or $C_1$-$C_{20}$ or $C_1$-$C_{10}$ organic group;
iv. each Z and Z' is independently selected from O, S, Se, $C(R^8)_2$, $Si(R^8)_2$, $NR^8$, (CO), $(CO)_2$ or $C=C(CN)_2$, wherein $R^8$ is an organic group, which preferably is a $C_1$-$C_{30}$ or $C_1$-$C_{20}$ or $C_1$-$C_{10}$ organic group;
b. each $R^1$ and $R^{1'}$ is a $C_1$-$C_{30}$ organic group, which preferably is a $C_1$-$C_{30}$ or $C_1$-$C_{20}$ or $C_1$-$C_{10}$ organic group;
c. $R^2$, $R^3$, and $R^4$ are independently selected from hydrogen, halide, or a $C_1$-$C_{30}$ organic group which preferably is a $C_1$-$C_{30}$ or $C_1$-$C_{20}$ or $C_1$-$C_{10}$ organic group.

Each $R^1$ and $R^{1'}$ group can be an independently selected terminal substituent organic group for the nitrogen atoms of the NDI groups described herein, although in many embodiments, $R^1$ and $R^{1'}$ can be the same terminal group. Variation of the $R^1$ and/or $R^{1'}$ groups can be used to "tune" the electronic characteristics of the NDI or PDI groups, as well as the solubility, solution processability, and solid state properties of the final resulting oligomeric compounds. $R^1$ and $R^{1'}$ can potentially be any organic group that is chemically, thermally, and electrochemically stable under the conditions of operation of an OFET device containing the compounds, but are

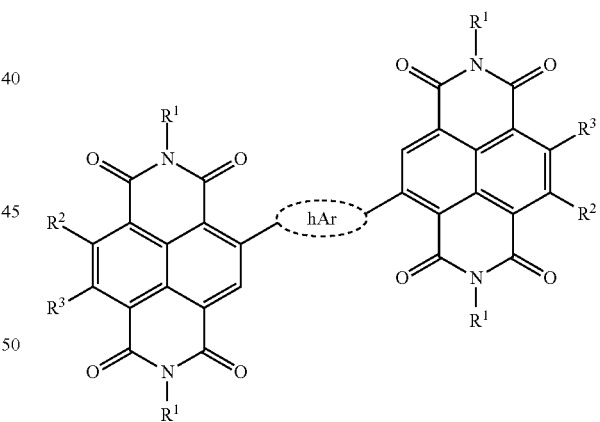

In such compounds, $R^3$ is a favored point of attachment for an electron withdrawing substituent, such as fluoride, cyano, or trifluoroalkyl groups, which can desirably lower the energy of the Lowest Unoccupied Molecular Orbital (LUMO) of the NDI groups and/or the oligomers, and increase the air stability of the resulting compounds. In one embodiment, $R^3$ is a cyano group.

In the NDI-hAr-NDI oligomers, the hAr groups bridging the NDI groups (or bridging similar PDI groups in PDI oligomers) can be one or more bivalent heteroaryl groups, as defined elsewhere herein. It is preferred that the hAr bridging groups are bonded to the NDI groups through sterically less demanding 5 membered heteroaryl groups (such as thiophenes, as opposed to six-membered heteroaryls, such as pyridines) without non-hydrogen terminal substituents at the α-positions of the five membered heteroaryl rings bonded to the NDI groups, so as to diminish unfavorable steric interactions with the NDI groups that could increase the degree of out of plane twisted conformations of the oligomers that would inhibit electronic conjugation between the NDI and hAr groups, or inhibit close π-π/stacking with neighboring oligomers in the solid state.

In many embodiments of the NDI-hAr-NDI oligomers, the bivalent hAr can be one or more of the generic heteroaryl groups whose structure is shown below. It should be noted that throughout this specification and the drawings therein, bonds that are points of attachment to other groups in a compound or oligomer are symbolized with dashed lines (-----).

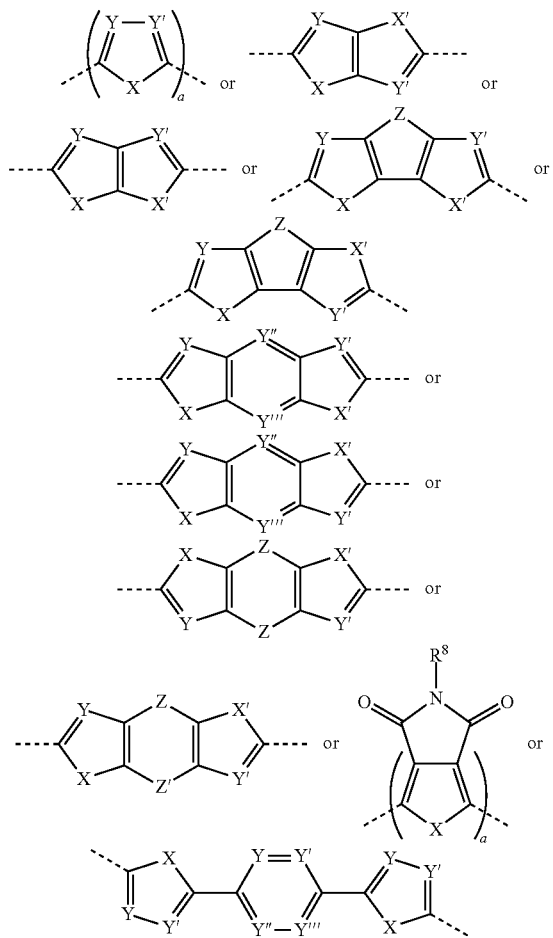

wherein
  i. "a" is an integer 1, 2, 3, or 4;
  ii. each X and X' is independently selected from O, S, Se, or $NR^6$, wherein $R^6$ is a $C_1$-$C_{30}$ organic group, such as for example an independently selected normal, branched, or cyclic alkyl, fluoroalkyl, aryl, heteroaryl, alkyl-aryl, and alkyl-heteroaryl groups, which can be optionally substituted with one or more fluoro, cyano, alkyl, alkoxy groups;
  iii. each Y, Y', Y" and Y'" is independently selected from N, and $CR^7$, where $R^7$ is hydrogen, fluoro, or a $C_1$-$C_{30}$ organic group, such as for example an independently selected cyano, normal, branched, or cyclic alkyl, perfluoroalkyl, alkoxy, perfluoroalkoxy, aryl, heteroaryl, alkyl-aryl, and alkyl-heteroaryl groups, which can be optionally substituted with one or more fluoride, cyano, alkyl, alkoxy groups;
  iv. each Z and Z' is independently selected from O, S, Se, $C(R^8)_2$, $Si(R^8)_2$, $NR^8$, (CO), $(CO)_2$ or $C=C(CN)_2$, wherein $R^8$ is a $C_1$-$C_{30}$ organic group, for example independently selected from normal, branched, or cyclic alkyl, perfluoroalkyl, aryl, heteroaryl, alkyl-aryl, and alkyl-heteroaryl groups, optionally substituted with one or more fluoro, cyano, alkyl, alkoxy groups.

In many related embodiments of the generic bivalent hAr heteroaryls shown above,
  a. X and X' can be S, and/or
  b. Y, Y', Y" and Y'" can be N or CH, and/or
  c. Y" and Y'", can be $CR^7$, and/or
  d. Z and Z' can be S or $NR^8$, and/or
  e. Z and Z' can be (CO), i.e. a carbonyl group, and/or
  f. Z and Z' can be $(CO)_2$, i.e. an α-biscarbonyl group, and/or
  g. Z and Z' can be $C=C(CN)_2$, ie. a substituted malanonitrile group, and/or
  h. Z and Z' can be $C(R^8)_2$ or $Si(R^8)_2$.

In many embodiments, it is preferred that X and X' can be S, and Y, Y', can be N or CH so that no large substituents for the five membered rings of the hAr groups significantly interact sterically with the NDI groups so, as to prevent co-planar conformations of the NDI and hAr groups.

In some embodiments of the NDI-hAr-NDI oligomers, hAr is a bivalent heteroaryl formed by linking five membered bivalent heteroaryls having the structure shown below, wherein a is an integer 1, 2, 3, or 4; such as for example a single thiophene group, as also shown below. In some embodiments, a is 1. In some embodiments, a is not 2.

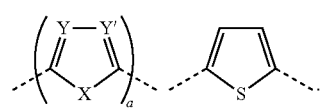

In many embodiments of the NDI-hAr-NDI oligomers hAr is a bivalent fused heteroaryl having any one of the structures shown below;

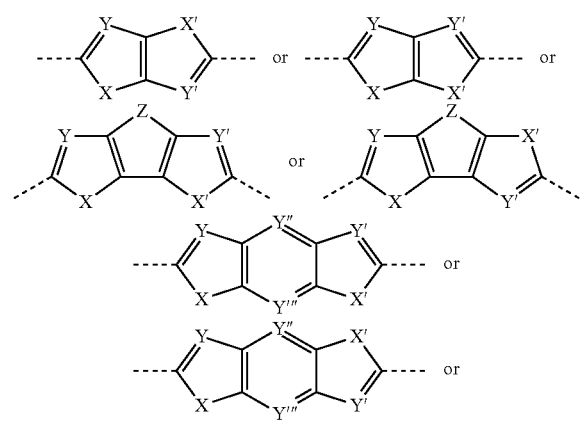

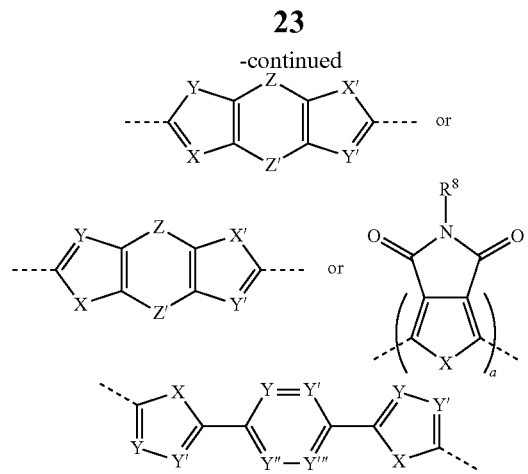

wherein X, X', Y, Y', Y'', Y''', Z and Z' can be defined in any of the ways described above.

In some embodiments, the hAr divalent fused heterocycles are selected from the structures shown below;

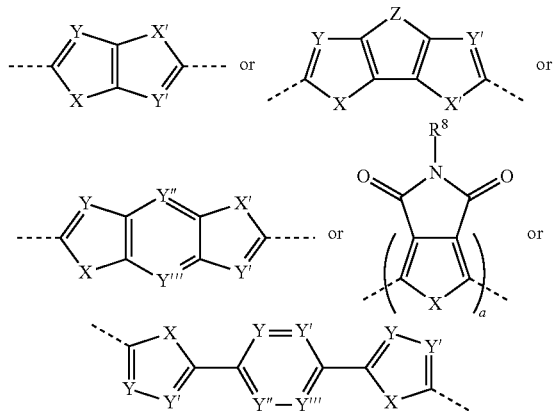

wherein X, X', Y, Y', Y'', Y''', Z and Z' can be defined in any of the ways described above.

Specific examples of such divalent fused hAr groups include those shown below:

a. Electron rich fused dithiophenes such as

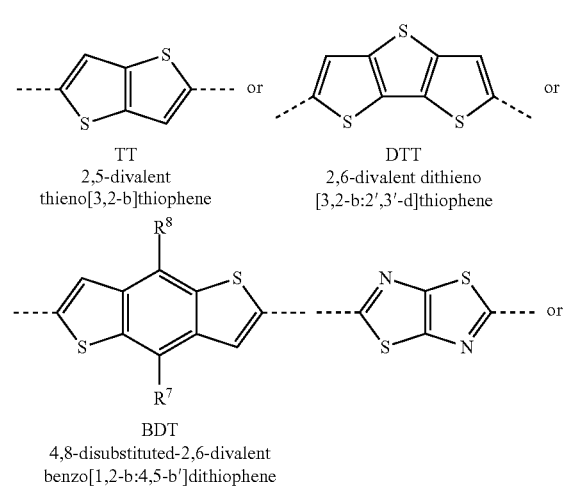

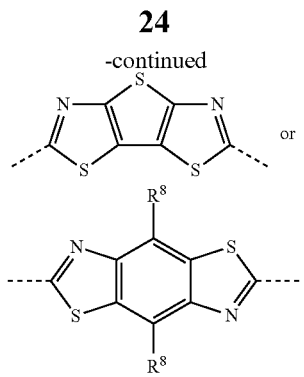

wherein $R^8$ is hydrogen, cyano, or a $C_1$-$C_{12}$ normal, branched alkyl, perfluoroalkyl, alkoxy, or perfluoroalkoxy group, or b. Electron rich fused dithienopyrroles such as

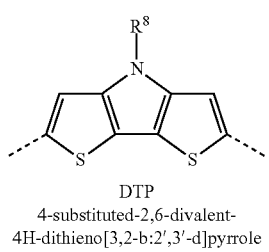

DTP
4-substituted-2,6-divalent-
4H-dithieno[3,2-b:2',3'-d]pyrrole wherein $R^8$ is a $C_1$-$C_{20}$ normal or branched, alkyl, perfluoroalkyl, aryl, heteroaryl, alkyl-aryl, and alkyl-heteroaryl group, optionally substituted with one or more fluoro, cyano, alkyl, alkoxy groups, or c. Electron rich methylene and silylene bridged dithiophenes such as

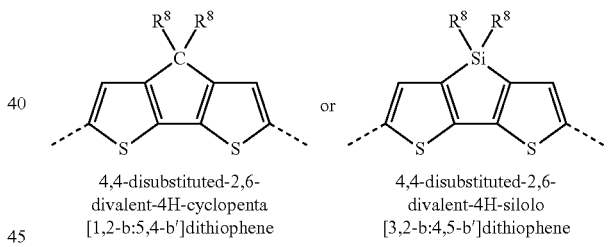

4,4-disubstituted-2,6-divalent-4H-cyclopenta[1,2-b:5,4-b']dithiophene 4,4-disubstituted-2,6-divalent-4H-silolo[3,2-b:4,5-b']dithiophene wherein $R^8$ is hydrogen, or a $C_1$-$C_{12}$ normal or branched alkyl or perfluoroalkyl group.

In one embodiment, the hydrogen in one or more of the —CH moieties is replaced by a $C_1$-$C_{12}$ normal or branched alkyl or perfluoroalkyl group.

In related embodiments, the NDI-hAr-NDI oligomers are bridged by electron withdrawing fused hAr heteroaryls such as a. Carbonyl bridged fused bivalent heteroaryls such as

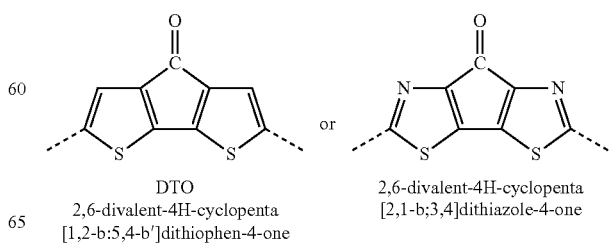

DTO
2,6-divalent-4H-cyclopenta
[1,2-b:5,4-b']dithiophen-4-one 2,6-divalent-4H-cyclopenta
[2,1-b;3,4]dithiazole-4-one b. Bis-α-dicarbonyl bridged fused heteroaryls such as

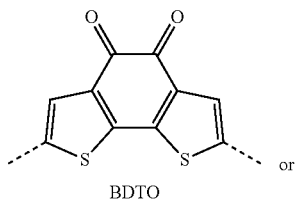

BDTO
2,7-divalent-benzo[2,1-b:3,4-b']dithiophene-4,5-dione

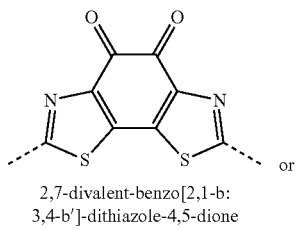

2,7-divalent-benzo[2,1-b:3,4-b']-dithiazole-4,5-dione

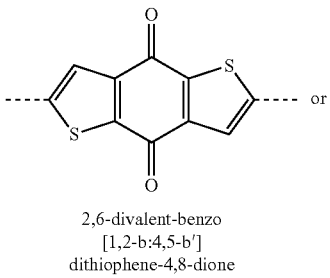

2,6-divalent-benzo[1,2-b:4,5-b']dithiophene-4,8-dione

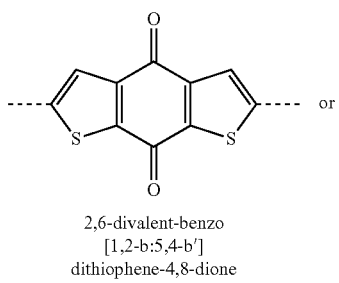

2,6-divalent-benzo[1,2-b:5,4-b']dithiophene-4,8-dione

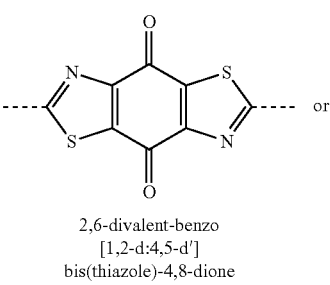

2,6-divalent-benzo[1,2-d:4,5-d']bis(thiazole)-4,8-dione c. Divalent bisheteroaryl substituted malononitriles such as

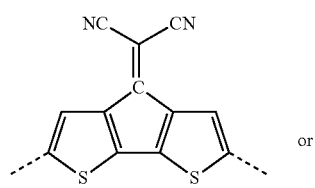

2-(2,6-divalent-4H-cyclopenta[1,2-b:5,4-b']dithiophen-4-ylidene)malononitrile

-continued

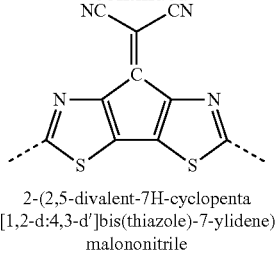

2-(2,5-divalent-7H-cyclopenta[1,2-d:4,3-d']bis(thiazole)-7-ylidene)malononitrile d. Divalent trisheteroaryl bridged dimalononitriles such as

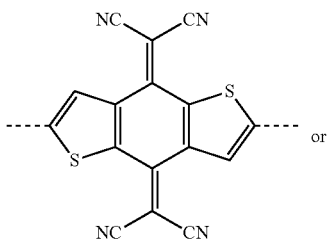

2,2'-(2,6-divalent benzo[1,2-b:4,5-b']dithiophene-4,8-diylidene)dimalononitrile

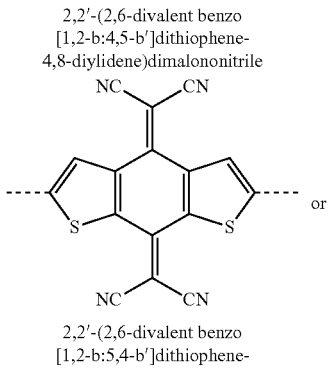

2,2'-(2,6-divalent benzo[1,2-b:5,4-b']dithiophene-4,8-diylidene)dimalononitrile

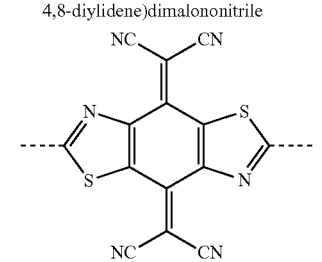

2,2'-(2,6-divalent benzo[1,2-d:4,5-d']bis(thiazole)-4,8-diylidene)dimalononitrile or e. Oligomeric divalent thienopyrroledliones such as

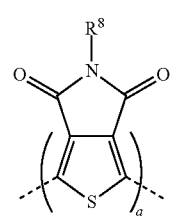

TI
5-substituted-1,3-divalent-4H-thieno[3,4-c]pyrrole-4,6(5H)-dione wherein $R^8$ is a $C_1$-$C_{20}$ normal or branched, alkyl, perfluoroalkyl, aryl, heteroaryl, alkyl-aryl, and alkyl-heteroaryl group, optionally substituted with one or more fluoro, cyano, alkyl, alkoxy groups. In many embodiments, $R^8$ is a $C_1$-$C_{20}$ normal or branched alkyl or perfluoroalkyl group.

f. Oligomeric dithieno aryl or heteroaryl derivatives such as

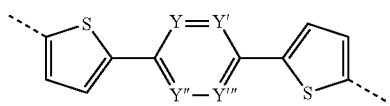

wherein Y, Y', Y" and Y''' are N or $CR^7$, and $R^7$ is hydrogen or a $C_1$-$C_{20}$ normal or branched, alkyl or perfluoroalkyl group, wherein the alkyl group is optionally substituted with one or more fluoro, cyano, alkyl, alkoxy groups.

In one embodiment, the hydrogen in one or more of the —CH moieties is replaced by a $C_1$-$C_{12}$ normal or branched alkyl or perfluoroalkyl group.

NDI-Organotin Compounds

As outlined in the experimental section below, Applicants have unexpectedly discovered a ready and practical method for making naphthalene diimide organotin compounds (NDI-tin compounds) having the structure;

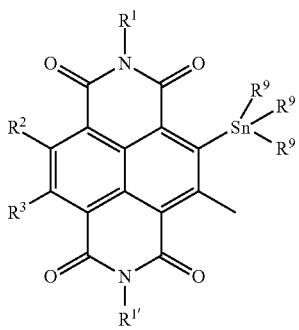

wherein
a. $R^1$ and $R^{1'}$ are independently selected from a $C_1$-$C_{30}$ normal, branched, or cyclic alkyl, aryl, heteroaryl, alkyl-aryl, or alkyl-heteroaryl group optionally substituted with one or more halide, cyano, alkyl, or alkoxy groups,
b. $R^2$, $R^3$, and $R^4$ are independently selected from hydrogen, halide, or a $C_1$-$C_{30}$ organic group independently selected from cyano, normal, branched, or cyclic alkyl, perfluoroalkyl, aryl, heteroaryl, alkyl-aryl, and alkyl-heteroaryl groups, optionally substituted with one or more fluoro, cyano, alkyl, alkoxy groups; and
c. $R^9$ is an alkyl or aryl group.

Such novel NDI-organotin compounds are highly useful as the "nucleophilic" component in well known palladium catalyzed coupling reactions for making novel NDI-hAr oligomers, wherein hAr is an electron withdrawing heteroaryl group. There are a few examples in the art (see for example WO 2009/144205 and WO 2009/144302) to make PDI oligomers coupled to electron rich hAr groups, by coupling an electron withdrawing PDI bromide with an electron rich and nucleophilic organotin hAr precursor compound. But such coupling reactions typically fail if an electron withdrawing hAr group is employed. No starting NDI organotin compounds have (to Applicants' knowledge) been previously reported, so as to enable an "inverse" coupling method for the synthesis of NDI-hAr-NDI compounds with electron withdrawn hAr substituents.

Applicants' unexpected discovery (further described herein) of a method for synthesizing the novel NDI-organotin precursor compounds enables use of "inverted" coupling reactions for the synthesis of NDI-hAr-NDI oligomers having electron withdrawn hAr heteroaryl bridging groups, a class of NDI oligomer compounds with lower lying LUMOs (low lying LUMOs have been correlated in the art with improved air and water stability).

In many embodiments, the $R^1$, $R^{1'}$, $R^2$, $R^3$, and $R^4$ groups of the NDI organotin compounds can be any of the same groups as disclosed above for the NDI-hAr-NDI oligomers. In some embodiments, $R^1$ is a $C_1$-$C_{30}$ normal or branched alkyl or fluoroalkyl group. In some embodiments, $R^2$, $R^3$, and $R^4$ are independently selected from hydrogen, fluoro and cyano. In many embodiments, $R^9$ is a $C_1$-$C_{12}$ alkyl group.

Such NDI-organotin compounds can be made by a method comprising the steps of
a. providing or obtaining a monomeric naphthalene diimide compound substituted with a leaving group LG, and having the structure;

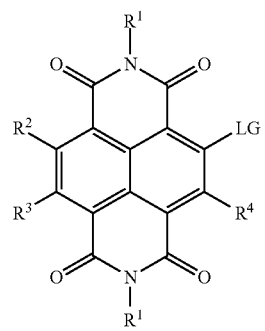

wherein LG is a halogen, such as Br or I, and
b) reacting the monomeric naphthalene diimide compound with a compound having the structure $(R^9)_3Sn$—$Sn(R^9)_3$, in the presence of a catalyst (typically soluble palladium compounds, such as the Stille coupling catalysts, i.e. $Pd_2dba_3$ and $P(o\text{-tol})_3$ ligand), and wherein $R^9$ is an alkyl or aryl group, to form at least some of the naphthalene diimide organotin compounds.

This method for making isolatable quantities of the naphthalene diimide organotin compounds is unexpected. Without wishing to be bound by theory, it was expected that under such "Stille Coupling" conditions, the naphthalene diimide organotin compounds would be formed as a reaction intermediate, but would cross couple "in-situ" in a "Stille Coupling" with another mole of the leaving group substituted NDI, to generate an NDI-NDI dimer with directly coupled NDI groups. Unexpectedly, (especially in view of differing results with related perylenediimide compounds) the anticipated "dimerization" coupling reaction of bromide substituted NDI compounds did not proceed at a significant rate, but as a result the NDI organotin compounds can be isolated in good yield and used as synthetic intermediates to make other NDI-based materials. The nucleophilic NDI organotin compounds isolated from these unexpected reactions can however be readily coupled (in the presence of various appropriate palladium coupling catalysts well known to those of ordinary skill in the art) with other (less sterically hindered) bromide-substituted heteroaryl compounds, even if the brominated heteroaryl compounds are highly electron withdrawn, and enable the practical synthesis of NDI-hAr-NDI oligomers with electron withdrawn hAr bridging groups. See for example Examples 9 and 10 below.

Organic Electronic Devices Comprising the NDI Oligomers

Some aspects of the present inventions relate to novel organic electronic devices comprising the NDI oligomers described herein, including transistors. Many variations of specific configurations of, and methods for making transistors comprising solution processable organic semiconductors are known in the art, and one of ordinary skill in the art would, in light of the prior art and the disclosures herein, be able to make a variety functional transistors comprising the NDI or PDI oligomers of the present inventions.

However, to Applicant's knowledge there is no one set of conditions or device configurations and material selections which universally leads to the best optimized performance for all possible organic semiconductor materials, and it has been found that device performance, as characterized by field effect mobility, $I_{ON}/I_{OFF}$, threshold voltages among other things, in general must be optimized for each new semiconductor material.

The organic thin film transistors of the present invention typically have a configuration such that an organic semiconductor layer including the NDI oligomers is formed, while also contacting the source electrode, drain electrode and insulating dielectric layer for the field effect gate for the transistor.

The substrate, source electrode, drain electrode, gate, etc, can be arranged geometrically in many ways, but it is also known in the art that the measured properties of the semiconductors can vary very substantially depending on the materials and geometrical arrangements of the transistor components, and their specific suitability for and compatibility with a particular organic semiconductor material.

One typical configuration of such Organic Field Effect Transistors ("OFETs") are conventional bottom-contact, bottom-gate geometries. For example, a heavily doped silicon wafer coated with a thin layer dielectric such as silicon dioxide can serve as the substrate and/or gate electrode and dielectric layer. Source and drain electrodes are patterned on top of the $SiO_2$ dielectric layer by a variety of well known techniques, and the remaining surface of the dielectric can be optionally treated with a very thin layer of a variety of known organic surface modifiers (such as organic silanes or phosphonic acids) to improve the wettability and other properties of the dielectric layer, then a layer of the organic semiconductor can be applied on top of the dielectric and electrodes, to form a "Bottom contact, bottom gate" OFET.

However, other arrangements can sometimes better match the properties and/or improve the measured performance of some individual organic semiconductors, such as the NDI oligomers described herein. Bottom gate, top contact OFETS are typically formed by processes similar to those of bottom gate, bottom contact OFETS, except that the application of source and drain electrodes is delayed, so that the source and drain electrodes are applied to the top of the semiconductor film. Example 12 provides an example of the construction of such a bottom gate-top contact OFET.

Figure 3:
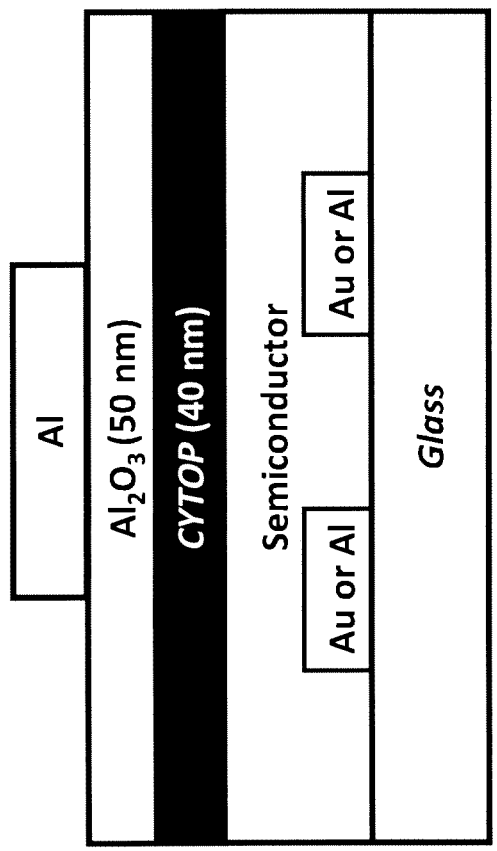
FIG. 3 shows a schematic diagram of the bottom contact top gate OFETs with a CYTOP/$Al_2O_3$ dielectric bilayer employed in some of the Examples 14-17.

Example 12 and FIG. 3 also describe "bottom contact, top gate" OFETs, including bottom contact, top gate OFETS that employ a very highly efficient top gate bilayer dielectric, comprised of CYTOP (a fluorinated organic polymer) and alumina as the dielectric. Such bottom contact, top gate OFETs, previously described and claimed by some of the current inventors of this application in U.S. Provisional Patent Application Ser. No. 61/390,408, filed 10 Oct. 2010 which is hereby incorporated by reference herein, have been found to often significantly improve the measured electrical characteristics of some of the NDI oligomer semiconductors described herein.

Various insulating materials can be used for the insulating (i.e. dielectric) layer of the gates of the OFET devices of the inventions herein. Specific examples of the insulating materials include inorganic insulating materials such as silicon oxide, silicon nitride, aluminum oxide, aluminum nitride, titanium oxide, tantalum oxide, tin oxide, vanadium oxide, barium strontium titanate, barium zirconate titanate, lead zirconium titanate, lead lanthanum titanate, strontium titanate, barium titanate, barium magnesium fluoride, bismuth tantalate niobate, hafnium oxide, and trioxide yttrium. Polymeric organic insulating materials such as e.g., polyimide, polyvinyl alcohol, polyvinyl phenol, polystyrene, polyester, polyethylene, polyphenylene sulfide, unsubstituted or halogen-atom substituted polyparaxylylene, polyacrylonitrile, and cyanoethylpullulan; etc can also be used. These materials can be used alone or in combination. Among these materials, materials having a high dielectric constant and a low conductivity are preferably used. It is common in many embodiments to use a thin layer of an inorganic material having a high dielectric constant as the primary insulting/dielectric material, but to coat the surface of the inorganic material with a very thin film of an organic material that can be compatible with both the inorganic insulating material and the organic semiconductor oligomers to be applied to the other surface of the organic thin film.

Suitable methods for forming such an insulating layer include dry processes such as CVD methods, plasma CVD methods, plasma polymerization methods, and vapor deposition methods; wet processes such as spray coating methods, spin coating methods, dipcoating methods, inkjet coating methods, castcoating methods, blade coating methods, and bar coating methods; etc.

As discussed above, in order to improve contact between the insulating layer of the gate and the organic semiconductor layer, and to reduce leakage current, an organic thin film (intermediate layer) can be employed between the insulating layer and organic semiconductor layer. The materials for use in the intermediate layer are not particularly limited as long as the materials do not significantly affect the stability or significantly decrease the desired electrical properties of the organic semiconductor layer. For example, molecular films of organic materials, and thin films of polymers can be used as the organic thin film. Specific examples of the materials for use in preparing such organic thin films include coupling agents such as octadecyltrichlorosilane, octyltrichlorosilane, octyltrimethoxysilane, hexamethyldisilazane (HMDS)), octadecylphosphonic acid, and BCB (divinyltetramethyldisiloxane-bis(benzocyclobutene)). Specific examples of the polymers for use in preparing polymer thin films include the polymers mentioned above for use in the insulating layer. Such polymer films can serve as the insulating layer as well as the intermediate layer.

The materials of the electrodes (such as gate electrodes, source electrodes and drain electrodes) of the organic thin film transistor of the present invention are not particularly limited as long as the materials are electrically conductive. Specific examples of the materials include metals such as platinum, gold, silver, nickel, chromium, copper, iron, tin, antimony, lead, tantalum, indium, aluminum, zinc, tungsten, titanium, calcium, and magnesium; alloys of these metals; electrically conductive metal oxides such as indium tin oxide (ITO); inorganic or organic semiconductors, whose electroconductivity is improved by doping or the like, such as silicon single crystal, polysilicon, amorphous silicon, germanium, graphite, carbon nanotube, polyacetylene, polyparaphenylene, polythiophene, polypyrrole, polyaniline, polythienylenevinylene, polyparaphenylenevinylene, and complexes of polyethylenedioxythiophene (PEDOT) and polystyrene sulfonic acid.

The preparation of transistors comprising the NDI oligomers of the inventions as organic semiconductors typically require the formation of a film comprising one or more of the NDI oligomers of the invention on a substrate. Organic films of the NDI oligomers can be prepared by known methods such as spin coating methods, casting methods, dip coating methods, inkjet methods, doctor blade coating methods, screen printing methods, and spray coating methods. By using such methods, it become possible to prepare organic films having good properties such as mechanical strength, toughness, and durability without forming cracks in the films. Therefore, the organic films can be preferably used for organic electronic devices such as photovoltaic cells, and transistors.

Films of the copolymer of the present inventions are typically prepared from a coating liquid, which is prepared by dissolving the copolymer in a solvent such as dichloromethane, tetrahydrofuran, chloroform, toluene, chlorobenzene, dichlorobenzene, or xylene, on a substrate for the device. Specific examples of the coating methods include spray coating methods, spin coating methods, blade coating methods, dip coating methods, cast coating methods, roll coating methods, bar coating methods, die coating methods, ink jet methods, dispense methods, etc. In this regard, a proper method and a proper solvent are selected in consideration of the solubility and other physical properties of the NDI oligomers used. Suitable materials for use as the substrate on which a film of the polymer of the present invention is formed include inorganic substrates such as glass plates, silicon plates, silicon dioxide coated silicon plates, ITO plates, and FTO plates, or organic substrates such as plastic plates (e.g., PET films, polyimide films, and polystyrene films), which can be optionally subjected to a surface treatment. It is preferable that the substrate has a low surface roughness.

The thickness of the organic film and the organic semiconductor layer of the organic thin film transistor of the present invention are not particularly limited. However, the thickness is determined such that the resultant film or layer is a uniform thin layer (i.e., the film or layer does not include gaps or holes adversely affecting the carrier transport property thereof). The thickness of the organic semiconductor layer is generally not greater than 1 micron, and preferably from 5 to 200 nm.

The organic thin film transistor prepared can be thermally annealed. Annealing is performed while the film is set on a substrate, and is believed (without wishing to be bound by theory) to allow for at least partial self-ordering and/or π-stacking of the semiconductor oligomers to occur in the solid state. The annealing temperature is determined depending on the property of the NDI-hAr-NDI oligomers, but is preferably from room temperature to 300° C., and more preferably from 50 to 300° C. In many embodiments, thermal annealing is carried out at least 150° C., or preferably above 170° C., or above 200° C. When the annealing temperature is too low, the organic solvent remaining in the organic film cannot be well removed therefrom. In contrast, when the annealing temperature is too high, the organic film can be thermally decomposed. Annealing is preferably performed in a vacuum, or under nitrogen, argon or air atmosphere. In some embodiments annealing is performed in an atmosphere including a vapor of an organic solvent capable of dissolving the polymer so that the molecular motion of the polymer is accelerated, and thereby a good organic thin film can be prepared. The annealing time is properly determined depending on the aggregation speed of the polymer.

The measurement of the properties of the OFET devices prepared and described herein were typically done in a glove box under nitrogen, using standard commercial electronic measurement instruments for the measurements, as described in the Examples below.

In some embodiments, the transistors comprising one or more of the NDI oligomers described herein are bottom gate, bottom contact transistors. In other embodiments, the transistors comprising one or more of the NDI or PDI oligomers described herein are top gate, bottom contact transistors.

In some embodiments, the transistors can be high performance ambipolar OFETs. These can be used in complementary-like circuits composed of ambipolar OFETs. The transistors can comprise solution-processed organic semiconductors. In an embodiment, the inverter comprises a top-gate OFET device geometry with the bi-layer gate dielectric. Although not bound by theory, it may be that the device geometry with the bi-layer gate dielectric allows comparatively low voltage operation with remarkable long-term environmental and operational stability of the OFETs. Example 18 provides illustrative results of these embodiments wherein the top-gate OFETs with NDI-DTP-NDI from various batches exhibit ambipolar behavior with a maximum electron mobility value of 1.5 $cm^2/Vs$ and a maximum hole mobility value of 0.01 $cm^2/Vs$ in the saturation regime. Complementary-like inverters composed of these ambipolar OFETs showed hysteresis-free voltage transfer characteristics and yielded very high DC gain values of more than 90 V/V (up to 122 V/V). Further enabling publications, which are incorporated in their entirety, relating to OFET and inverters include X.-H. Zhang, et al, *Appl. Phys. Lett.*, 94 (2009) 043312; H. Klauk, et al, *Ieee Transactions on Electron Devices*, 52 (2005) 618-622; N. Stingelin-Stutzmann, et al, *Nat. Mater.*, 4 (2005) 601-606; I. McCulloch, et al, *Nat. Mater.*, 5 (2006) 328-333; H. Minemawari, T et al, *Nature*, 475 (2011) 364-367; H. Yan, Z et al, *Nature*, 457 (2009) 679-686; A. Dodabalapur, et al, *Science*, 269 (1995) 1560-1562; C. Rost, et al, *J. Appl. Phys.*, 95 (2004) 5782-5787; H. B. Wang, et al, *Appl. Phys. Lett.*, 88 (2006) 0133508; E. Kuwahara, et al, *Chemical Physics Lett.*, 413 (2005) 379-383; T. Yasuda, et al, *Appl. Phys. Lett*, 85 (2004) 2098-2100; T. B. Singh, et al, *Adv. Mater.*, 17 (2005) 2315-2320; T. Sakanoue, et al, *Appl. Phys. Lett.*, 90 (2007) 171118; K. Tada, et al, *Jpn. J. Appl. Phys. Part 2—Lett.*, 35 (1996) L944-L946; A. Babel, et al, *Adv. Funct. Mater.*, 14 (2004) 891-898; T. D. Anthopoulos, et al, *Adv. Mater.*, 16 (2004) 2174-2179; H. Kajii, et al, *Org. Electron.*, 11 (2010) 509-513; E. J. Meijer, et al, *Nat. Mater.*, 2 (2003) 678-682; T. D. Anthopoulos, et al, *Appl. Phys. Lett.*, 85 (2004) 4205-4207; T. D. Anthopoulos, et al, *Adv. Mater.*, 18 (2006) 1900-1904; M. Shkunov, et al, *Adv. Mater.*, 17 (2005) 2608-2612; M. Chikamatsu, et al, *Appl. Phys. Lett.*, 91 (2007) 043506; L. E. Polander, et al, *Chem. of Mater.*, 23 (2011) 3408-3410; D. K. Hwang, et al, *Adv. Mater.*, 23 (2011) 1293-1298; J. B. Kim, et al, *Org. Electron.*, 11 (2010) 1074-1078.

EXAMPLES

The various inventions described above are further illustrated by the following specific examples, which are not intended to be construed in any way as imposing limitations upon the scope of the invention disclosures or claims attached herewith. On the contrary, it is to be clearly understood that resort may be had to various other embodiments, modifications, and equivalents thereof which, after reading the description herein, may suggest themselves to one of ordinary skill in the art without departing from the scope of the inventions described herein.

General

All experiments with air- and moisture-sensitive intermediates and compounds were carried out under an inert atmosphere using standard Schlenk techniques. NMR spectra were recorded on either a 300 MHz Varian Mercury spectrometer or a 400 MHz Bruker AMX 400 and referenced to residual proton solvent or tetramethyl silane. Abbreviations used in the descriptions of the spectra below include singlet (s), doublet (d), doublet of doublets (dd), triplet (t), triplet of doublets (td) and unresolved multiplet (m). Mass spectral analyses were provided by the Georgia Tech Mass Spectrometry Facility.

UV-vis absorption spectra were recorded on a Varian Cary 5E UV-vis-NIR spectrophotometer, while solution and thin-film PL spectra were recorded on a Fluorolog III ISA spectrofluorometer. Cyclic voltammograms were obtained on a computer controlled BAS 100B electrochemical analyzer, and measurements were carried out under a nitrogen flow in deoxygenated dichloromethane or tetrahydrofuran solutions of tetra-n-butylammonium hexafluorophosphate (0.1 M). Glassy carbon was used as the working electrode, a Pt wire as the counter electrode, and an Ag wire anodized with AgCl as the pseudo-reference electrode. Unless specifically noted, all reported potentials were referenced to the ferrocenium/ferrocene ($FeCp_2^{+/0}$) couple by using ferrocene as an internal standard. Differential scanning calorimetry (DSC) data were collected using a Seiko model DSC 220C. Thermal gravimetric analysis (TGA) data were collected using a Seiko model TG/DTA 320. Inductively coupled plasma-mass spectrometry (ICP-MS) for platinum and ruthenium was provided by Bodycote Testing Group. The onset of thermal degradation for the polymers was measured by thermal gravimetric analysis (TGA) using a Shimadzu TGA-50. Elemental analyses for C, H, and N were provided by Atlantic Microlabs.

Unless otherwise noted, cited reagents and solvents were purchased from well-known commercial sources (such as Sigma-Aldrich of Milwaukee Wis. or Acros Organics of Geel Belgium, and were used as received without further purification.

Example 1

Synthesis of N,N'-Bis(n-hexyl)-4-bromonaphthalene-1,4:5,8-bis(dicarboximide)

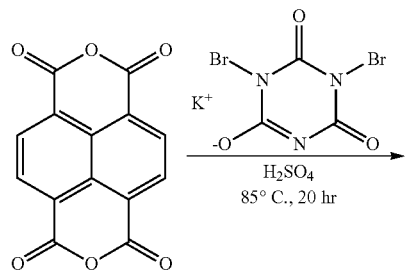

-continued

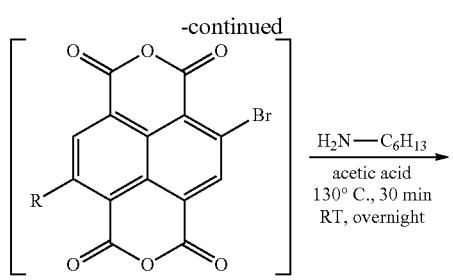

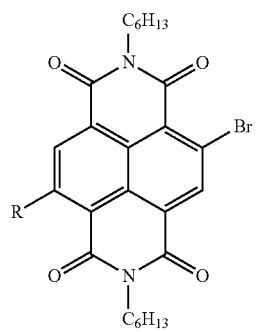

R = H, Br

A solution of naphthalene-1,4:5,8-tetracarboxydianhydride (10.0 g, 37.3 mmol) in concentrated sulfuric acid (370 mL) was heated to 85° C. Potassium 1,5-dibromo-4,6-dioxo-1,4,5,6-tetrahydro-1,3,5-triazin-2-olate (6.06 g, 18.64 mmol) was dissolved in concentrated sulfuric acid and added via cannula. The mixture was allowed to stir at 85° C. for 48 hours. After cooling, the reaction mixture was poured into ice. The resulting yellow precipitate was collected by filtration, washed with methanol, and dried under vacuum. The yellow solid was transferred to a flask with glacial acetic acid (370 mL) and n-hexylamine (15.1 g, 0.149 mol). The reaction mixture was refluxed for 20 min, allowed to cool overnight, and poured into 1500 mL of methanol. The resulting precipitate was collected by filtration, washed with methanol, and dried under vacuum. The crude product was purified by column chromatography (silica, dichloromethane) to yield a white solid (2.38 g, 4.64 mmol, 12.4%).

$^1$H NMR (400 MHz, $CDCl_3$) δ 8.88 (s, 1H), 8.77 (d, J=7.6 Hz, 1H), 8.72 (d, J=7.6 Hz, 1H), 4.16 (t, J=6.9 Hz, 2H), 4.14 (t, J=6.6 Hz, 2H), 1.71 (quint., J=7.1 Hz, 2H), 1.69 (quint., J=7.6 Hz, 2H), 1.45-1.24 (m, 12H), 0.87 (t, J=7.0 Hz, 6H). $^{13}C\{^1H\}$ NMR (100 MHz, $CDCl_3$) δ 162.40, 161.79, 161.67, 160.99, 138.3, 131.63, 130.67, 128.62, 128.54, 126.79, 125.99, 125.92, 125.64, 123.85, 41.47, 41.09, 31.46, 31.44, 27.93, 27.88, 26.76, 26.67, 22.54, 22.50, 14.02. HRMS (EI) m/z [M]$^+$ calcd for $C_{26}H_{29}BrN_2O_4$, 512.13107; found, 512.1280. Anal. Calcd. for $C_{26}H_{29}BrN_2O_4$: C, 60.82; H, 5.69; N, 5.46. Found: C, 59.91; H, 5.60; N, 5.36.

Example 2

Synthesis of 2,7-dihexyl-4-(tributylstannyl) naphthalene-1,4:5,8-bis(dicarboximide)

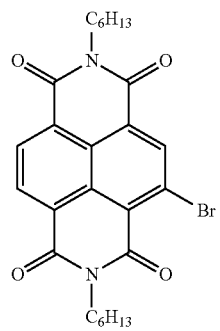

A solution of N,N'-bis(n-hexyl)-2-bromonaphthalene-1,4, 5,8-bis(dicarboximide) (1.45 g, 2.82 mmol), 1,1,1,2,2,2-hexabutyldistannane (1.64 g, 2.82 mmol), and trio-tolylphosphine (0.172 g, 0.565 mmol) in dry toluene (30 mL) was degassed with nitrogen for 5 minutes. Tris(dibenzylideneacetone)dipalladium (0.129 g, 0.141 mmol) was added and the reaction was heated to 90° C. for 24 hours. After cooling, the reaction mixture was precipitated in methanol, the solid was removed via filtration, and the solvent was removed under reduced pressure. The crude product was purified by column chromatography (silica, dichloromethane) to yield a yellow solid (2,7-dihexyl-4-(tributylstannyl) naphthalene-1,4:5,8-bis(dicarboximide), 1.53 g, 2.11 mmol, 74.9%).

$^1$H NMR (400 MHz, CDCl$_3$) δ 8.94 (s, 1H), 8.70 (d, J=7.6 Hz, 1H), 8.67 (d, J=7.6 Hz, 1H), 4.18 (t, J=7.6 Hz, 2H), 4.16 (t, J=8.0 Hz, 2H), 1.75-1.64 (m, 4H), 1.55-1.45 (m, 6H), 1.40-1.23 (m, 18 H), 1.19 (t, J=8.2 Hz, 6H), 0.90-0.80 (m, 15H). $^{13}$C{$^1$H} NMR (100 MHz, CDCl$_3$) δ 164.91, 163.62, 163.12, 163.04, 156.00, 138.65, 131.67, 130.24, 130.13, 126.84, 126.72, 126.70, 125.98, 123.64, 53.40, 41.00, 40.91, 31.50, 29.20, 28.25, 28.07, 28.02, 27.39, 26.76, 26.65, 22.54, 22.48, 17.27, 14.02, 13.69, 13.58, 11.58. HRMS (MALDI) m/z [M]$^+$ calcd for $C_{38}H_{56}N_2O_4Sn$, 725.3340; found, 725.3325. Anal. Calcd. for $C_{38}H_{56}N_2O_4Sn$: C, 63.08; H, 7.80; N, 3.87. Found: C, 62.81; H, 7.99; N, 3.93.

Example 3

Synthesis of "NDI-T-NDI": 4,4'-(thiophene-2,5-diyl) bis(2,7-dihexyl naphthalene-1,4:5,8-bis(dicarboximide))

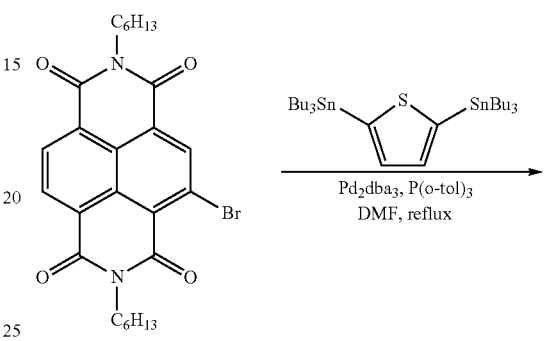

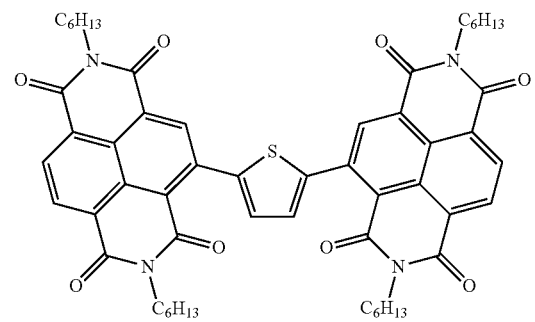

"NDI-T-NDI"

A solution of 4-bromo-2,7-dihexyl naphthalene-1,4:5,8-bis(dicarboximide) (1.00 g, 1.95 mmol), tri-o-tolylphosphine (0.056 g, 0.185 mmol), and 2,5-bis(tributylstannyl)thiophene (0.610 g, 0.930 mmol) in anhydrous dimethylformamide (20 mL) was degassed with nitrogen for 5 minutes. Tris(dibenzylideneacetone)dipalladium(0) (Pd$_2$(dba)$_3$) (0.046 g, 0.048 mmol) was added and the reaction was heated to 150° C. for 2 hours. After cooling, the reaction mixture was diluted with chloroform and washed with de-ionized water 3 times. The solution was dried with anhydrous magnesium sulfate and filtered through a plug of Celite. The crude product was purified by flash chromatography (silica gel, 2% ethyl acetate in chloroform). The product was precipitated from methanol and hexanes to yield the product as a purple solid (4,4'-(thiophene-2,5-diyl)bis(2,7-di-n-hexyl naphthalene-1,4:5,8-bis(dicarboximide)) 0.465 g, 0.490 mmol, 52.1%).

$^1$H NMR (300 MHz, CDCl$_3$) δ 8.88 (s, 2H), 8.83 (d, J=7.7 Hz, 2H), 8.77 (d, J=7.6 Hz, 2H), 7.40 (s, 2H), 4.18 (m, 8H), 1.71 (m, 8H), 1.32 (m, 26H) 0.88 (m, 12H). HRMS (MALDI) m/z [M]$^+$ calcd. for $C_{56}H_{60}N_4O_8S$ 948.4132 found 948.4096, Anal. Calcd. for $C_{56}H_{60}N_4O_8S$: C, 70.86; H, 6.37; N, 5.90. Found: C, 70.62; H, 6.33; N, 5.99.

Example 4

Synthesis of "NDI-TT-NDI": 4,4'-(thieno[3,2-b]thiophene-2,5-diyl)bis(2,7-dihexyl naphthalene-1,4:5,8-bis(dicarboximide))

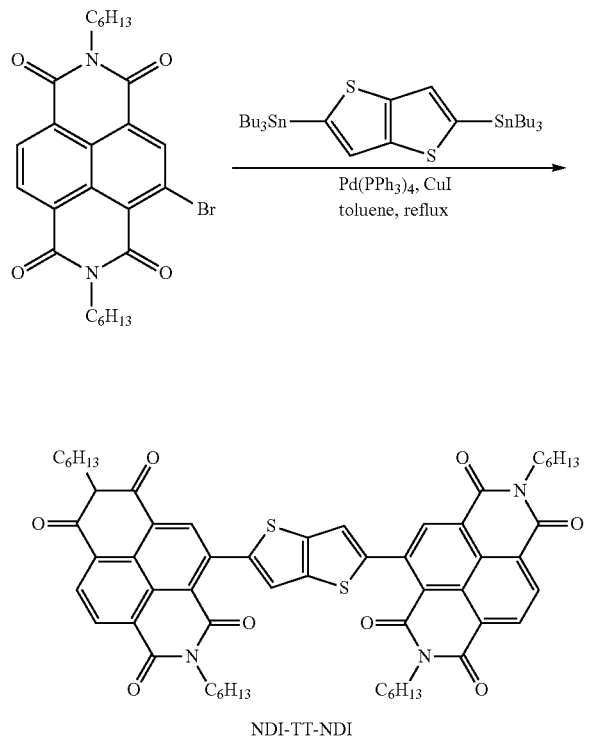

NDI-TT-NDI

A solution of 4-bromo-2,7-dihexyl naphthalene-1,4:5,8-bis(dicarboximide) (1.00 g, 1.96 mmol), 2,5-bis(tributylstannyl)thieno[3,2-b]thiophene (0.683 g, 0.951 mmol), and copper(II) iodide (0.022 g, 0.117 mmol) in dry toluene (20 mL) was degassed with nitrogen for 5 minutes. Tetrakis(triphenylphosphine)palladium (0.584 g, 0.506 mmol) was added and the reaction was heated to 90° C. for 18 hours. After cooling, the reaction mixture was diluted with dichloromethane and filtered through a plug of celite and the filtrate was concentrated via rotary evaporation. The crude product was purified by flash chromatography (silica gel, 2.0% ethyl acetate in chloroform). The product was precipitated from iso-propanol and collected as a purple solid (4,4'-(thieno[3,2-b]thiophene-2,5-diyl)bis(2,7-dihexyl naphthalene-1,4:5,8-bis(dicarboximide) 0.257 g, 0.256 mmol, 26.9%).

$^1$H NMR (300 MHz, CDCl$_3$) δ 8.84 (d, J=7.6 Hz, 2H), 8.79 (s, 2H), 8.77 (d, J=7.4 Hz, 2H), 7.51 (s, 2H), 4.27-4.05 (m, 8H), 1.81-1.63 (m, 8H), 1.50-1.25 (m, 24H), 0.96-0.83 (m, 12H). $^{13}$C NMR (100 MHz, CDCl$_3$) δ 162.69, 162.38, 162.36, 161.87, 143.22, 140.91, 140.10, 136.08, 131.51, 130.82, 127.83, 126.87, 126.57, 126.35, 125.30, 123.63, 120.60, 41.22, 41.02, 31.48, 31.46, 28.00, 26.75, 26.70, 22.55, 22.51, 14.00 (two aliphatic resonances not observed due to overlap). HRMS (MALDI) m/z [M+H]$^+$ calcd for $C_{58}H_{60}N_4O_8S_2$ 1005.392536; found, 1005.3912. Anal. Calcd. for $C_{58}H_{60}N_4O_8S_2$: C, 69.30; H, 6.02; N, 5.57. Found: C, 69.18; H, 6.06; N, 5.48.

Example 5

Synthesis of "NDI-DTT-NDI": 4,4'-(dithieno[3,2-b:2',3'-d]thiophene-2,6-diyl)bis(2,7-dihexyl naphthalene-1,4:5,8-bis(dicarboximide))

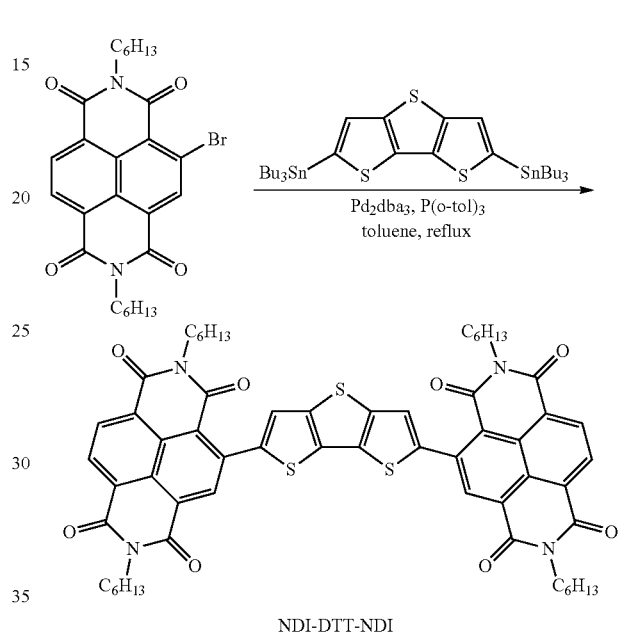

NDI-DTT-NDI

A solution of 4-bromo-2,7-dihexyl naphthalene-1,4:5,8-bis(dicarboximide) (1.50 g, 2.92 mmol), 2,6-bis(tributylstannyl)dithieno[3,2-b:2',3'-d]thiophene (1.08 g, 1.39 mmol), and trio-tolylphosphine (0.085 g, 0.278 mmol) in dry toluene (30 mL) was degassed with nitrogen for 5 minutes. Tris(dibenzylideneacetone)dipalladium (0.064 g, 0.070 mmol) was added and the reaction was heated to 90° C. for 1 hour. After cooling, the reaction mixture was precipitated in methanol. The solid was dissolved in chloroform, eluted through a plug of silica gel (dichloromethane:methanol), and concentrated via rotary evaporation. The crude product was purified by column chromatography (silica, 1.0% ethyl acetate in chloroform) followed by precipitation in methanol to yield a purple solid (4,4'-(dithieno[3,2-b:2',3'-d]thiophene-2,6-diyl)bis(2,7-dihexyl naphthalene-1,4:5,8-bis(dicarboximide)) 0.744 g, 0.701 mmol, 50.3%).

$^1$H NMR (400 MHz, CDCl$_3$) δ 8.80 (d, J=7.6 Hz, 2H), 8.77 (s, 2H), 8.73 (d, J=7.7 Hz, 2H), 7.52 (s, 2H), 4.17 (t, J=7.4 Hz, 4H), 4.11 (t, J=7.5 Hz, 4H), 1.77-1.60 (m, 8H), 1.46-1.23 (m, 24H), 0.93-0.77 (m, 12H). $^{13}$C{$^1$H} NMR (100 MHz, CDCl$_3$) 162.62, 162.34, 162.32, 161.84, 141.91, 141.84, 139.76, 135.98, 132.80, 131.48, 130.74, 127.82, 126.79, 126.48, 126.27, 125.24, 123.45, 121.87, 41, 16, 20.95, 31.41, 27.94, 26.70, 26.64, 22.51, 22.46, 13.96 (three aliphatic resonances not observed due to overlapping resonances). HRMS (MALDI) m/z [M+H]$^+$ calcd for $C_{60}H_{60}N_4O_8S_3$, 1060.3573;

found, 1060.3504. Anal. Calcd. for $C_{60}H_{60}N_4O_8S_3$: C, 67.90; H, 5.70; N, 5.28. Found: C, 67.69; H, 5.60; N, 5.26.

Example 6

Synthesis of "NDI-DTP-NDI": 4,4'-(4-hexyl-4H-dithieno[3,2-b:2',3'-d]pyrrole-2,6-diyl)bis(2,7-dihexyl naphthalene-1,4:5,8-bis(dicarboximide))

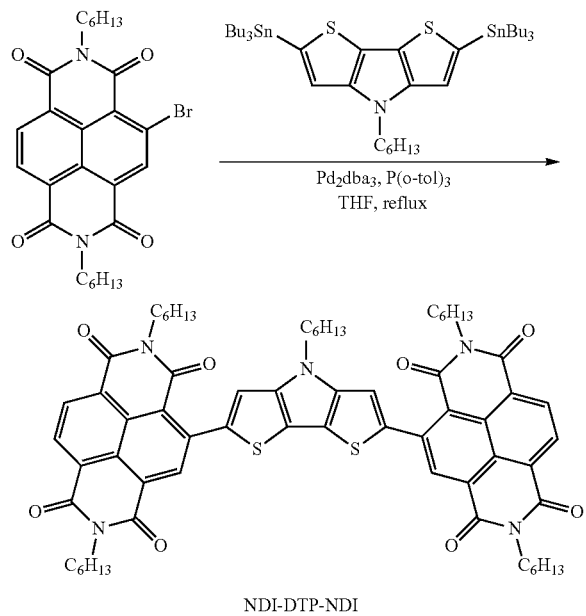

NDI-DTP-NDI

A solution of N,N'-bis(n-hexyl)-2-bromonaphthalene-1,4,5,8-bis(dicarboximide) (0.577 g, 1.12 mmol), 4-hexyl-2,6-bis(tributylstannyl)-4H-dithieno[3,2-b:2',3'-d]pyrrole (0.450 g, 0.535 mmol), and trio-tolylphosphine (0.033 g, 0.107 mmol) in dry THF (10 mL) was degassed with nitrogen for 5 minutes. Tris(dibenzylideneacetone)dipalladium (0.024 g, 0.027 mmol) was added and the reaction was heated to reflux for 18 hours. After cooling, the reaction mixture was quenched with water, extracted with chloroform, and dried over anhydrous magnesium sulfate. The combined organic washes were filtered through a plug of silica gel eluting with chloroform and concentrated via rotary evaporation. The crude product was purified by column chromatography (silica, dichloromethane) followed by precipitation in methanol to yield a dark blue solid (4,4'-(4-hexyl-4H-dithieno[3,2-b:2',3'-d]pyrrole-2,6-diyl)bis(2,7-dihexyl naphthalene-1,4:5,8-bis(dicarboximide)) 0.355 g, 0.315 mmol, 58.9%).

1H NMR (400 MHz. CDCl$_3$) δ (8.76 (s, 2H), 8.74 (d, J=7.7 Hz, 2H), 8.65 (d, J=7.7 Hz, 2H), 7.34 (s, 2H), 4.24 (t, J=7.0 Hz, 2H), 4.19-4.06 (m, 8H), 1.96 (quint., J=7.6, 2H), 1.77-1.62 (m, 8H), 1.48-1.20 (m, 30 H), 0.94-0.80 (m, 15H). 13C{1H} NMR (100 MHz, CDCl3) δ 162.70, 162.54, 162.45, 162.05, 145.52, 141.17, 139.30, 136.28, 131.25, 130.19, 128.12, 126.61, 126.34, 125.78, 124.73, 122.42, 118.34, 112.99, 41.20, 40.94, 31.52, 31.48, 31.47, 30.46, 28.01, 27.99, 26.86, 26.78, 26.70, 22.57, 22.53, 22.51, 14.02 (three aliphatic carbon signals are not observed due to overlapping resonances). HRMS (MALDI) m/z [M+H]+ calcd for $C_{66}H_{73}N_5O_8S_2$, 1128.4978; found, 1128.4761. Anal. Calcd. for C66H73N5O8S2: C, 70.25; H, 6.52; N, 6.21. Found: C, 69.99; H, 6.45; N, 6.22.

Example 7

Synthesis of "NDI-BDT-NDI"; 4,4'-(4,8-bis(hexyloxy)benzo[1,2-b:4,5-b']dithiophene-2,6-diyl)bis(2,7-dihexyl naphthalene-1,4:5,8-bis(dicarboximide))

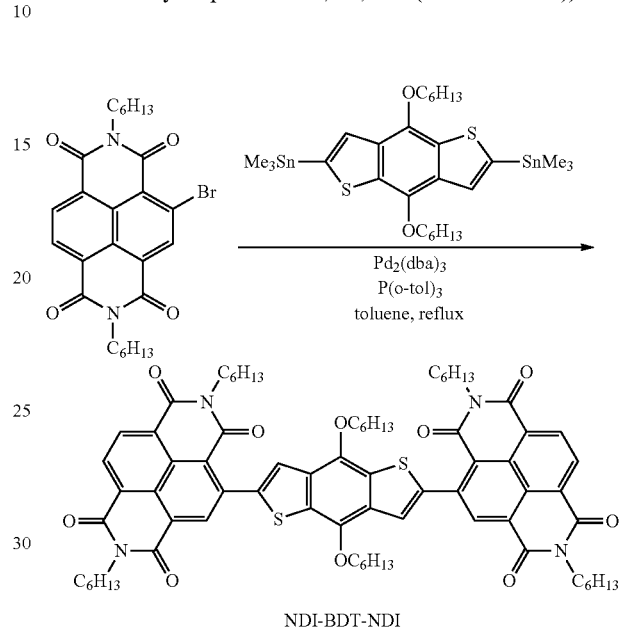

NDI-BDT-NDI

A solution of 4-bromo-2,7-dihexyl naphthalene-1,4:5,8-bis(dicarboximide) (1.30 g, 2.53 mmol), (4,8-bis(hexyloxy)benzo[1,2-b:4,5-b]dithiophene-2,6-diyl)bis(trimethylstannane) (0.860 g, 1.21 mmol), and trio-tolylphosphine (0.073 g, 0.241 mmol) in dry toluene (25 mL) was degassed with nitrogen for 5 minutes. Tris(dibenzylideneacetone) dipalladium (0.055 g, 0.060 mmol) was added and the reaction was heated to 90° C. for 3 hours. After cooling, the reaction mixture was precipitated in methanol. The solid was dissolved in chloroform, eluted through a plug of silica gel (dichloromethane:methanol), and concentrated via rotary evaporation. The crude product was purified by column chromatography (silica, 0.5% ethyl acetate in chloroform) followed by precipitation in methanol to yield a brown solid (4,4'-(4,8-bis(hexyloxy)benzo[1,2-b:4,5-b]dithiophene-2,6-diyl)bis(2,7-dihexylnaphthalene-1,4:5,8-bis(dicarboximide)), 1.04 g, 0.828 mmol, 68.9%).

$^1$H NMR (400 MHz, CDCl$_3$) δ 8.82 (s, 2H), 8.81 (d, J=7.7 Hz, 2H), 8.75 (d, J=7.6 Hz, 2H), 7.51 (s, 2H), 4.29 (t, J=6.6 Hz, 4H), 4.19 (t, J=7.6 Hz, 4H), 4.11 (t, J=7.7 Hz, 4H), 1.83 (quint., J=7.1 Hz, 4H), 1.78-1.63 (m, 8H), 1.51 (quint., J=7.4 Hz, 4H), 1.45-1.23 (m, 32H), 0.91-0.79 (m, 18H). $^{13}$C{$^1$H} NMR (100 MHz, CDCl$_3$) δ 162.63, 162.41, 162.37, 161.54, 144.55, 141.07, 140.15, 135.62, 131.93, 131.43, 130.85, 130.69, 127.61, 126.79, 126.42, 126.37, 125.18, 124.04, 120.89, 77.15, 74.04, 41.12, 41.00, 31.56, 31.44, 30.47, 27.93, 26.69, 26.67, 25.62, 22.52, 22.48, 13.97, 13.95 (three aliphatic resonances not observed due to overlapping resonances). HRMS (MALDI) m/z [M+H]$^+$ calcd for $C_{74}H_{86}N_4O_{10}S_2$, 1254.5785; found, 1254.5805. Anal. Calcd. for $C_{74}H_{86}N_4O_{10}S_2$: C, 70.78; H, 6.90: N, 4.46. Found: C, 70.64; H, 6.80; N, 4.50.

Example 8

Synthesis of "NDI-DTO-NDI": 4,4'-(4-oxo-4,1-cyclopenta[1,2-b:5,4-b']dithiophene-2,6-diyl)bis(2,7-dihexyl naphthalene-1,4:5,8-bis(dicarboximide))

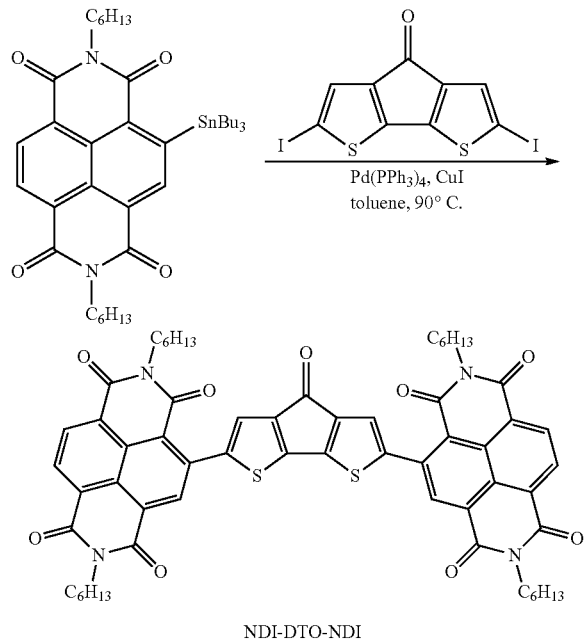

NDI-DTO-NDI

A solution of 2,7-dihexyl-4-(tributylstannyl)naphthalene-1,4:5,8-bis(dicarboximide) (0.500 g, 0.691 mmol), 2,6-diiodo-4H-cyclopenta[1,2-b:5,4-b']dithiophen-4-one (0.150 g, 0.340 mmol), and copper(II) iodide (0.006 g, 0.034 mmol) in dry toluene (7 mL) was degassed with nitrogen for 5 minutes. Tetrakis(triphenylphosphine)palladium (0.019 g, 0.017 mmol) was added and the reaction was heated to 90° C. for 3 hours. After cooling, the reaction mixture was precipitated in methanol. The solid was dissolved in chloroform, eluted through a plug of silica gel (chloroform:methanol), and concentrated via rotary evaporation. MALDI-MS m/z [M+H]$^+$ calcd for $C_{74}H_{86}N_4O_{10}S_2$, 1057.38; found, 1057.3.

Example 9

Synthesis of 4,4'-(5-oxo-5H-spiro[benzo[1,2-b:6,5-b']dithiophene-4,2'-[1,3]-dioxolane]-2,7-diyl)bis(2,7-dihexylnaphthalene-1,4:5,8-bis(dicarboximide))

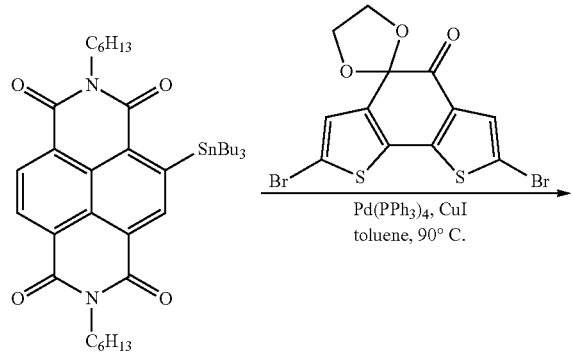

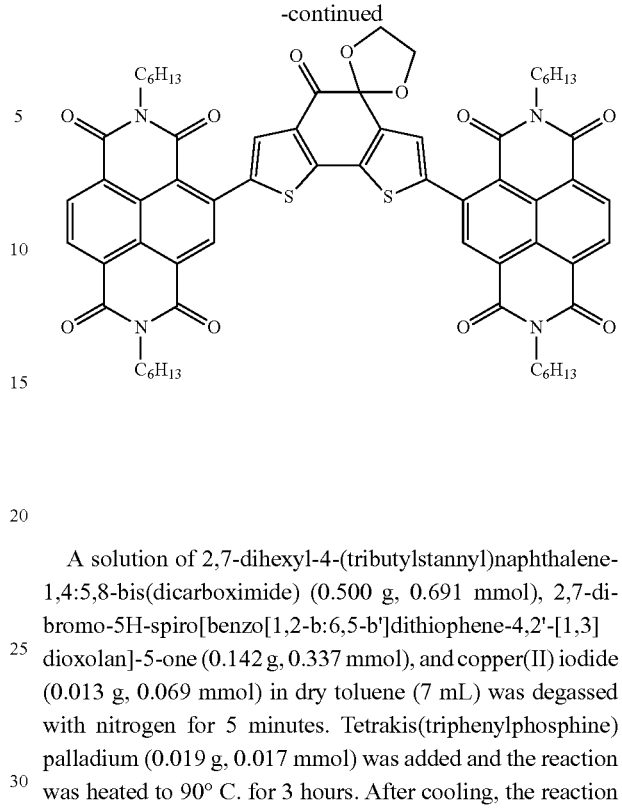

A solution of 2,7-dihexyl-4-(tributylstannyl)naphthalene-1,4:5,8-bis(dicarboximide) (0.500 g, 0.691 mmol), 2,7-dibromo-5H-spiro[benzo[1,2-b:6,5-b']dithiophene-4,2'-[1,3] dioxolan]-5-one (0.142 g, 0.337 mmol), and copper(II) iodide (0.013 g, 0.069 mmol) in dry toluene (7 mL) was degassed with nitrogen for 5 minutes. Tetrakis(triphenylphosphine) palladium (0.019 g, 0.017 mmol) was added and the reaction was heated to 90° C. for 3 hours. After cooling, the reaction mixture was precipitated in methanol. The solid was dissolved in dichloromethane, eluted through a plug of silica gel (dichloromethane:methanol), and concentrated via rotary evaporation. The crude product was purified by column chromatography (silica, 3% ethyl acetate in dichloromethane) to yield a purple solid (4,4'-(5-oxo-5H-spiro[benzo[1,2-b:6,5-b']dithiophene-4,2'-[1,3]dioxolane]-2,7-diyl)bis(2,7-dihexylnaphthalene-1,4:5,8-bis(dicarboximide)), 0.197 g, 0.174 mmol, 51.6%).

$^1$H NMR (400 MHz, CDCl$_3$) δ 8.80 (dd, J=7.8, 2.2 Hz, 2H), 8.75 (dd, J=7.6, 2.0 Hz, 2H), 8.73 (s, 1H), 8.68 (s, 1H), 7.56 (s, 1H), 7.37 (s, 1H), 4.53 (m, 2H), 4.36 (m, 2H), 4.17 (t, J=7.4 Hz, 4H), 4.11 (m, 4H), 1.78-1.62 (m, 8H), 1.46-1.20 (m, 24H), 0.92-0.80 (m, 12H). $^{13}$C{$^1$H} NMR (100 MHz, CDCl$_3$) δ 190.25, 162.61, 162.58, 162.34, 162.26, 162.23, 162.20, 161.88, 161.83, 146.22, 141.85, 139.72, 139.62, 138.80, 138.30, 135.70, 135.61, 134.04, 132.01, 131.69, 131.63, 131.04, 130.95, 128.89, 128.86, 128.85, 127.75, 127.71, 126.80, 126.58, 126.56, 126.45, 125.72, 125.55, 123.70, 123.51, 99.49, 66.17, 41.24, 41.21, 41.03, 41.01, 31.44, 27.96, 26.71, 26.66, 22.52, 22.49, 14.00 (one aliphatic resonance not observed due to overlapping resonances). HRMS (MALDI) m/z [M+H]$^+$ calcd for $C_{64}H_{64}N_4O_{11}S_2$, 1129.4091; found, 1129.4045. Anal. Calcd. for $C_{64}H_{64}N_4O_{11}S_2$: C, 68.06; H, 5.71; N, 4.96. Found: C, 68.02; H, 5.71; N, 4.86.

Example 10

Synthesis of "NDI-BDTO-NDI": 4,4'-(4,5-dioxo-4,5-dihydrobenzo[1,2-b:6,5-b']dithiophene-2,7-diyl)bis(2,7-dihexylnaphthalene-1,4:5,8-bis(dicarboximide))

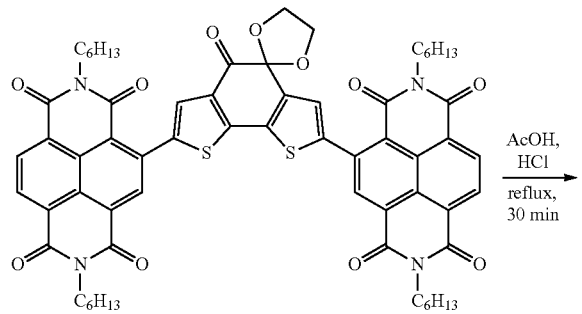

AcOH, HCl
reflux, 30 min

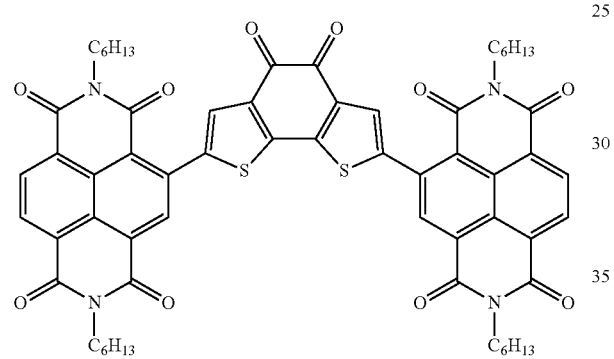

NDI-BDTO-NDI

A solution of 4,4'-(5-oxo-5H-spiro[benzo[1,2-b:6,5-b']dithiophene-4,2'-[1,3]dioxolane]-2,7-diyl)bis(2,7-dihexylnaphthalene-1,4:5,8-bis(dicarboximide) (0.150 g, 0.133 mmol), acetic acid (25 mL), and concentrated hydrochloric acid (5 mL) was degassed with nitrogen for 10 minutes. The reaction was heated to reflux for 2 hours. After cooling, the reaction mixture was diluted with water to precipitate a purple solid. The solid was filtered, washed with water and methanol, and dried under vacuum. The crude product was purified by column chromatography (silica, 3% ethyl acetate in dichloromethane) followed by precipitation in methanol to yield a purple solid (4,4'-(4,5-dioxo-4,5-dihydrobenzo[1,2-b:6,5-b']dithiophene-2,7-diyl)bis(2,7-dihexylnaphthalene-1,4:5,8-bis(dicarboximide)), 0.094 g, 0.087 mmol, 65.1%).

$^1$H NMR (400 MHz, CDCl$_3$) δ 8.82 (d, J=7.6 Hz, 2H), 8.77 (d, J=7.6 Hz, 2H), 8.67 (s, 2H), 7.62 (s, 2H), 4.15 (t, J=7.6 Hz, 4H), 4.10 (t, J=7.6 Hz, 4H), 1.76-1.63 (m, 8H), 1.45-1.23 (m, 24H), 0.90-0.78 (m, 12H). $^{13}$C{$^1$H} NMR (100 MHz, CDCl$_3$) δ 173.93, 162.37, 162.05, 162.04, 161.85, 144.52, 141.86, 137.26, 135.54, 135.07, 131.88, 131.36, 128.04, 127.56, 126.75, 126.70, 126.58, 125.82, 124.07, 41.25, 41.02, 31.38, 27.90, 26.67, 26.61, 22.49, 22.45, 13.95 (three aliphatic resonances not observed due to overlapping resonances). HRMS (MALDI) m/z [M+H]$^+$ calcd for C$_{62}$H$_{60}$N$_4$O$_{10}$S$_2$, 1085.3829; found, 1085.3790. Anal. Calcd. for C$_{62}$H$_{60}$N$_4$O$_{10}$S$_2$: C, 68.61; H, 5.57; N, 5.16. Found: C, 68.64; H, 5.56; N, 5.18.

Example 11

Synthesis of "NDI-BTDI-NDI": 4,4'-(5,5'-di-n-octyl-4,4',6,6'-tetraoxo-5,5',6,6'-tetrahydro-4H,4'H-[1,1'-bithieno[3,4-c]pyrrole]-3,3'-diyl)bis(2,7-di-n-hexyl-benzo[lmn][3,8]phenanthroline-1,3,6,8(2H,7H)-tetraone)

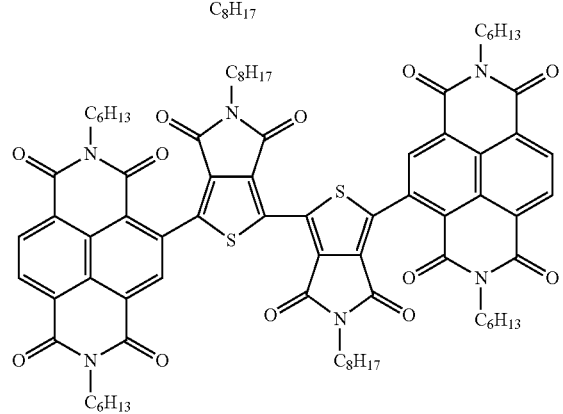

NDI-BTDI-NDI

A solution of 3,3'-dibromo-5,5'-di-n-octyl-4H,4'H-[1,1'-bithieno[3,4-c]pyrrole]-4,4',6,6'(5H,5'H)-tetraone (0.25 g, 0.36 mmol), 2,7-di-n-hexyl-4-(tributylstannyl)benzo[lmn][3,8]phenanthroline-1,3,6,8(2H,7H)-tetraone (0.54 g, 0.74 mmol), and copper(II) iodide (0.014 g, 0.073 mmol) in DMF (7.5 mL) was degassed with nitrogen for 5 minutes. Tetrakis(triphenylphosphine)palladium (0.042 g, 0.036 mmol) was added and the reaction mixture was heated to 150° C. under nitrogen for 30 minutes. After cooling, the reaction mixture was dropped into methanol (100 mL), red color precipitate was collected by filtration. The crude product was passed through an alumina-gel plug (75:25 v/v dichloromethane: hexanes) to afford an orange solid, which was further subjected to size-exclusion chromatography (THF) to give pure product. Yield: 0.41 g (78%).

$^1$H NMR (300 MHz, CDCl$_3$): δ 8.86 (d, J=7.5 Hz, 2H), 8.82 (d, J=7.5 Hz, 2H), 8.76 (s, 2H), 4.21 (t, J=7.2 Hz, 4H), 4.08 (t, J=7.2 Hz, 4H), 3.57 (t, J=7.2 Hz, 4H), 1.81-1.58 (m, 12H), 1.50-1.180 (m, 44H), 0.94-0.78 (m, 18H). $^{13}$C{$^1$H} NMR (100 MHz, CDCl$_3$) 162.47, 162.38, 162.10, 162.03, 161.99, 161.87, 142.50, 134.17, 133.66, 133.49, 133.19, 132.47, 131.89, 131.72, 127.49, 127.09, 126.95, 126.66, 125.84, 125.36, 41.35, 41.09, 38.75, 31.74, 31.52, 31.47, 29.11, 29.08, 28.40, 27.98, 27.94, 26.89, 26.75, 26.69, 22.55, 22.52, 14.02 (Three aliphatic resonances were not observed due to overlapping resonances). HRMS (MALDI) m/z [M+H]$^+$ calc for 1393.6287; found, 1393.6147. Anal. Calcd. for C$_{80}$H$_{92}$N$_6$O$_{12}$S$_2$: C, 68.94; H, 6.65; N, 6.03. Found: C, 68.93; H, 6.47; N, 5.93.

Example 12

Synthesis of "NDI-BTTZ-NDI": 4,4'-(5,5'-(1,2,4,5-tetrazine-3,6-diyl)bis(thiophene-5,2-diyl))bis(2,7-dihexylbenzo[lmn][3,8]phenanthroline-1,3,6,8(2H,7H)-tetraone)

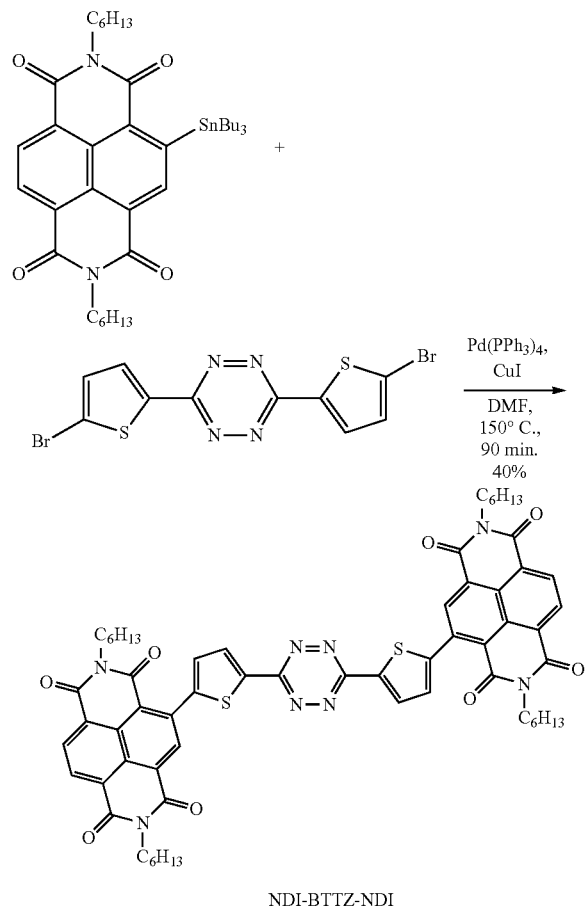

NDI-BTTZ-NDI

A solution of 3,6-bis(5-bromothiophen-2-yl)-1,2,4,5-tetrazine (0.20 g, 0.49 mmol), 2,7-di-n-hexyl-4-(tributylstannyl)benzo[lmn][3,8]phenanthroline-1,3,6,8(2H,7H)-tetraone (0.73 g, 1.01 mmol), and copper(II) iodide (0.019 g, 0.099 mmol) in DMF (6.5 mL) was degassed with nitrogen for 5 minutes. Tetrakis(triphenylphosphine)palladium (0.057 g, 0.049 mmol) was added and the reaction mixture was heated to 150° C. under nitrogen for 90 minutes. After cooling, the reaction mixture was dropped into methanol (100 mL), and red precipitate was collected by filtration. The crude product was purified by column chromatography (silica, 2% ethyl acetate in chloroform). Yield: 0.18 g (40%)+ impure fractions.

$^1$H NMR (300 MHz, CDCl$_3$): δ 8.84 (d, J=7.4 Hz, 2H), 8.80 (d, J=7.4 Hz, 2H), 8.77 (s, 2H), 8.36 (d, J=3.6 Hz, 2H), 7.35 (d, J=3.9 Hz, 2H), 4.18 (t, J=6.5 Hz, 4H), 4.09 (t, J=6.5 Hz, 4H), 1.80-1.1.61 (m, 8H), 1.38-1.26 (m, 24H), 0.89-0.81 (m, 12H). $^{13}$C{$^1$H} NMR (75 MHz, 1,1,2,2-tetrachloroethane-d$_2$, 60° C.): δ 162.38, 162.09, 162.05, 161.61, 161.22, 148.04, 138.71, 137.38, 135.07, 131.49, 131.05, 130.95, 129.87, 127.63, 126.80, 126.50, 126.48, 125.46, 124.03, 41.09, 40.95, 31.30, 31.26, 27.87, 27.86, 26.60, 26.53, 22.38, 22.34, 13.85, 13.83. HRMS (MALDI) m/z [M+H]$^+$ calc for 1111.413; found, 1111.420. Anal. Calcd. for C$_{62}$H$_{62}$N$_8$O$_8$S$_2$: C, 67.01; H, 5.62; N, 10.08. Found: C, 66.85; H, 5.47; N, 10.03.

Example 13

Spectra and Physical Data for Compounds Synthesized

Figure 1B:
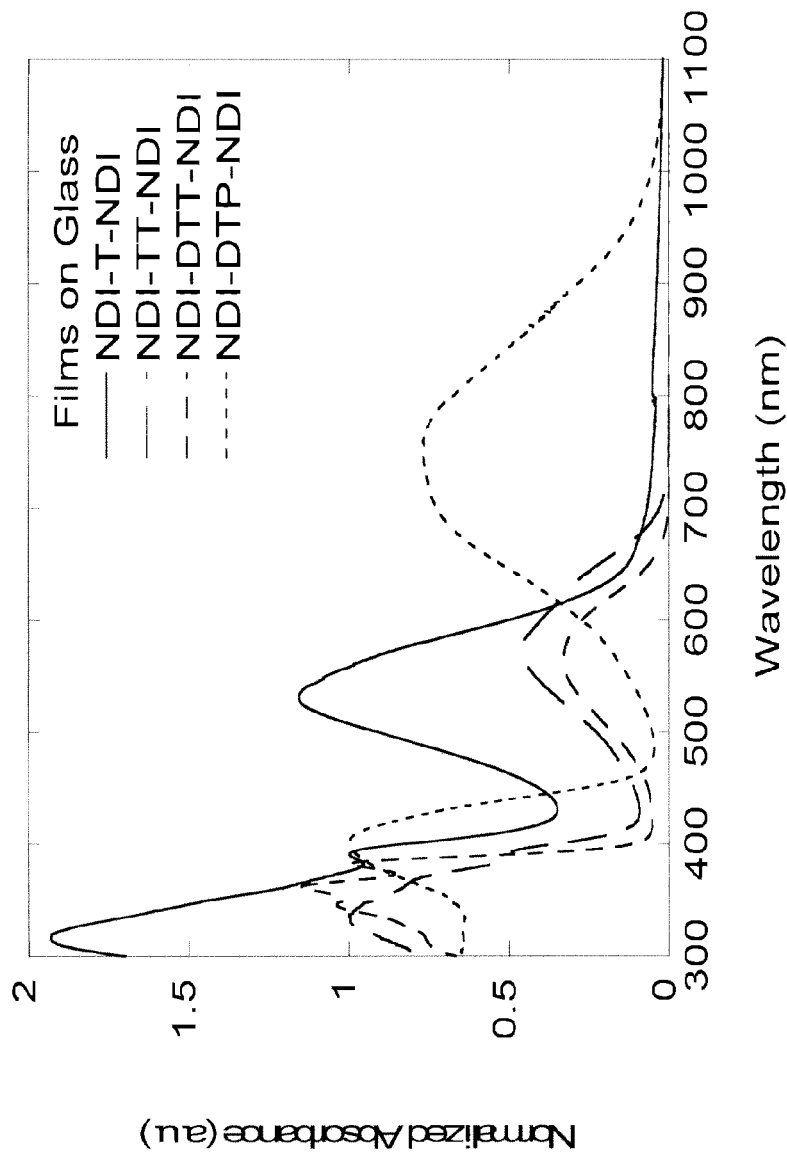
FIG. 1b shows UV-vis absorption of the same NDI-X-NDI bridged trimers in as films on glass substrates.
Figure 1C:
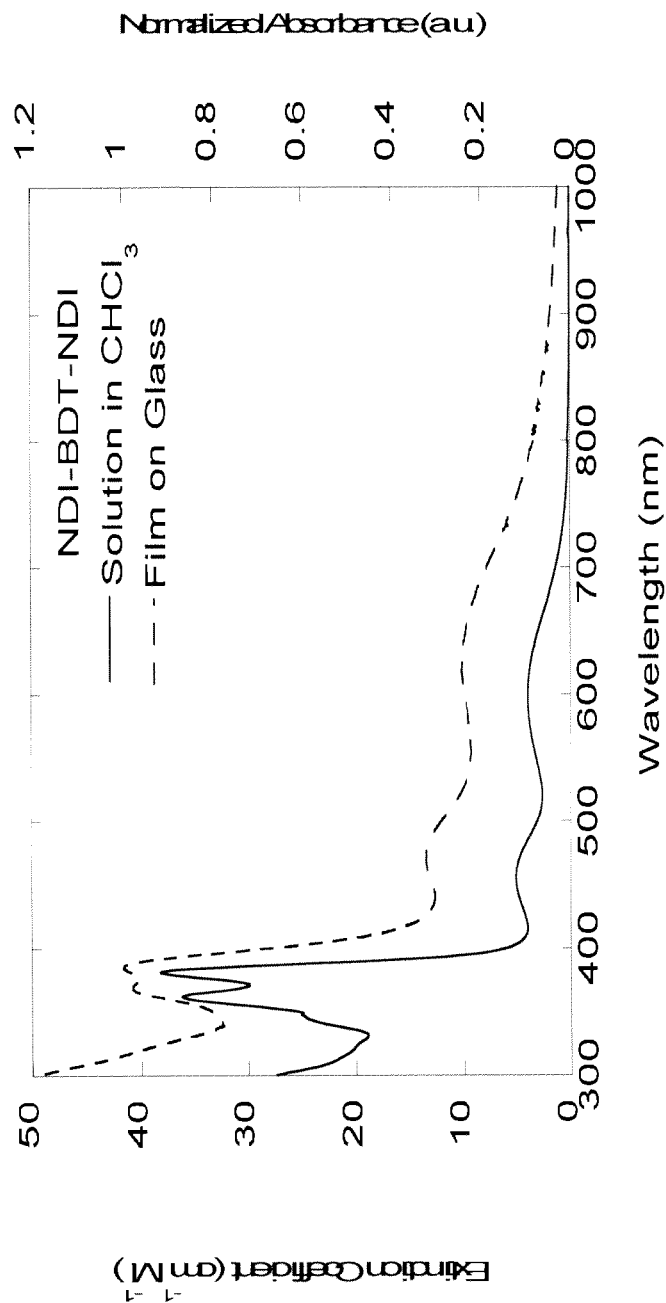
FIG. 1c shows UV-vis absorption of NDI-BTD-NDI in chloroform and as a film on glass.
Figure 1D:
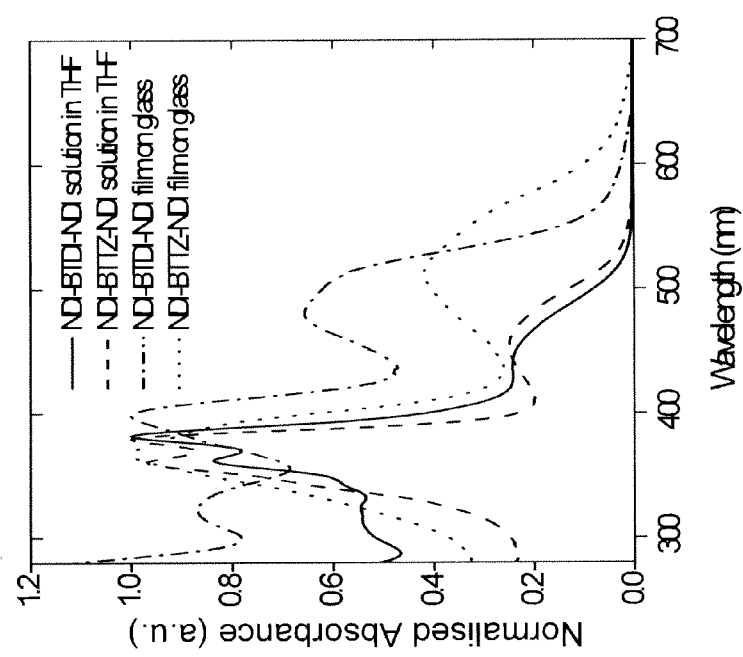
FIG. 1d shows UV-vis absorption of NDI-BTDI-NDI and NDI-BTTZ-NDI in chloroform and in THF, and as a film on glass. See Examples 3, 4, 6, 7, 11, 12, and 13.

UV-visible absorption spectra were recorded both in solution and as solid films for many of the exemplary molecules described in the examples above. A numerical summary is presented in Table 2 below, and exemplary spectra are shown in FIGS. 1a, 1b, and 1c.

TABLE 2

Summary of UV-vis absorption data for NDI-based oligomers.

| Structure | X | $\lambda_{max}$ (nm) [ε × 10$^3$ (cm$^{-1}$M$^{-1}$)] CHCl$_3$ | $\lambda_{max}$ (nm) Film |
|---|---|---|---|
| NDI-X-NDI | T | 382 (29.8), 487 (9.13) | 314, 391, 530 |
| | TT | 383 (41.7), 543 (12.8) | 335, 572 |
| | DTT | 382 (40.5), 566 (14.8) | 362, 570 |
| | DTP | 385 (52.9), 681 (19.9) | 400, 744 |
| | BDT | 381 (34.5), 455 (5.24), 601 (4.07) | 385, 474, 635 |
| | DTO | 311, 381, 568 | Not Measured |
| | BDTO | 313, 383 (34.9), 497 (10.7) | 326, 385, 517 |
| | BTDI* | 362, 382, 442 | 380, 398, 481 |
| | BTTZ* | 361, 379, 454 | 368, 384, 513 |

*spectrum measured in THF

Actual UV Visible absorption spectra of NDI-T-NDI, NDI-TT-NDI, NDI-DTT-NDI, NDI-DTP-NDI, NDI-BDTI-NDI, and NDI-BTTZ-NDI, in solution or as films on a glass surface, can be seen in FIGS. 1a-d.

Cyclic voltammetry data was also obtained for the compounds and it is shown below in Table 3. The first reduction potentials of the different compounds are all quite similar, averaging around −1.0 V to −1.1 V. The oxidation potentials, however, show a broad range.

TABLE 3

Summary of CV data for NDI-based oligomers.

| Structure | X | $E_{1/2}^{+/0}$ (V) | $E_{1/2}^{0/2-}$ (V) | $E_{1/2}^{2-/4-}$ (V) |
|---|---|---|---|---|
| NDI-X-NDI | — | N/A | −1.03, −1.18 | −1.63, −1.79 |
| | T | N/A | −1.08 | −1.49, −1.58 |
| | TT | 1.10 | −1.05 | −1.47 |
| | DTT | 0.93 | −1.03 | −1.45 |
| | DTP | 0.56 | −1.09 | −1.50 |
| | BDT | 0.50 (irrev.) | −1.02 | −1.45 |
| | DTO | Not Measured | −1.05 | −1.45 (2−/5−) |
| | BDTO | N/A | −0.91, −1.03 | −1.09, −1.51 (3−/6−) |
| | BTDI | N/A | −0.98 | −1.45, −2.02 |
| | BTTZ | N/A | −1.01 | −1.37, −1.60 |

Thermogravimetric analysis (TGA) was used to investigate the decomposition temperature of the compounds synthesized. Table 4 shows that each compound showed a decomposition temperature around and above 400° C. except for the BDT derivative (Td=336° C.). These are very high temperatures for decomposition and suggest a thermally stable material.

TABLE 4

Summary of decomposition temperatures determined using TGA for NDI2-D/π oligomers.

| Structure | X | $T_d$ (° C.) |
|---|---|---|
| NDI-X-NDI | TT | 400 |
| | DTT | 402 |
| | DTP | 409 |
| | BDT | 336 |
| | BTDI | 437 |

Example 14

Solution Processed OFETs Comprising NDI-DTP-NDI

Current-voltage (I-V) characteristics of the OFETs described herein were measured in a $N_2$-filled glove box ($O_2$, $H_2O$<0.1 ppm) with an Agilent E5272A source/monitor unit. Output ($I_{DS}$-$V_{DS}$) and transfer ($I_{DS}$-$V_{GS}$) characteristics were measured. Field-effect mobility values ($\mu$) and threshold voltages ($V_{TH}$) were measured in the saturation regime from the saturation region current equation of standard MOSFET, using highest slope of $|I_{DS}|^{1/2}$ vs. $V_{GS}$ plot.

$$I_{DS} = \frac{1}{2}\mu C_i \frac{W}{L}(V_{GS} - V_{TH})^2$$

where $C_i$ is the capacitance per unit area of the gate dielectric [F/cm$^2$], and W (width) and L (length) are the dimensions of the semiconductor channel defined by the source and drain electrodes of the transistor.

Bottom Gate, Top Contact OFETs

Preliminary testing was carried out on bottom gate, top contact OFETs constructed on substrates comprising heavily doped n$^+$-Si wafers with 200 nm of thermally grown $SiO_2$ as the gate dielectric ("insulating") layer, as are well known in the art. The substrates were cleaned by $O_2$ plasma for 3 minutes and subsequently coated with spin cast BCB (divinyltetramethyldisiloxane-bis(benzocyclobutene)), 1:20 in Trimethylbenzene, and annealed 250° C. for 1 hour) prior to semiconductor layer formation. A thin film of the NDI-DTP-NDI was spun cast from 20 mg/mL solutions in chlorobenzene, at spin speeds of 1000 rpm for 60 s. Calcium covered by gold contacts with thicknesses of 40/60 nm, respectively, were deposited as the source (S) and drain (D) electrodes through a shadow mask. The S-D channel width (W) and length (L) were 1200 μm and 25 μm, respectively.

Figures 2A, 2B:
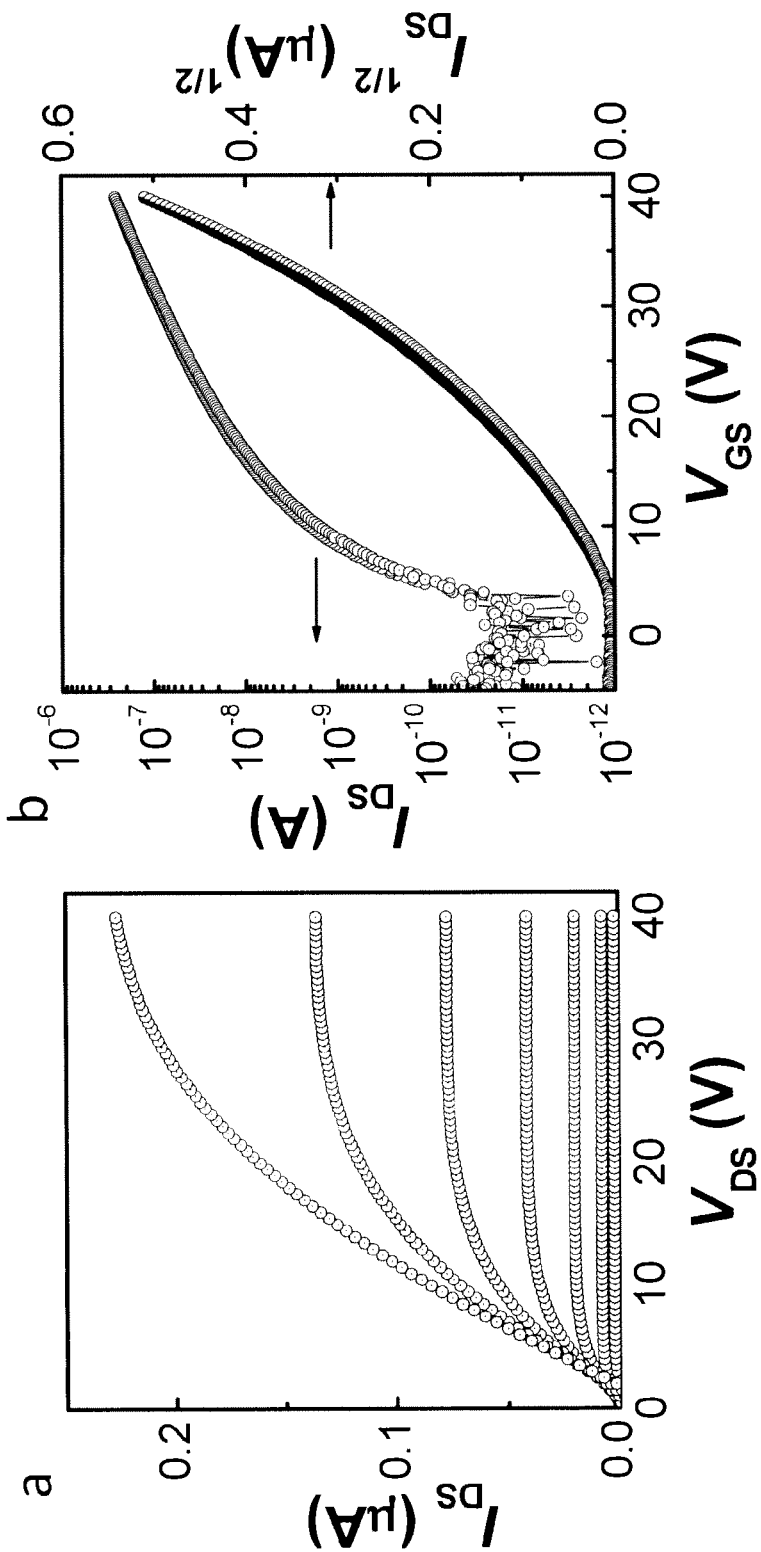
FIGS. 2a and 2b show Output (2a) and Transfer (2b) characteristics for NDI-DTP-NDI in bottom gate top contact OFET devices fabricated on n-doped Si substrate with BCB coated $SiO_2$ dielectric and Ca/Au electrodes. See Example 14.

Preliminary device measurements with this configuration showed only n-channel mobility of about 0.001 cm$^2$/Vs, with current $I_{ON}/I_{OFF}$ ratios on the order of 10$^4$, and threshold voltages of about 13.6 Volts. Measured output and transfer characteristics for the bottom gate top contact OFETs so produced are shown in FIG. 2. The output curves show the plots for $V_{GS}$ varying from 0 to 40 V in 5 V step. The transfer curve is measured in saturation regime ($V_{DS}$=40 V)

Bottom Contact, Bilayer-Topgate OFETs Comprising NDI-DTP-NDI:

In view of promising initial results with the bottom gate top contact OFETs described above, additional OFET devices with bottom contact and top gate structure (with an CYTOP/Alumina bilayer dielectric) were fabricated on glass substrates.

A schematic diagram of the physical structure of such OFETs is shown in FIG. 3. These OFETs were fabricated on glass substrates, and Au (~50 nm) or Al (~50 nm) bottom contact source/drain electrodes were deposited by thermal evaporation through a shadow mask. Thin films of the organic semiconductors were deposited by spin coating with a 30 mg/ml solution prepared from dichlorobenzene (DCB) at 500 rpm for 10 second followed by 2000 rpm for 20 seconds. All the resulting films on the device substrates were annealed at 100° C. for 15 min.

CYTOP is an amorphous fluoropolymer available from Asahi Glass of Japan. A CYTOP solution (CTL-809M, ~9 wt %) was diluted with solvent (CT-solv.180) to make 2 wt % solution and used for processing. The CYTOP (40 nm) layer for the bi-layer dielectrics was formed by spin casting at 3000 rpm for 60 sec. The CYTOP film was annealed at 100° C. for 20 min. $Al_2O_3$ (50 nm) films were deposited on CYTOP (40 nm) layer by atomic layer deposition (ALD) at 110° C. using alternating exposures of trimethyl aluminum [Al(CH$_3$)$_3$] and $H_2O$ vapor at a deposition rate of approximately 0.1 nm per cycle. The capacitance density in devices with CYTOP/Al$_2$O$_3$ devices was separately found to be about 34.5 nF/cm$^2$ (obtained from capacitance values of capacitors with varying area). Finally, Al (150 nm) gate electrodes were deposited over the Alumina layer by thermal evaporation through a shadow mask.

NDI-DTP-NDI Bottom Contact Top Gate OFETs with Al Electrodes

Figures 4A, 4B:
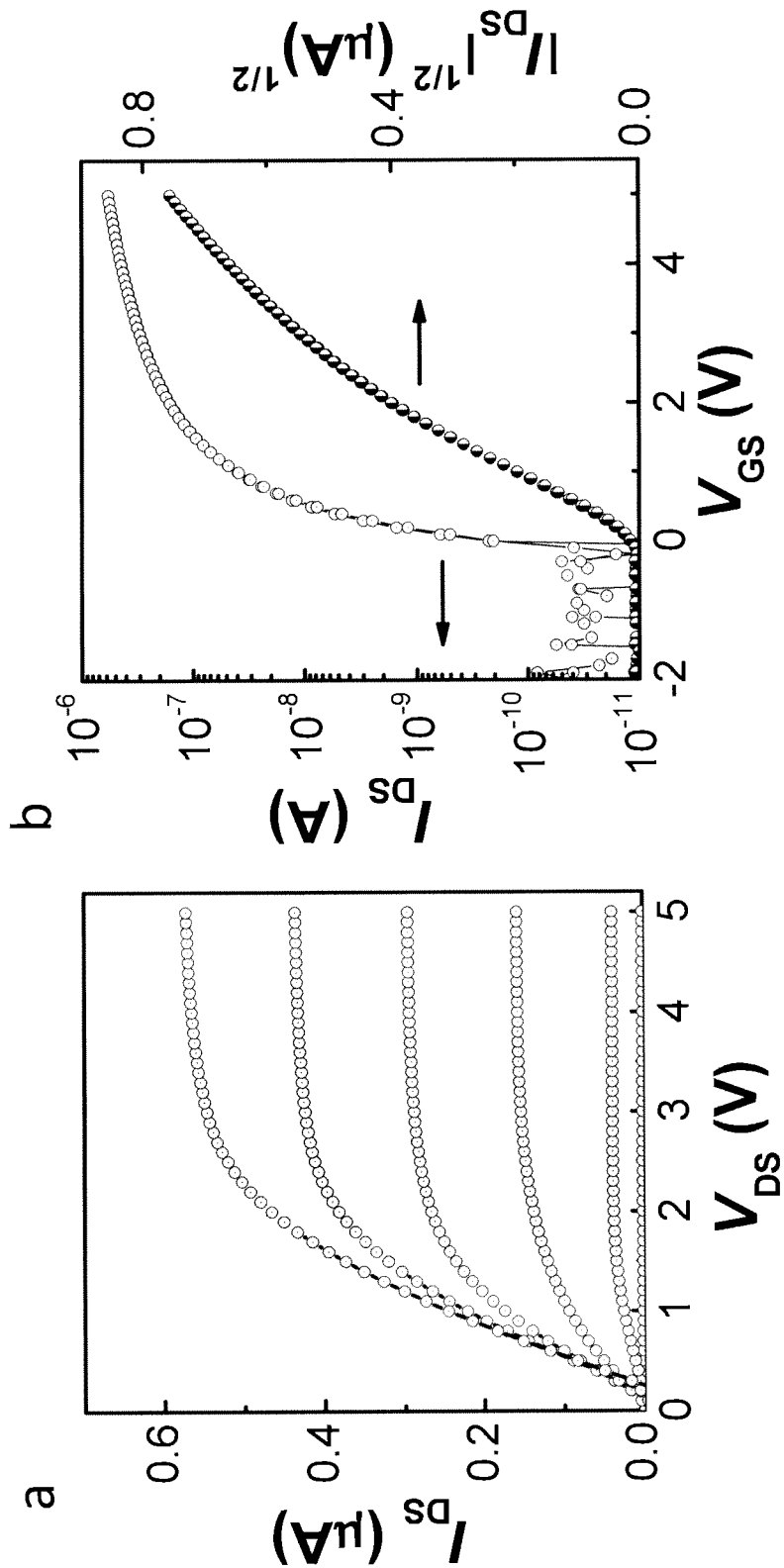
FIGS. 4a and 4b show output (a), and transfer characteristics (b) of a top-gate OFET employing NDI-DTP-NDI as semiconductor and CYTOP/$Al_2O_3$ gate dielectric layer with Al source/drain electrodes. See Example 14.

FIGS. 4a and 4b show the output and transfer characteristics of a single top-gate OFET comprising NDI-DTP-NDI as the semiconductor, with Al source/drain electrodes (W/L=2550 μm/180 μm) and CYTOP/Al$_2$O$_3$ as gate dielectric. The operating voltage for this device was 5 V. The output curves in this case show the plots for $V_{GS}$ varying from 0 to 5 V in 1 V step. The transfer curve is measured in saturation regime ($V_{DS}$=5 V)

A summary of these results is given in Table 3.

TABLE 3

Summary of n-channel electrical parameters for five OFETs comprising NDI-DTP-NDI, employing CYTOP/Al$_2$O$_3$ gate dielectric layer and Al source/drain electrodes (W/L = 62550 μm/180 μm).

| W/L = 2550 μm/180 μm | $V_{DD}$ (V) | μ (cm$^2$/Vs) | $V_{TH}$ (V) | $I_{on/off}$ |
|---|---|---|---|---|
| Device of FIG. 6 | 5 | 0.17 | 0.02 | 2 × 10$^4$ |
| Average (5 devices) | 5 | 0.16 (±0.02) | 0.01 (±0.02) | 2 × 10$^4$ |

These devices showed only n-channel characteristics with average electron mobility value of 0.16 cm$^2$/Vs, an average threshold voltage of 0.01 V, and current on/off ratios of 2×10$^4$. The electron mobility values obtained in these devices are approximately an order of magnitude lower than the mobility values obtained from otherwise similar devices with Au electrodes as described below (which also exhibit ambipolar characteristics), but the almost zero threshold voltages of these n-channel only devices with Al electrodes are very low compared to the threshold voltages of the ambipolar devices described with Au electrodes described below (−13.1 V).

NDI-DTP-NDI Bottom Contact Top Gate OFETs with Au Electrodes

Figures 5A, 5B:
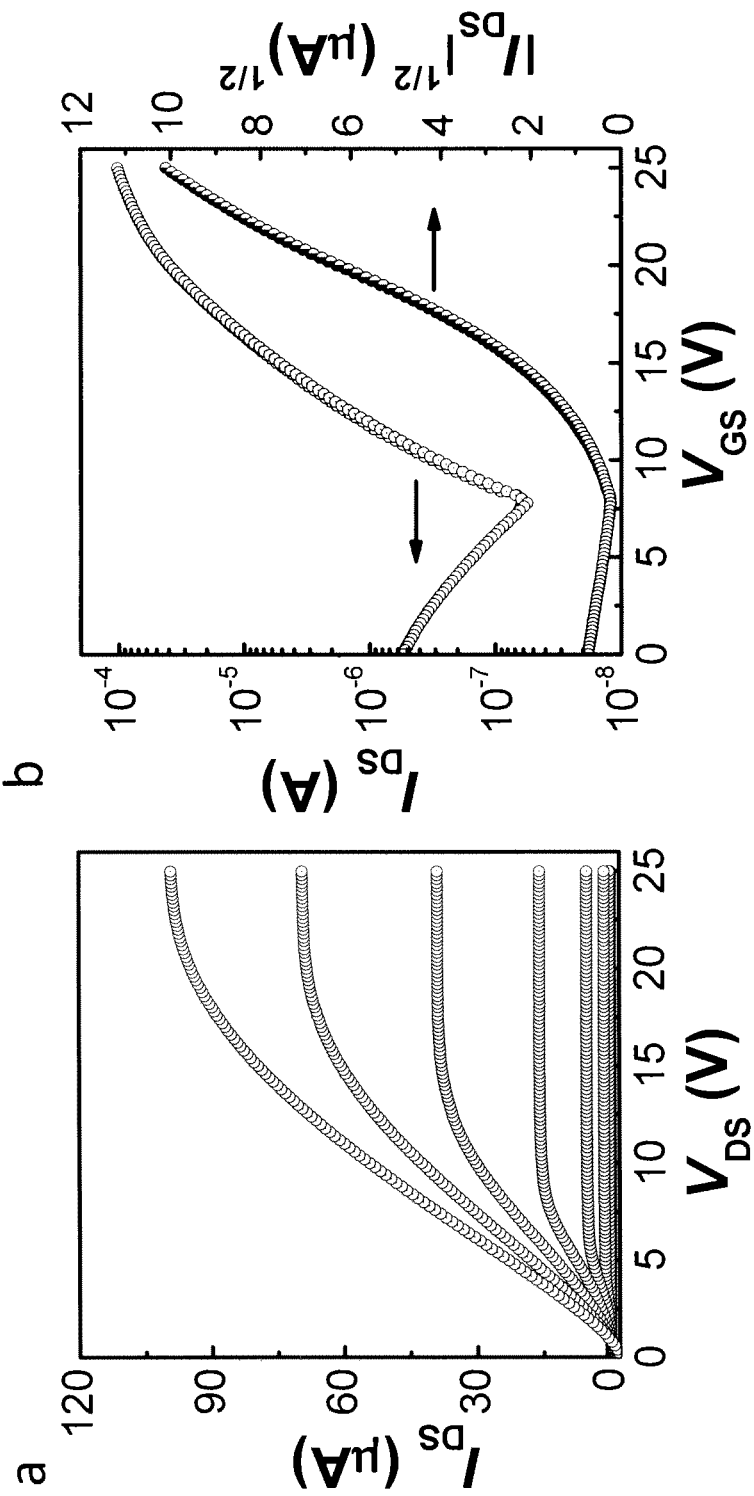
FIG. 5a shows Output characteristics and FIG. 5b shows transfer characteristics for n-channel operation of a top-gate OFET employing NDI-DTP-NDI as semiconductor, and CYTOP/$Al_2O_3$ gate dielectric layer with Au source/drain electrodes. See Example 14.

OFETs otherwise similar to those described above, but with Au rather than Al source and drain electrodes were constructed and tested. The yield was improved to 60% (12 dev./20 dev.) by annealing the semiconductor and CYTOP layers at 100° C. in N$_2$ overnight (16 hours) before Al$_2$O$_3$ layer deposition. These Au devices showed ambipolar electrical characteristics with n-channel dominant transistor behavior. FIGS. 5a and 5b show the output and transfer characteristics of a top-gate OFET employing NDI-DTP-NDI as organic semiconductor and CYTOP/Al$_2$O$_3$ gate dielectric with Au source/drain electrodes (W/L=6050 μm/180 μm), for n-channel operation. The output curves in this case show the plots for $V_{GS}$ varying from 0 to 25 V in 2.5 V step. The transfer curve is measured in saturation regime ($V_{DS}$=25 V). The operating voltage for these devices was 25 V. This device shows electron mobility value of 1.5 cm$^2$/Vs and threshold voltage of 13.4 V. The electron mobility values obtained in these devices were more than three orders of magnitude higher than the mobility values obtained from bottom gate top contact devices on highly doped silicon described above (1.0×10$^{-3}$ cm$^2$/Vs).

Figures 6A, 6B:
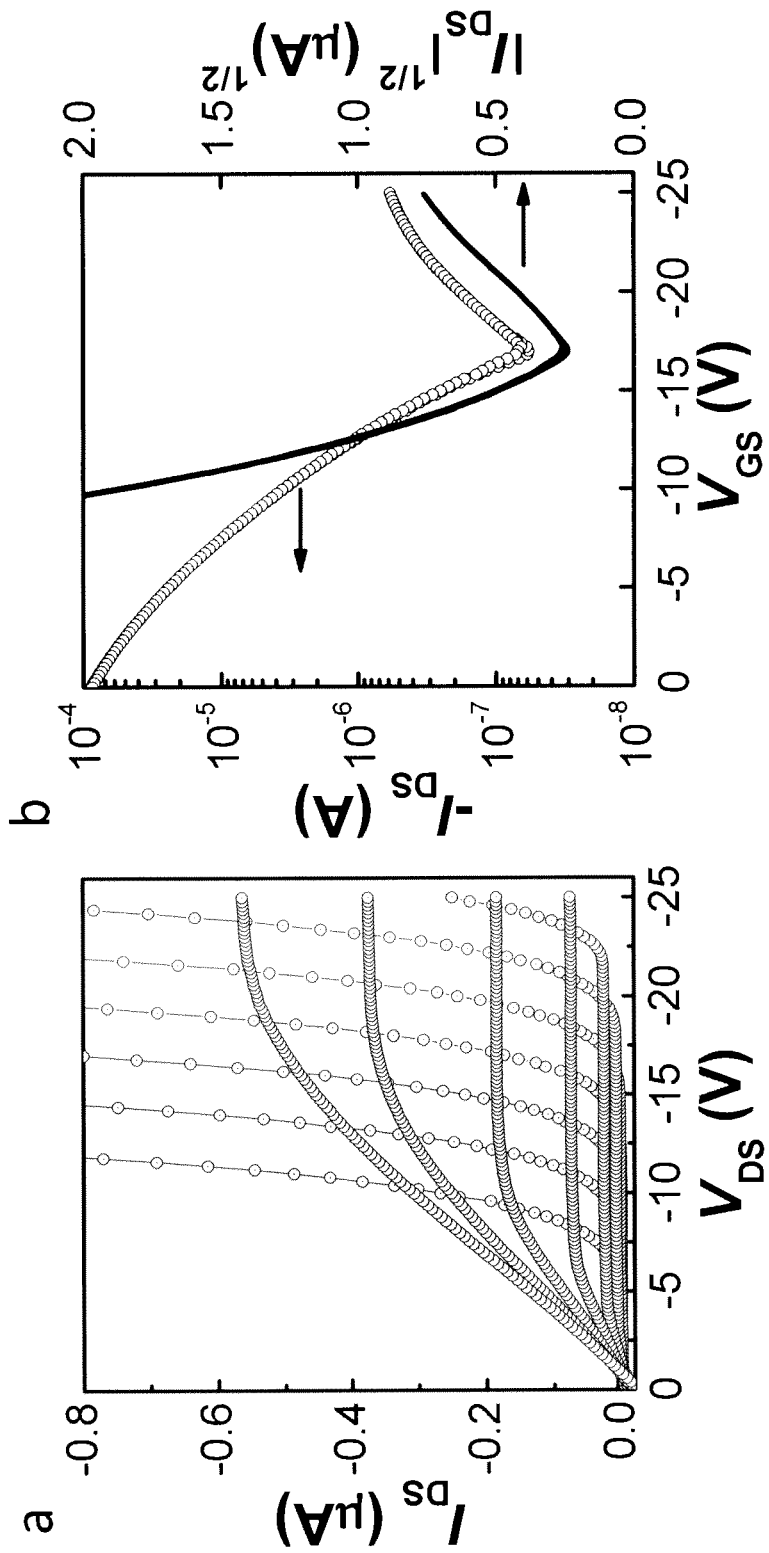
FIG. 6a shows Output characteristics and FIG. 6b shows transfer characteristics for p-channel operation of a top-gate OFET employing NDI-DTP-NDI as semiconductor, and CYTOP/$Al_2O_3$ gate dielectric layer with Au source/drain electrodes. See Example 14.

In p-channel transistor operation {FIGS. 6a ($V_{GS}$ 0 to −25 V in 2.5 V step) and 6b ($V_{DS}$=−25 V)}, the hole mobility value was 9.8×10$^3$ cm$^2$/Vs with threshold voltage of −14.4 V. This shows the n-channel behavior is dominant in these transistors, exhibiting electron mobility more than two orders of magnitude larger than that for p-channel operation. Note that these ambipolar transistors are not turned off at zero gate bias.

Example 15

Solution Processed OFETs Comprising NDI-DTT-NDI

Figures 7A, 7B:
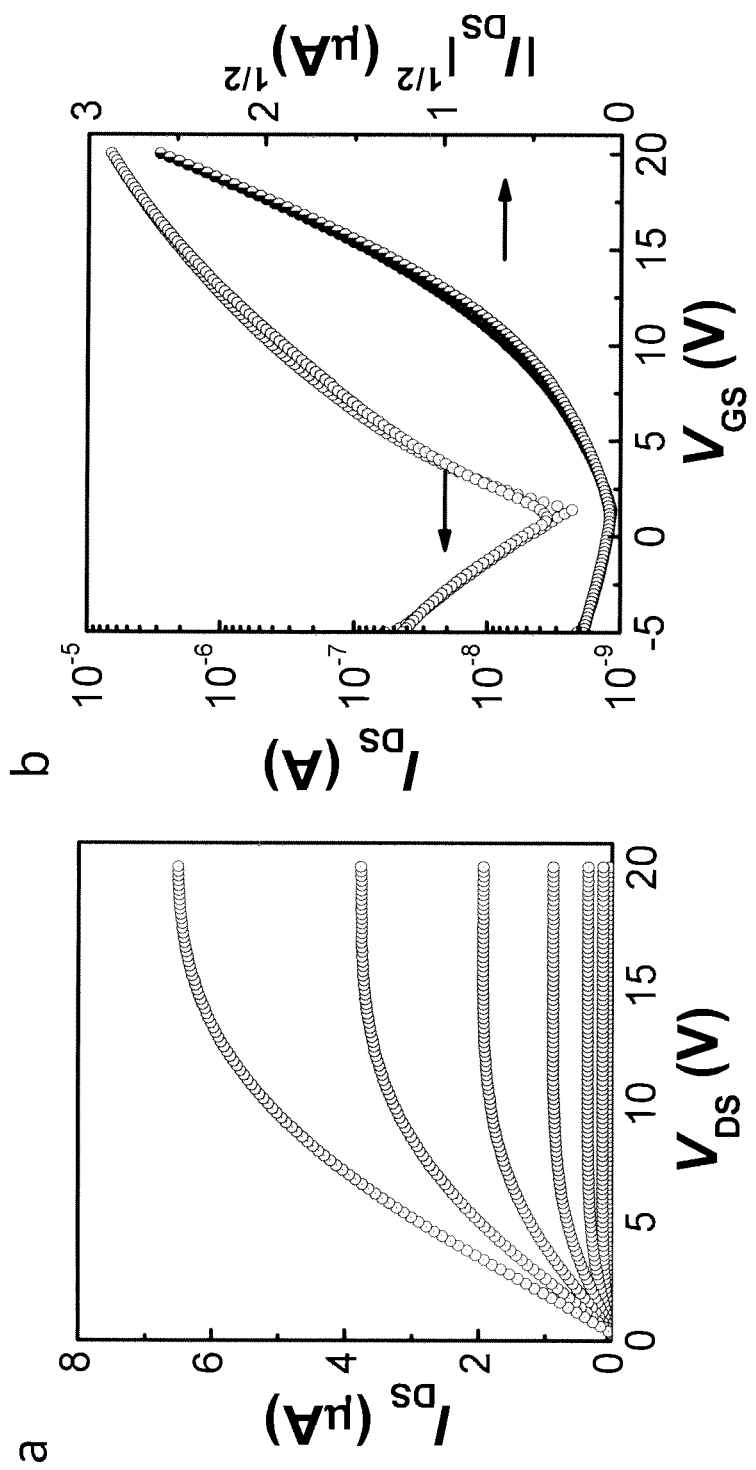
FIG. 7a shows Output characteristics and FIG. 7b shows transfer characteristics for n-channel operation of a top-gate OFET employing NDI-DTT-NDI as semiconductor, and CYTOP/$Al_2O_3$ gate dielectric layer with Au source/drain electrodes. See Example 15.

Bottom contact, top gate OFETs comprising NDI-DTT-NDI (see Example 6) as organic semiconductor, Au source and drain electrodes, and a CYTOP/Al2O3 dielectric were constructed (W/L=2550 μm/180 μm) via procedures similar to those described in Example 12. FIGS. 7a and 7b show the output and transfer characteristics of such a top-gate OFET employing NDI-DTT-NDI as organic semiconductor and CYTOP/Al$_2$O$_3$ gate dielectric with Au source/drain electrodes. The output curves in this case show the plots for $V_{GS}$ varying from 0 to 20 V in 2.5 V step. The transfer curve is measured in saturation regime ($V_{DS}$=20 V). N-channel operation was observed, and those devices showed an average electron mobility value (three devices) of 0.14 cm$^2$/Vs, average threshold voltage of 9.0 V, and current on/off ratio on the order of 10$^3$. The operating voltage for these devices was 20 V.

Example 16

Solution Processed OFETs Comprising NDI-TT-NDI

Figures 8A, 8B:
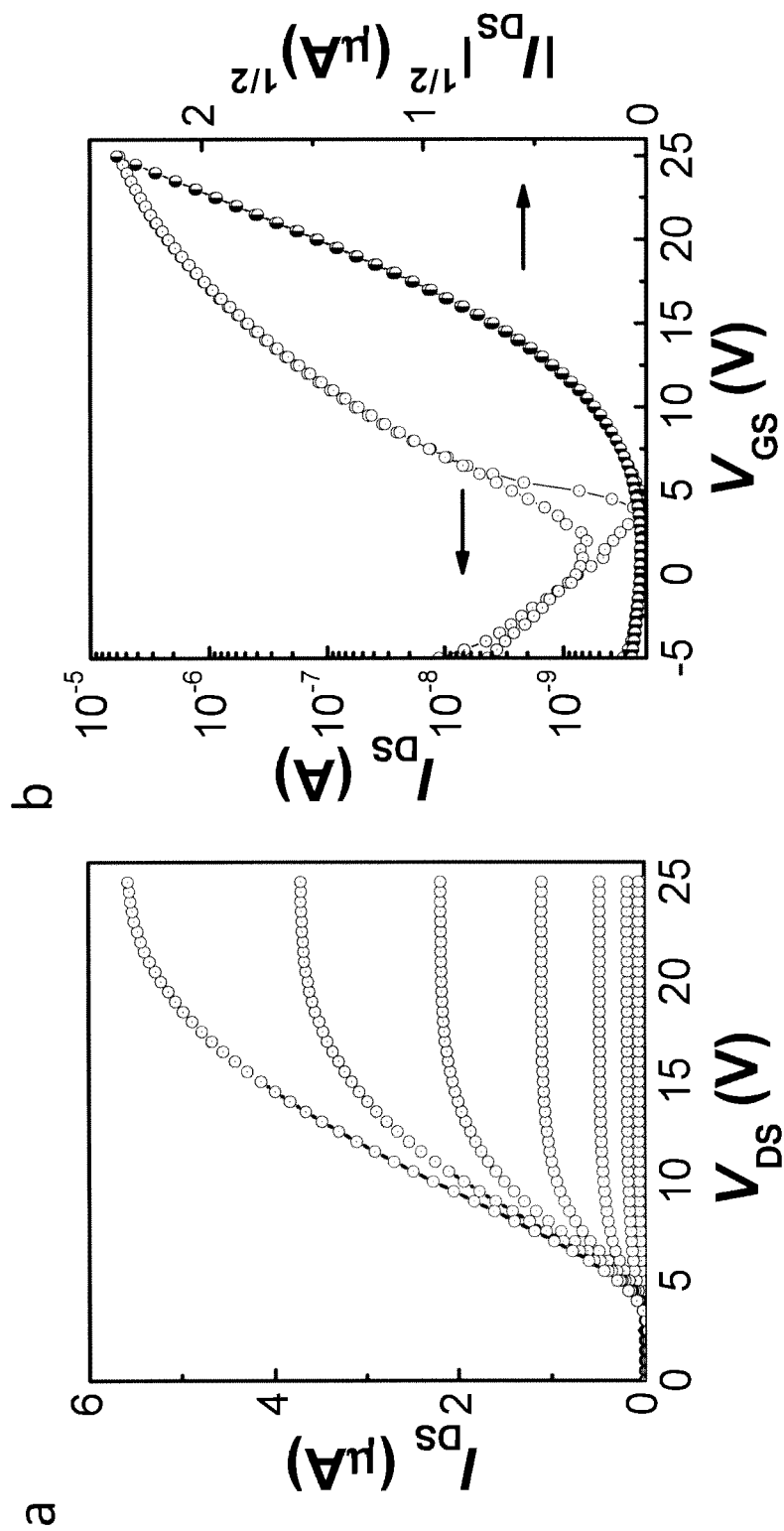
FIG. 8a shows Output characteristics and FIG. 8b shows transfer characteristics for n-channel operation of a top-gate OFET employing NDI-TT-NDI as semiconductor, and CYTOP/$Al_2O_3$ gate dielectric layer with Au source/drain electrodes. See Example 16.

Bottom contact, top gate OFETs comprising NDI-TT-NDI (see Example 4) as organic semiconductor, Au source and drain electrodes, and a CYTOP/Al$_2$O$_3$ dielectric were constructed (W/L=2550 μm/180 μm) via procedures similar to those described in Example 12. FIGS. 8a and 8b show the output and transfer characteristics of such a top-gate OFET employing NDI-TT-NDI as organic semiconductor and CYTOP/Al$_2$O$_3$ gate dielectric with Au source/drain electrodes. The output curves in this case show the plots for $V_{GS}$ varying from 0 to 25 V in 2.5 V step. The transfer curve is measured in saturation regime ($V_{DS}$=25 V). N-channel operation was observed, and those devices showed an average electron mobility value (three devices) of 0.12 cm$^2$/Vs. The average threshold voltage was 12.3 V, and current on/off ratios were in the range 10$^3$ to 10$^4$. The operating voltage for these devices was 25 V.

Example 17

Solution Processed OFETs Comprising NDI-BDTO-NDI

Figures 9A, 9B:
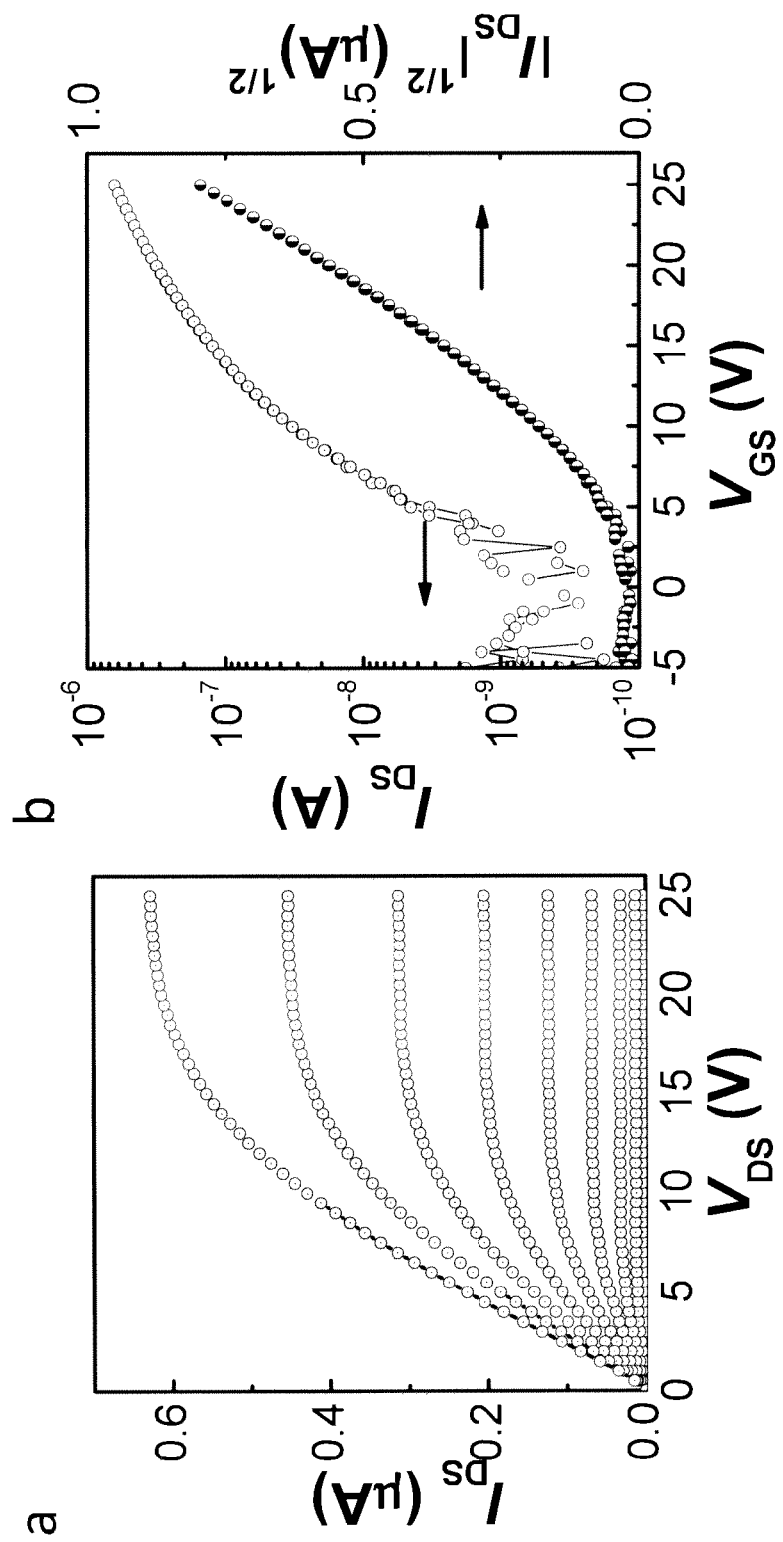
FIG. 9a shows Output characteristics and FIG. 9b shows transfer characteristics for n-channel operation of a top-gate OFET employing NDI-BDTO-NDI as semiconductor, and CYTOP/$Al_2O_3$ gate dielectric layer with Au source/drain electrodes. See Example 17.

Bottom contact, top gate OFETs comprising NDI-BDTO-NDI (see Example 10) as organic semiconductor, Au source and drain electrodes, and a CYTOP/Al$_2$O$_3$ dielectric were constructed (W/L=2550 μm/180 μm) via procedures similar to those described in Example 14. FIGS. 9a and 9b show the output and transfer characteristics of such a top-gate OFET employing NDI-TT-NDI as organic semiconductor and CYTOP/Al$_2$O$_3$ gate dielectric with Au source/drain electrodes. The output curves in this case show the plots for $V_{GS}$ varying from 0 to 25 V in 2.5 V step. The transfer curve is measured in saturation regime ($V_{DS}$=25 V). N-channel operation was observed, and those devices showed an average electron mobility value (five devices) of 7.3 (+2.1) δ10$^{-3}$ cm$^2$/Vs. The average threshold voltage was 8.1 V, and current on/off ratios were in the range 2×10$^3$. The operating voltage for these devices was 25 V.

Example 18

Solution Processed OFETs and Complementary-Like Inverter Comprising NDI-DTP-NDI

The electrical performance of NDI-DTP-NDI OFETs with a CYTOP/Al$_2$O$_3$ bi-layer gate dielectric was measured. Top-gate OFETs with a solution-processed molecular Bis(Naphthalene Diimide) (NDI-DTP-NDI) derivative showed ambipolar transistor properties with an average electron mobility value of 1.2 cm$^2$/Vs and an average hole mobility value of 0.01 cm$^2$/Vs, respectively. Complementary-like inverters comprised of top-gate ambipolar OFETs yielded very high DC voltage gain values more than 90 V/V (up to 122 V/V) at a supply voltage of 25 V.

Top-gate OFETs were fabricated to study the ambipolar performance of NDI-DTP-NDI. The chemical structure of NDI-DTP-NDI is shown in FIG. 10a. See also working example 6 above. Here, a CYTOP/Al$_2$O$_3$ bi-layer was used as a gate dielectric material. FIG. 10b shows the structure of the devices. Gold (50 nm) source and drain electrodes were deposited by thermal evaporation through a shadow mask onto Corning glass substrates (roughness <2 nm). Thin-films of NDI-DTP-NDI were deposited by spin-coating a 30 mg/mL solution in dichlorobenzene. The thin films were then annealed at 100° C. for 15 min. CYTOP solution (CTL-809M, 9 wt %) was diluted with solvent (CT-solv.180) to make a 2 wt. % solution which was spin-coated at 3,000 rpm for 60 s to form a 40 nm-thick CYTOP layer. The CYTOP film was annealed at 100° C. for 20 min. Al$_2$O$_3$ (50 nm) films were then deposited by atomic layer deposition at 110° C. using a Savannah 100 system from Cambridge Nanotech. Finally, Al (150 nm) gate electrodes were deposited by thermal evaporation through a shadow mask. All current-voltage (I-V) characteristics were measured in a N$_2$-filled glove box (O$_2$, H$_2$O<0.1 ppm).

The output ($I_{DS}$ vs. $V_{DS}$) and transfer ($I_{DS}$ vs. $V_{GS}$) characteristics were measured using an Agilent E5272A source/monitor unit. The mobility ($\mu$) and threshold voltage ($V_{TH}$) values were extracted from the highest slope of $|I_{DS}|^{1/2}$ vs. $V_{GS}$ plots in the saturation regime of the transfer characteristics. Average values of mobility and threshold voltage were extracted from 4 to 6 devices fabricated with two different channel widths (W) of 2550 and 6050 µm and the same channel length (L) of 180 µm from a single substrate. The capacitance density of the gate dielectric was measured from parallel plate capacitors fabricated using the same procedures as described above on independent substrates with a geometry of glass/Au/CYTOP (40 nm)/Al$_2$O$_3$ (50 nm)/Al (measured at a frequency of 1 kHz) and areas ranging from 1 mm$^2$ to 4 mm$^2$. A capacitance density of 34.5(±1.0) nF/cm$^2$ was obtained from 4 different batches of samples.

Complementary-like inverter circuits were fabricated using two ambipolar transistors with a channel length of 180 µm and different channel widths of 6050 and 2550 µm, respectively, as shown in FIG. 10c. A common gate electrode, which works as the input ($V_{IN}$) of the inverter circuit, was thermally deposited for both OFETs through a shadow mask. Since the mobility for p-channel operation for OFETs with NDI-DTP-NDI is lower than for n-channel operation, the transistor with larger width (6050 µm) was chosen for p-channel operation.

The output characteristics of a representative OFET with NDI-DTP-NDI are shown in FIG. 10d. This device exhibits electron and hole mobility values of 1.1 and 0.012 cm$^2$/Vs and a $V_{TH}$ of +13.7 and −13.0 V during n- and p-channel operation, respectively.

The device fabrication experiments for batches 1 and 2 were performed with the NDI-DTP-NDI synthesized in a single batch, whereas experiments for batch 3 were done with NDI-DTP-NDI synthesized in a different batch. Table 4 summarizes the results obtained from the various batches. As we can see from the Table 4, batch-to-batch variations in the electrical properties of the devices are observed, showing the average electron mobility values varying from 0.8(±0.2) to 1.2(±0.3) cm$^2$/Vs and the average hole mobility values varying from 0.007(±0.003) to 0.009(±0.004) cm$^2$/Vs. In general, the hole mobility values are approximately two orders of magnitude lower than the electron mobility values.

Figures 11A, 11B, 11C:
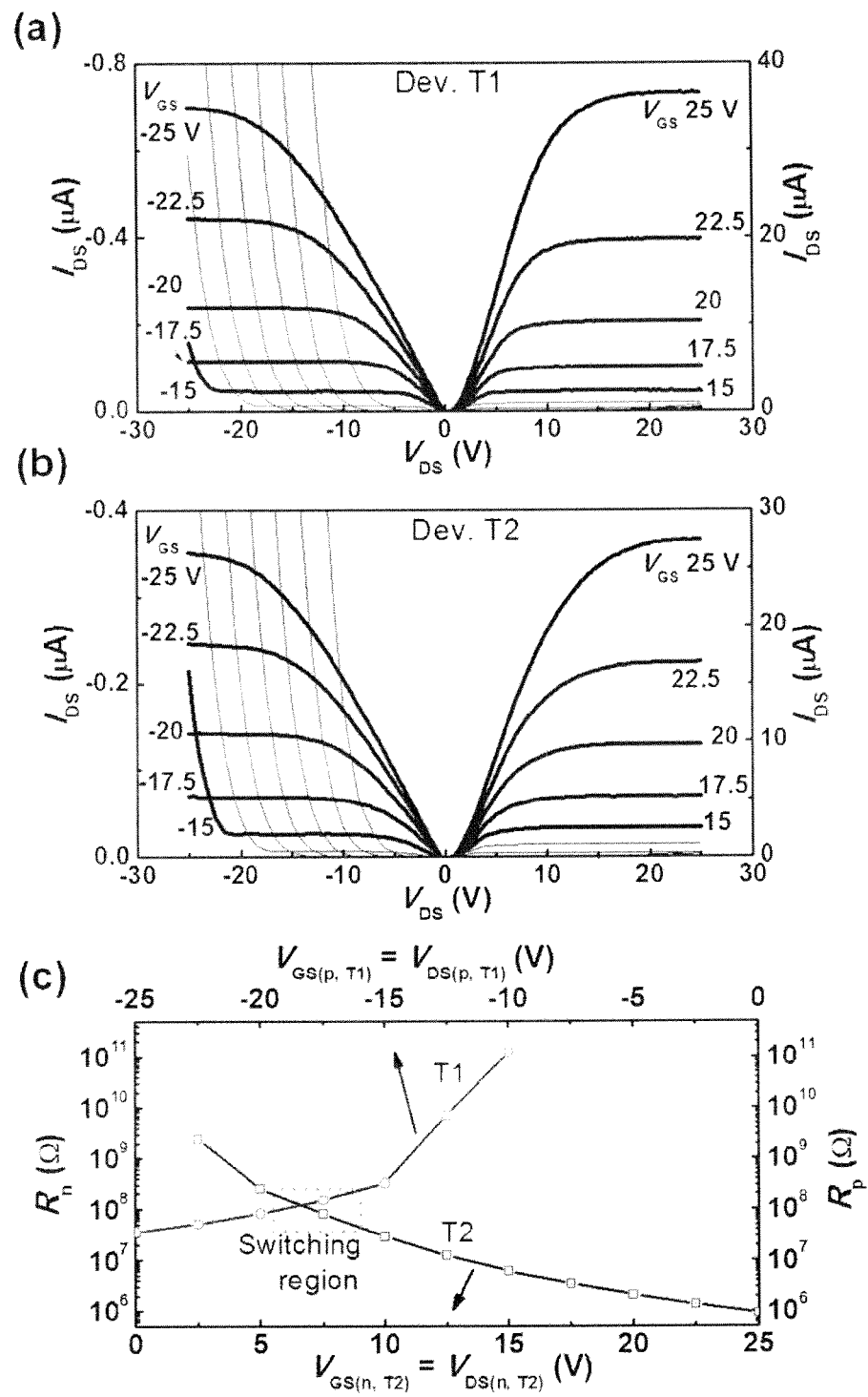
FIG. 11a shows output characteristics of OFET T1.
FIG. 11b shows T2, constituting a complementary-like inverter.
FIG. 11c shows the resistance plot for both transistors, T1 during p-channel operation and T2 during n-channel operation, providing an estimation of the switching point.

FIG. 10e shows the schematic of a complementary-like inverter realized with two ambipolar OFETs, T1 and T2. In complementary-like operation, T1 (W=6050 µm) acts as the p-channel device and T2 (W=2550 µm) acts as the n-channel device. Here, $V_{IN}$ is varied from 0 to 25 V, and $V_{DD}$ and $V_{SS}$ are fixed at 25 and 0 V, respectively. The output characteristics of both T1 and T2 are shown in FIGS. 11a and 11b. A hole mobility value of 0.007 cm$^2$/Vs with a threshold voltage value of −12.6 V and an electron mobility value of 0.86 cm$^2$/Vs with a threshold voltage value of 13.5 V were obtained from T1 and T2, respectively. The static performance of an inverter is evaluated by its DC gain values from the measured voltage transfer characteristics. The operation of a complementary inverter can be explained by two series-connected voltage-dependent variable resistors. In general, for a given supply voltage, $V_{DD}$, the switching voltage ($V_M$) corresponds to the $V_{IN}$ that makes the resistance of the n-channel FET ($R_n=V_{DS}/I_{DS}$) equal to the resistance of the p-channel FET ($R_p=-V_{DS}/-I_{DS}$). Accordingly, a device resistance plot can be used to analyze the switching voltage of complementary-like inverters. For example such devices as found in J. B. Kim, et al., Flexible hybrid complementary inverters with high gain and balanced noise margins using pentacene and amorphous InGaZnO thin-film transistors, *Org. Electron.*, 11 (2010) 1074-1078. This method is suitable for estimating the switching region in the voltage transfer characteristics in inverters with ambipolar OFETs, because it does not restrict us to calculating the resistances in a predefined operating regime, as is done in the extraction of the mobility and threshold voltage values in ambipolar devices. Moreover, there is no proper definition of threshold voltage for these devices throughout the operation.

Figures 12A, 12B:
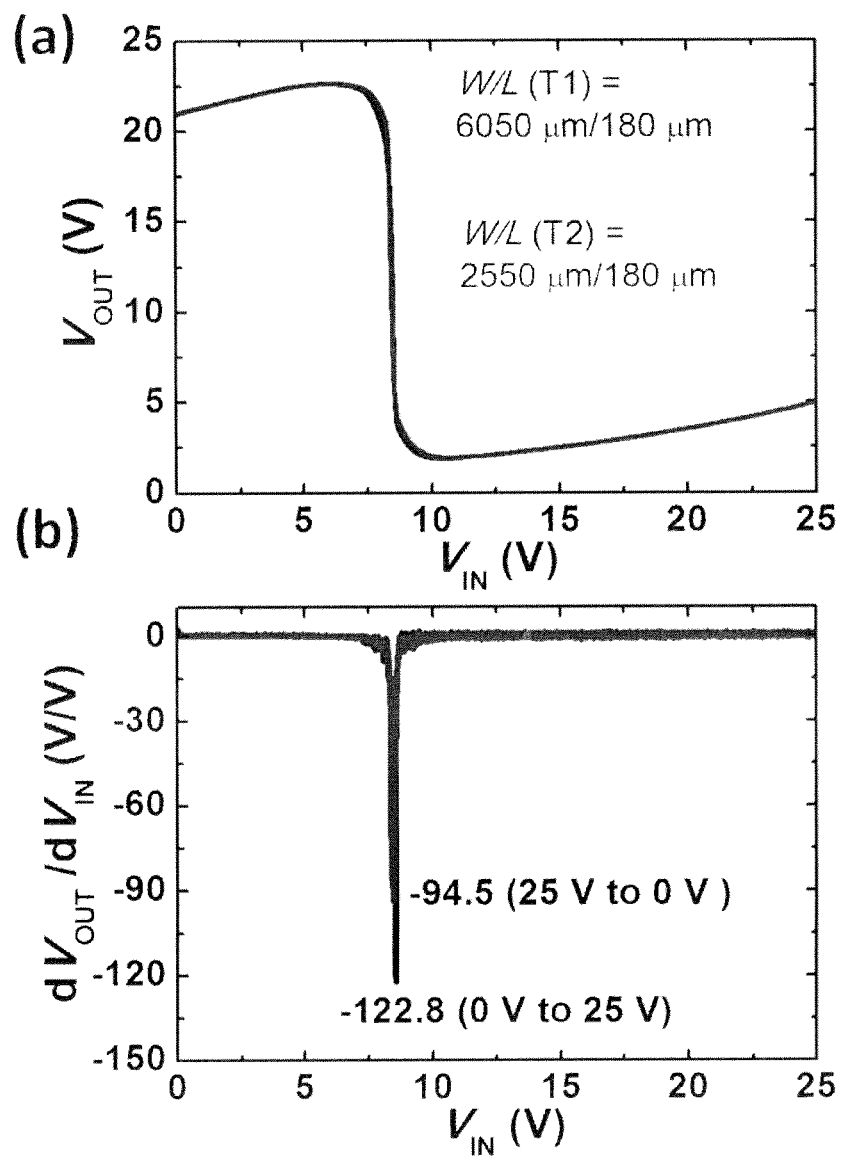
FIG. 12a shows hysteresis voltage transfer characteristics and FIG. 12b DC gains of a complementary-like inverter.

The resistances during p- and n-channel operations can be obtained when gate and drain terminals are connected, or they can be extracted from the output characteristics of the independent OFETs at the condition of $V_{GS}=V_{DS}$. See, for example, Kim et al., *Org. Electron.*, 11 (2010) 1074-1078. Using the same technique, the plot of the resistances of devices T1 ($R_p$) and T2 ($R_n$) are obtained (FIGS. 11a and 11b). The subscript in the resistances ($R_p$, $R_n$) indicates the operation of the particular transistor in the complementary-like inverter; T1 is working as p-channel and T2 as n-channel in this case. FIG. 11c shows the values of $R_p$ and $R_n$ extracted from output characteristics for different values of $V_{GS}=V_{DS}$. This plot suggests the switching should occur near a $V_{IN}$ of 7 V. FIGS. 12a & b show the voltage transfer characteristics and DC gain of a representative complementary-like inverter fabricated with ambipolar OFETs T1 and T2. As we can see in the voltage transfer characteristic, a complementary-like inverter shows a DC output swing range of about 20 V when $V_{IN}$ is varied from 0 to 25 V at a supply voltage ($V_{DD}$) of 25 V. The DC gain is obtained by differentiating $V_{OUT}$ with respect to $V_{IN}$. High DC gain values of 122.8 V/V and 94.5 V/V were obtained for this inverter in the forward scan ($V_{IN}$ varied from 0 to 25 V) and in the reverse scan ($V_{IN}$ varied from 25 to 0 V), respectively. No hysteresis was observed between forward and reverse scans. The other inverters fabricated in the same process exhibited high gain values exceeding 90 V/V. These numbers appear to be higher than the values from many other inverters with ambipolar OFETs reported in the literature.

TABLE 4

Summary of results for top-gate bottom-contact
OFETs with NDI-DTP-NDI with L = 180 μm and
W = 2550 or 6050 μm.

| Batch | Opera-tion | $V_{DD}$ (V) | $\mu_{max}$ (cm$^2$/Vs) | $\mu_{ave}$ (cm$^2$/Vs) | $V_{TH}$ (V) |
|---|---|---|---|---|---|
| 1 (6 Dev.) | n-channel | 25 | 1.1 | 0.8 (±0.2) | +12.7 (±0.6) |
| | p-channel | −25 | 0.01 | 0.009 (±0.004) | −12.7 (±0.4) |
| 2 (6 Dev.) | n-channel | 25 | 1.5 | 1.2 (±0.3) | +13.0 (±0.9) |
| | p-channel | −25 | 0.01 | 0.007 (±0.003) | −14.2 (±0.7) |
| 3 (4 Dev.) | n-channel | 25 | 0.8 | 0.8 (±0.1) | +14.8 (±0.8) |
| | p-channel | −25 | 0.009 | 0.007 (±0.001) | −12.4 (±0.7) |

Example 19

Preparation of OFET Devices Comprising NDI-BTTZ-NDI on Glass Substrates Using Spin Coating OFETs with bottom contact and top gate structure were fabricated on glass substrates (Eagle 2000 Corning). Au (50 nm) or Ag (50 nm) bottom contact source/drain electrodes were deposited by thermal evaporation through a shadow mask. Organic semiconductor (DRR-IV-209n, also known as NDI-BTTZ-NDI; see working example 12 above) layers were formed on the substrates by spin coating with a solution prepared from 1,4-dioxane (20 mg/mL), 1,1,1,2-Tetrachloroethane (20 mg/mL), dichlorobenzene (20 mg/mL), and mesitylene-tetralin (20 mg/mL) at 500 rpm for 10 sec and at 2,000 rpm for 20 sec. Then, samples were annealed at 100° C. (1,4-dioxane sample) or at 120° C. for 10 min (the other samples) in a N$_2$-filled dry box. CYTOP (45 nm)/Al$_2$O$_3$ (50 nm) layers were used as top-gate dielectrics. CYTOP solution (CTL-809M) was purchased from Asahi Glass with a concentration of 9 wt. %. To deposit the 45 nm-thick CYTOP layers, the original solution diluted with their solvents (CT-solv.180) to have solution:solvent ratios of 1:3.5. The 45 nm-thick CYTOP layers were deposited by spin casting at 3000 rpm for 60 sec. The CYTOP (45 nm) films were annealed at 100° C. for 20 min. All spin coating and annealing processes were carried out in a N$_2$-filled dry box. Then, the Al$_2$O$_3$ dielectric films (50 nm) were deposited on top of the CYTOP layer using a Savannah 100 ALD system from Cambridge Nanotech Films were grown at 110° C. using alternating exposures of trimethyl aluminum [Al(CH$_3$)$_3$] and H$_2$O vapor at a deposition rate of approximately 0.1 nm per cycle. Finally, Al (150 nm) gate electrodes were deposited by thermal evaporation through a shadow mask.

All current-voltage (I-V) characteristics of OFETs were measured with an Agilent E5272A source/monitor unit in a N$_2$-filled glove box (O$_2$, H$_2$O<0.1 ppm).

Figure 13:
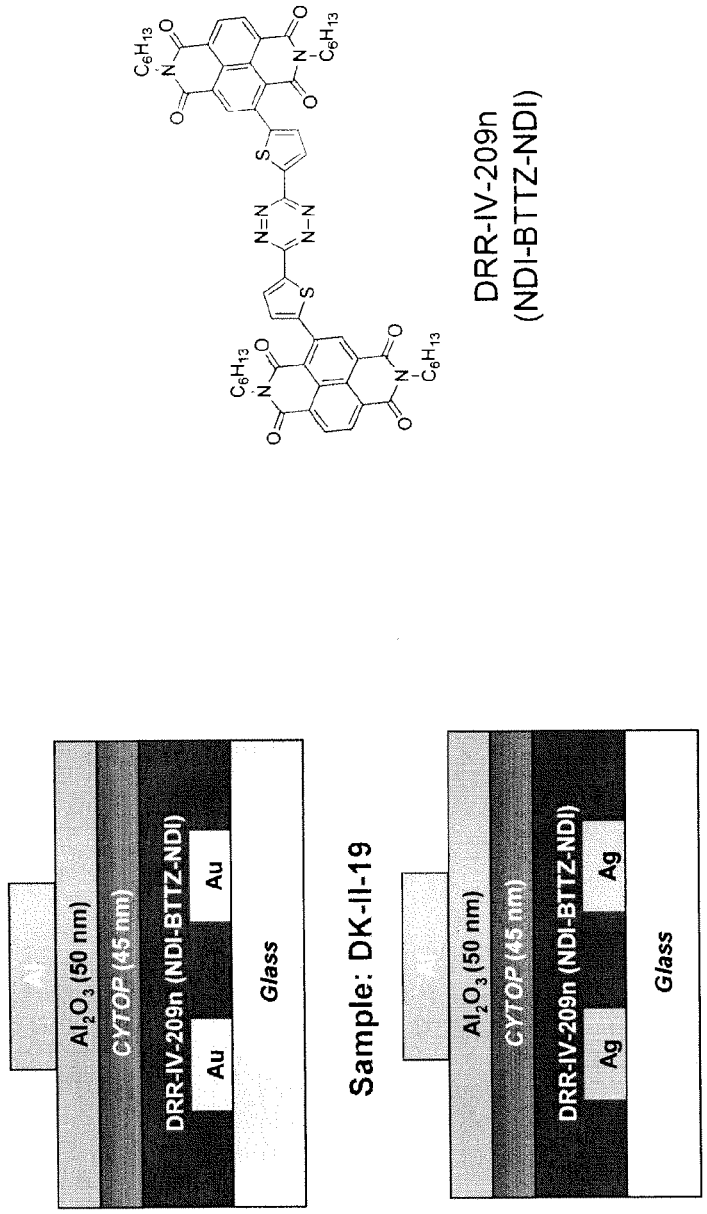
FIG. 13 illustrates the OFET structures and molecular structure for a solvent study.

FIG. 13 illustrates the device architecture including use of gold and silver electrodes on glass. The structure of the compound is also shown.

FIGS. 14-19 show the OFET testing results as a function of solvent and electrode material.

Figure 20:
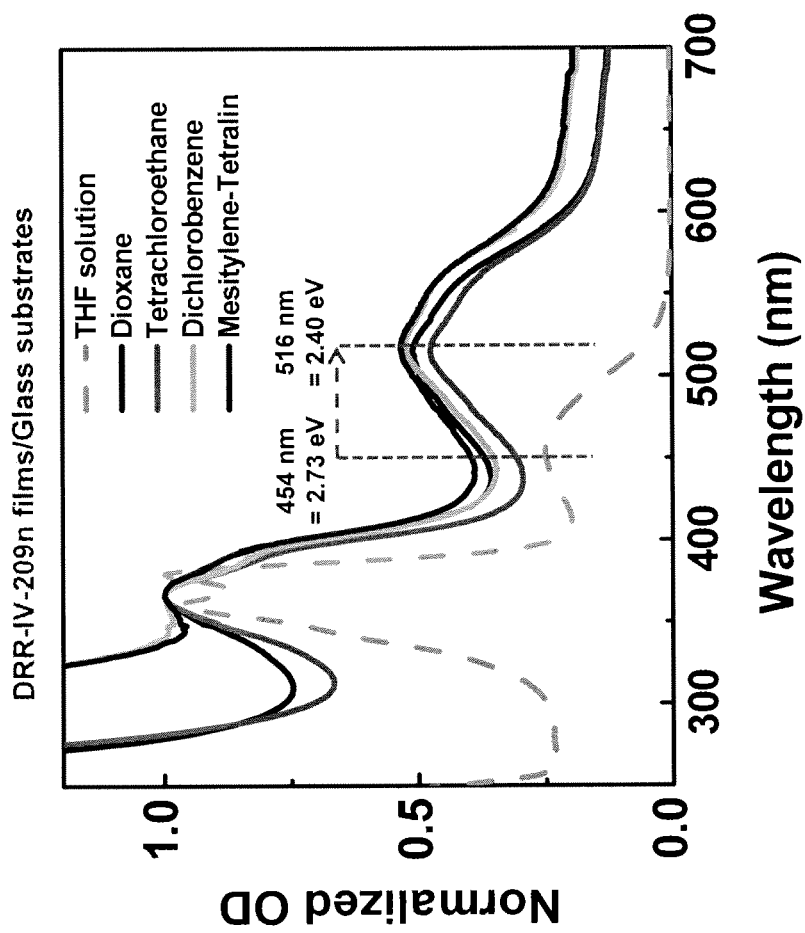
FIG. 20 illustrates UV-Vis spectra for films on glass substrates cast from different solvents.

FIG. 20 shows the UV-Vis spectra as function of solvent used on glass substrates.

The OFETs processed from dichlorobenzene showed the best performance. The silver S/D electrodes seemed to be oxidized. The $V_{Th}$ of OFETs with Ag electrodes is higher than that of OFETs with Au electrodes.

The data are summarized below in Table BK-1:

TABLE BK-1

| Batch | W/L | Cin (nF/cm2) | Solvent | S/D electrode | μ (cm2/Vs) | $V_{TH}$ (V) | Ion/off |
|---|---|---|---|---|---|---|---|
| DK-I-146 | 2550 μm/ 180 μm (ave. 5 dev.) | 35.2 | 1,4-dioxane | Au | 0.016 ± 0.03 | 3.1 ± 0.6 | 103 |
| DK-II-8 | 2550 μm/ 180 μm (ave. 9 dev.) | 35.2 | 1,4-dioxane | Au | 0.042 ± 0.03 | 3.4 ± 0.5 | 103 |
| | 2550 μm/ 180 μm (ave. 6 dev.) | 35.2 | dichlorobenzene | Au | 0.13 ± 0.01 | 4.9 ± 0.4 | 104 |
| DK-II-19 | 2550 μm/ 180 μm (ave. 8 dev.) | 35.2 | dichlorobenzene | Au | 0.11 ± 0.01 | 6.5 ± 1.4 | 104 |
| | 2550 μm/ 180 μm (ave. 8 dev.) | 35.2 | dichlorobenzene | Ag | 0.09 ± 0.04 | 8.9 ± 0.4 | 104 |
| | 2550 μm/ 180 μm (ave. 8 dev.) | 35.2 | Mesitylene-tetralin | Au | 0.13 ± 0.02 | 7.4 ± 0.6 | 104 |
| | 2550 μm/ 180 μm (ave. 8 dev.) | 35.2 | Mesitylene-tetralin | Ag | 0.12 ± 0.03 | 8.3 ± 0.2 | 104 |
| DK-II-25 | 2550 μm/ 180 μm (ave. 4 dev.) | 35.2 | 1,1,1,2-Tetrachloroethane | Au | 5.3 (±2.1) × 10−3 | 8.2 ± 0.3 | 103 |

Example 20

Preparation of OFET Devices Using Ink Jet Printing

OFETs with bottom contact and top gate structure were fabricated on glass substrates (Eagle 2000 Corning) or polyethersulfone (PES) substrate. Au (50 nm) or Ag (50 nm) bottom contact source/drain electrodes were deposited by thermal evaporation through a shadow mask. Printed Ag source/drain electrodes were made by a Dimatix DMP 2831 inkjet printer. Organic semiconductor (DRR-IV-209n also known as NDI-BTTZ-NDI) layers were patterned by inkjet printing. DRR-IV-209n ink was prepared as follows: DRR-IV-209n was dissolved in dichlorobenzene 99% (Sigma Aldrich) or in mixture of 1,2,3,4-Tetrahydronaphthalene anhydrous, 99% (Sigma Aldrich) and mesitylene, 99% (Sigma Aldrich) with a ratio of 1:1 in volume. Concentrations of both inks were 5 mg/mL. Both inks were stirred over night in $N_2$-filled dry box. A Dimatix DMP 2831 inkjet printing system was used to pattern semiconductor layers. Active layer was printed on glass and flexible substrates at 45° C. in air ambient. After printing, all samples were annealed at 100° C. for 15 min in air ambient. CYTOP (45 nm)/$Al_2O_3$ (50 nm) layers were used as top-gate dielectrics. CYTOP solution (CTL-809M) was purchased from Asahi Glass with a concentration of 9 wt. %. To deposit the 45 nm-thick CYTOP layers, the original solution diluted with their solvents (CT-solv.180) to have solution:solvent ratios of 1:3.5. The 45 nm-thick CYTOP layers were deposited by spin casting at 3000 rpm for 60 sec. The CYTOP (45 nm) films were annealed at 100° C. for 20 min. All spin coating and annealing processes were carried out in a $N_2$-filled dry box. Then, the $Al_2O_3$ dielectric films (50 nm) were deposited on top of the CYTOP layer using a Savannah 100 ALD system from Cambridge Nanotech Inc. Films were grown at 110° C. using alternating exposures of trimethyl aluminum [$Al(CH_3)_3$] and $H_2O$ vapor at a deposition rate of approximately 0.1 nm per cycle. Finally, Al (150 nm) gate electrodes were deposited by thermal evaporation through a shadow mask.

All current-voltage (I-V) characteristics of OFETs were measured with an Agilent E5272A source/monitor unit in a $N_2$-filled glove box ($O_2$, $H_2O$<0.1 ppm).

Figure 21:
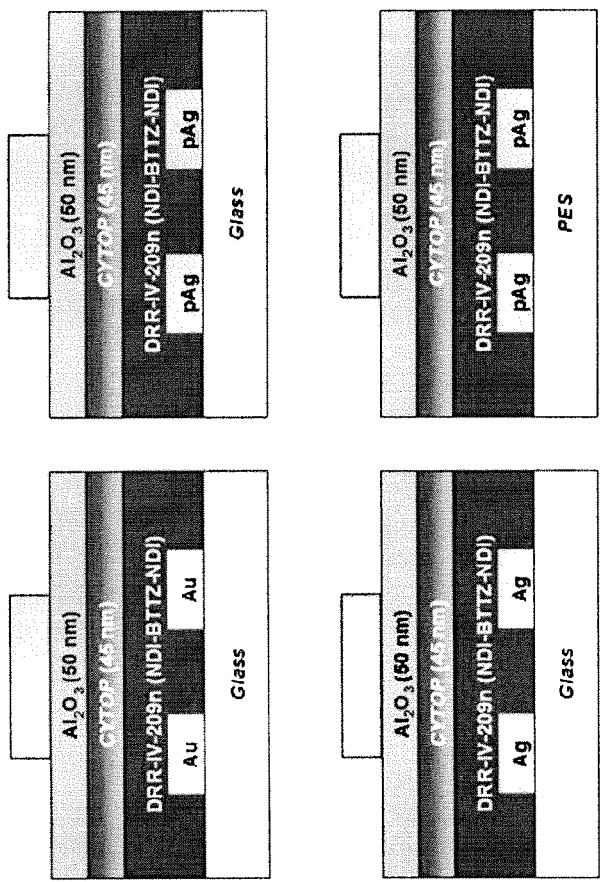
FIG. 21 illustrates OFET structures for printed OFET structures.
Figure 23:
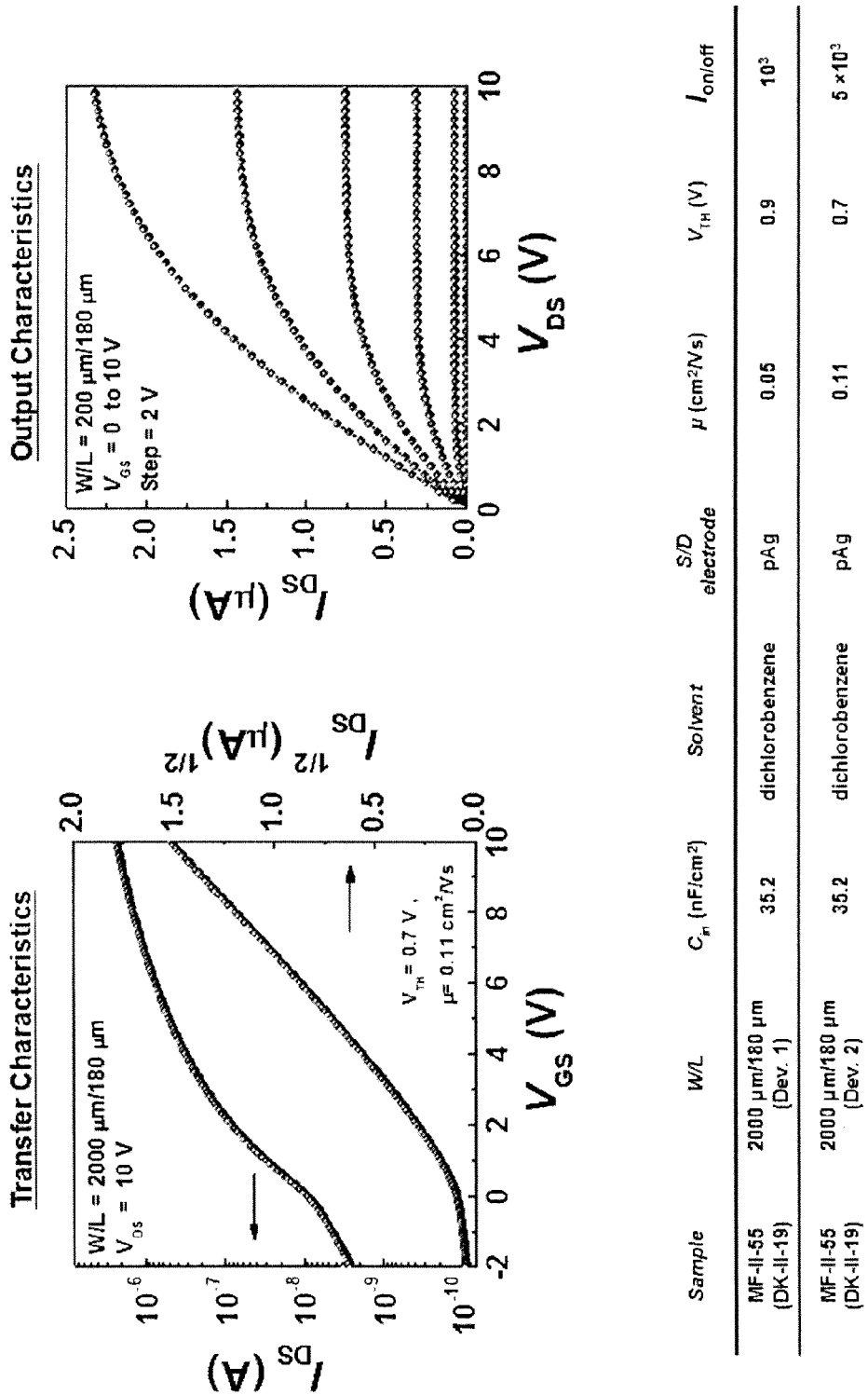
FIG. 23 illustrates printed OFET results for dichlorobenzene solvent and pAg electrode.
Figure 25:
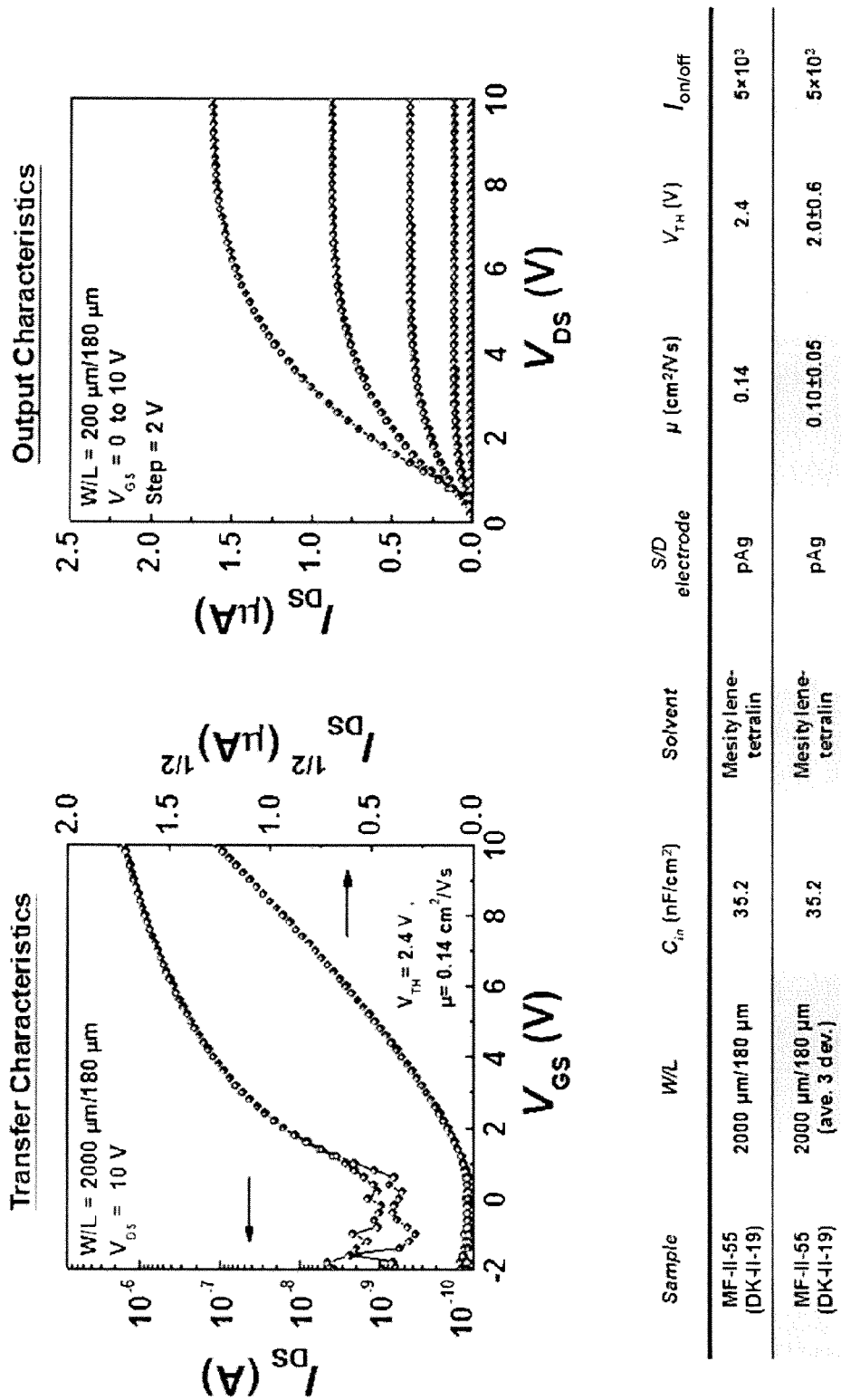
FIG. 25 illustrates printed flexible OFET results for mesitylene-tetralin solvent and pAg electrode.

FIG. 21 illustrates the device structures and the ink-jet printer.

FIGS. 22-25 show OFET behavior for different solvent, electrode, and substrate combinations. The flexible printed OFETs with printed Ag S/D electrode processed from dichlorobenzene solvent showed the best results.

The data are summarized below in Table BK-2:

TABLE BK-2

| Batch | W/L | Cin (nF/cm2) | Solvent | Substrate | S/D electrode | μ (cm2/Vs) | VTH (V) | Ion/off |
|---|---|---|---|---|---|---|---|---|
| MF-II-55 (DK-II-19) | 2000 μm/ 180 μm (ave. 8 dev.) | 35.2 | dichlorobenzene | Glass | Au | 0.06 ± 0.02 | 6.5 ± 0.6 | 104 |
| | 2000 μm/ 180 μm | 35.2 | dichlorobenzene | Glass | Ag | No FET behavior due to Ag oxidation | | |
| | 2000 μm/ 180 μm (Dev. 1) | 35.2 | dichlorobenzene | Glass | pAg | 0.07 | 0.9 | 103 |
| | 2000 μm/ 180 μm (Dev. 2) | | | | | 0.14 | 0.7 | 5 × 103 |
| | 2000 μm/ 180 μm (ave. 7 dev.) | 35.2 | dichlorobenzene | PES | pAg | 0.14 ± 0.02 | 1.7 ± 0.3 | 5 × 104 |
| MF-II-55 (DK-II-19) | 2000 μm/ 180 μm | 35.2 | Mesitylene-tetralin | Glass | Au | No FET behavior due to de-wetting | | |
| | 2000 μm/ 180 μm | 35.2 | Mesitylene-tetralin | Glass | Ag | | | |
| | 2000 μm/ 180 μm | 35.2 | Mesitylene-tetralin | Glass | pAg | | | |
| | 2000 μm/ 180 μm (ave. 3 dev.) | 35.2 | Mesitylene-tetralin | PES | pAg | 0.10 ± 0.05 | 2.0 ± 0.6 | 5 × 103 |

Example 21

Environmental Stability of OFET Devices from Spin Coating

To study their environmental stability, DRR-IV-209n (NDI-BTTZ-NDI) based spin-coated OFETs with Au electrode processed by dichlorobenzene on glass substrates were exposed to a normal ambient condition with a relative humidity between 30 and 50%. After two weeks in air, gradual decrease of the average value of $\mu$ from $0.13\pm0.01$ cm$^2$/V to $0.10\pm0.03$ cm$^2$/Vs was observed. In threshold voltage, the positive shifts from $4.9\pm0.4$ to $8.4\pm1.3$ were observed. However, these changes on threshold voltage and mobility values were back to initial values through vacuum annealing.

Figure 26:
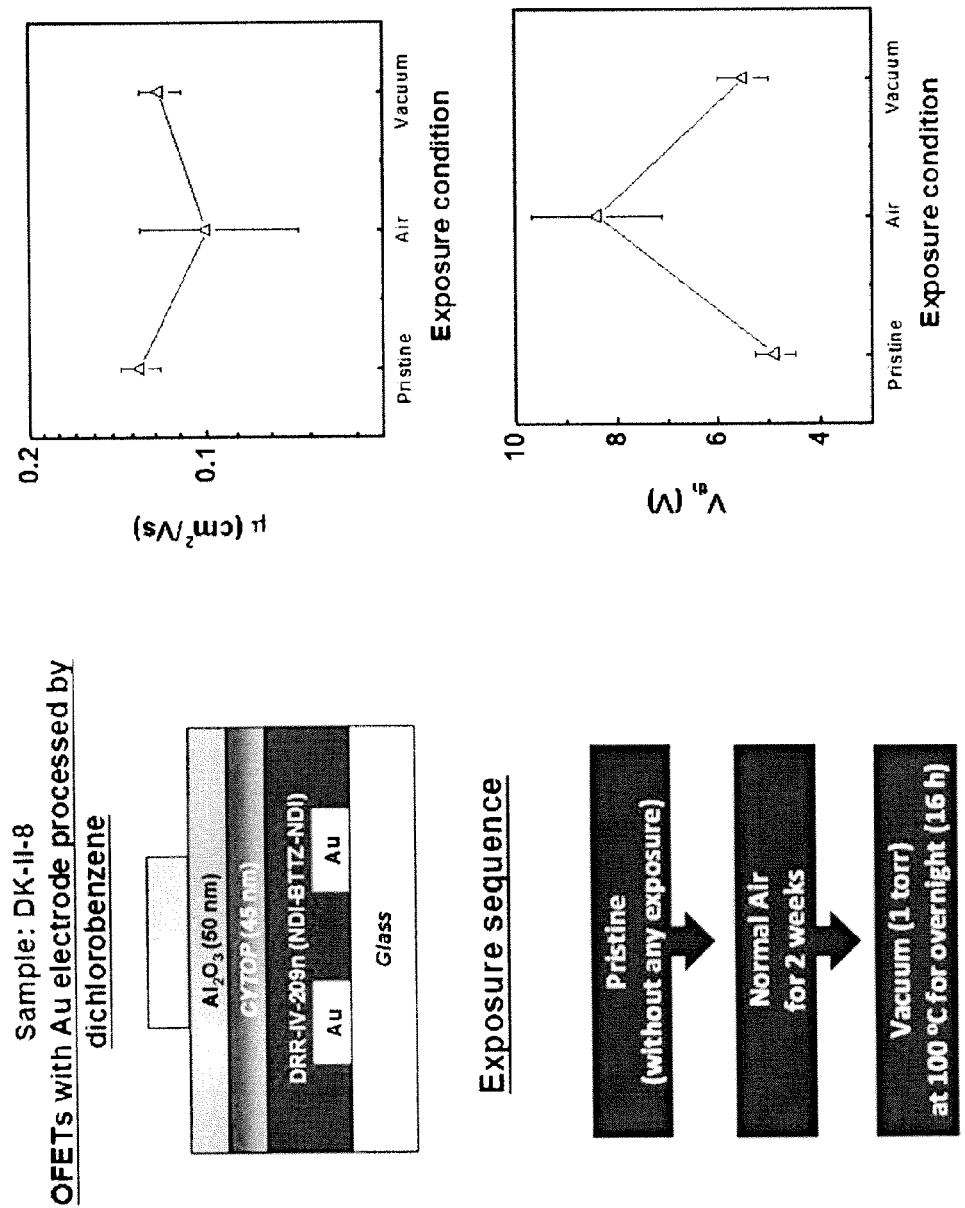
FIG. 26 illustrates air stability testing for rigid OFETs.
Figure 28:
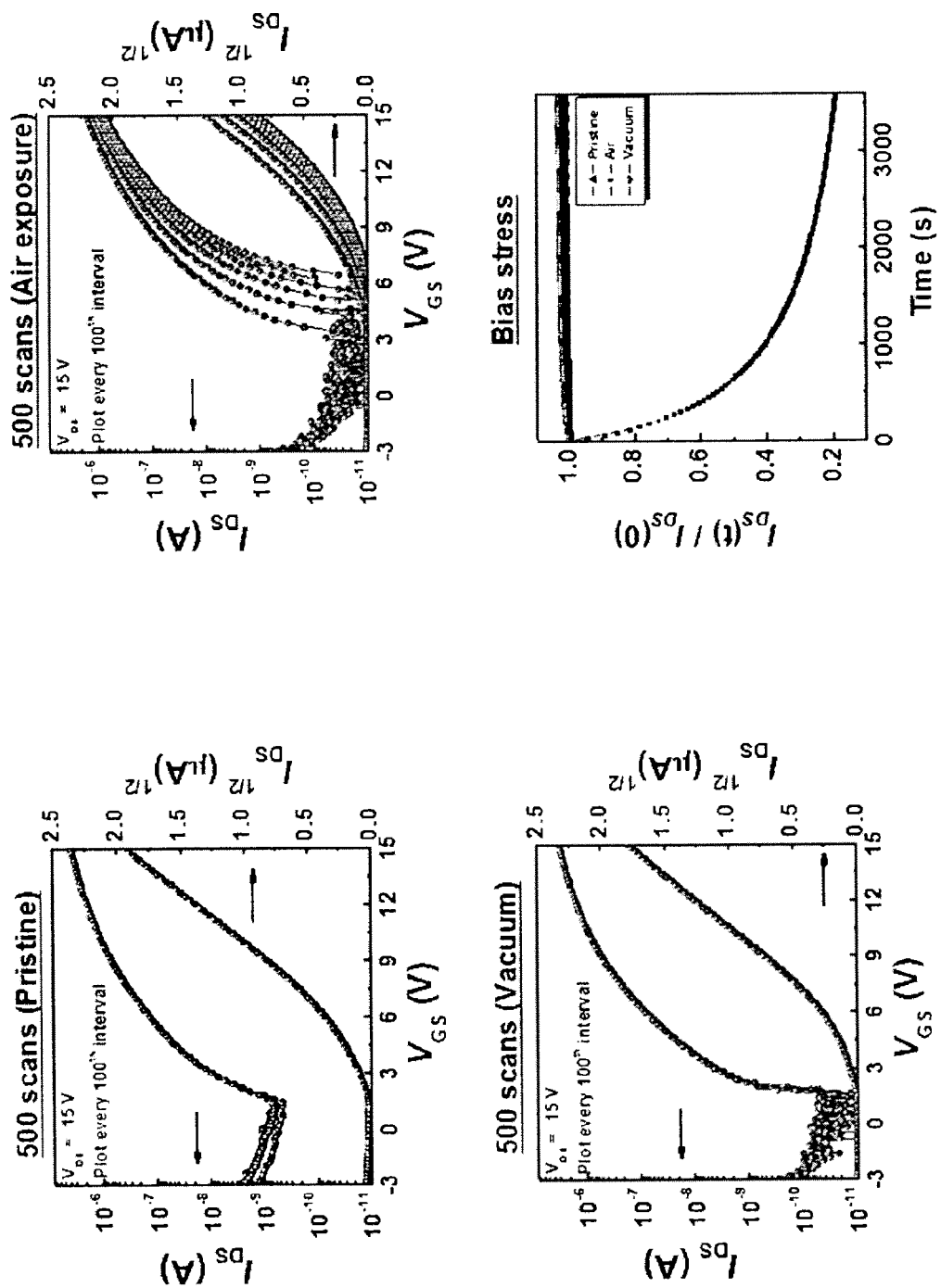
FIG. 28 illustrates electrical stability of rigid OFETs.

FIGS. 26-28 illustrate the results. The data for air stability and electrical stability are summarized below in Tables BK-3 and BK-4:

TABLE BK-3

Air Stability

| Exposure condition | $C_{in}$ (nF/cm2) at 1 kHz | $\mu$ (cm2/Vs) | VTH (V) |
|---|---|---|---|
| Pristine | 35.2 | 0.13 ± 0.01 | 4.9 ± 0.4 |
| Air | 35.2 | 0.10 ± 0.03 | 8.4 ± 1.3 |
| Vacuum | 35.2 | 0.12 ± 0.01 | 5.5 ± 0.5 |

TABLE BK-4

Electrical Stability

| Exposure condition | $C_{in}$ (nF/cm$^2$) | W/L | status | $\mu$ (cm$^2$/Vs) | $V_{TH}$ (V) |
|---|---|---|---|---|---|
| Pristine | 35.2 | 2550 µm/ 180 µm | Initial | 0.15 | 4.6 |
| | | | After 500 scans | 0.15 | 4.5 |
| | | | After 1 hour bias stress | 0.15 | 4.5 |
| Air | 35.2 | 2550 µm/ 180 µm | Initial | 0.13 | 6.5 |
| | | | After 500 scans | 0.10 | 8.8 |
| | | | After 1 hour bias stress | 0.06 | 10.0 |
| Vacuum | 35.2 | 2550 µm/ 180 µm | Initial | 0.13 | 4.9 |
| | | | After 500 scans | 0.13 | 4.9 |
| | | | After 1 hour bias stress | 0.13 | 4.6 |

Example 22

Environmental Stability of OFET Devices from Ink Jet Printing

To study their environmental stability, DRR-IV-209n (NDI-BTTZ-NDI) based flexible printed OFETs with printed Ag electrode processed by dichlorobenzene on Polyethersulfone (PES) substrates were exposed to a normal ambient condition with a relative humidity between 30 and 50%. After two weeks in air, gradual decrease of the average value of $\mu$ from $0.14\pm0.02$ cm$^2$/V to $0.09\pm0.03$ cm$^2$/Vs was observed. In threshold voltage, the positive shifts from $1.7\pm0.3$ to $4.5\pm0.7$ were observed. However, these changes on threshold voltage and mobility values were back to initial values through vacuum annealing.

Figure 29:
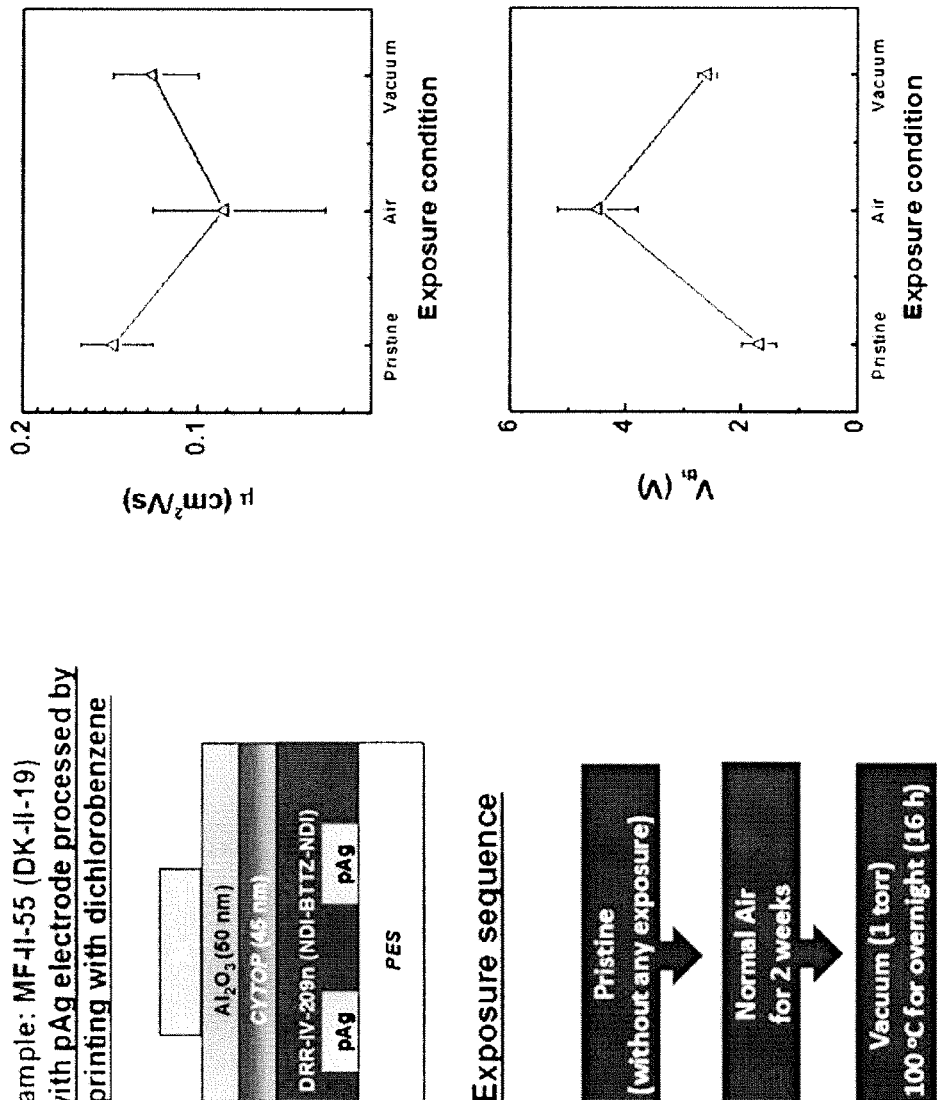
FIG. 29 illustrates air stability testing for flexible and printed OFETs.
Figure 31:
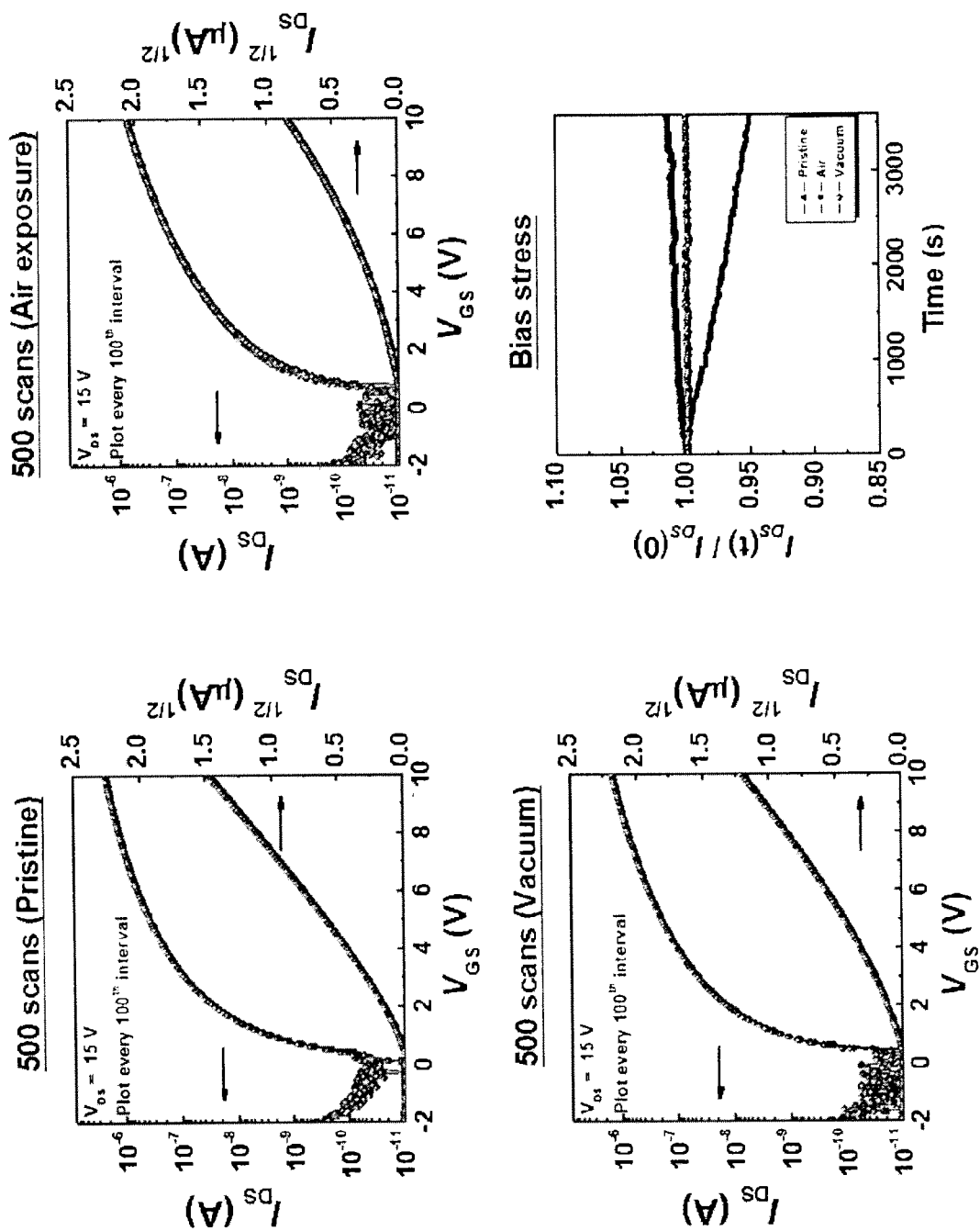
FIG. 31 illustrates electrical stability testing for flexible and printed OFETs.

FIGS. 29-31 illustrate the results. The data for air stability and electrical stability are summarized below in Tables BK-5 and BK-6.

TABLE BK-5

Air Stability

| Exposure condition | $C_{in}$ (nF/cm$^2$) at 1 kHz | $\mu$ (cm$^2$/Vs) | $V_{TH}$ (V) |
|---|---|---|---|
| Pristine | 35.2 | 0.14 ± 0.02 | 1.7 ± 0.3 |
| Air | 35.2 | 0.09 ± 0.03 | 4.5 ± 0.7 |
| Vacuum | 35.2 | 0.13 ± 0.03 | 3.5 ± 0.4 |

TABLE BK-6

Electrical stability

| Exposure condition | $C_{in}$ (nF/cm$^2$) | W/L | status | u (cm$^2$/Vs) | $V_{TH}$ (V) |
|---|---|---|---|---|---|
| Pristine | 35.2 | 2000 µm/ 180 µm | Initial | 0.17 | 1.8 |
| | | | After 500 scans | 0.17 | 1.8 |
| | | | After 1 hour bias stress | 0.17 | 1.7 |
| Air | 35.2 | 2000 µm/ 180 µm | Initial | 0.09 | 3.5 |
| | | | After 500 scans | 0.09 | 3.5 |
| | | | After 1 hour bias stress | 0.09 | 3.6 |
| Vacuum | 35.2 | 2000 µm/ 180 µm | Initial | 0.14 | 2.5 |
| | | | After 500 scans | 0.14 | 2.5 |
| | | | After 1 hour bias stress | 0.14 | 2.5 |

Conclusions

The above specification, examples and data provide exemplary description of the manufacture and use of the various compositions and devices of the inventions, and methods for their manufacture and use, and organic electronic devices comprising those compounds. In view of those disclosures, one of ordinary skill in the art will be able to envision many additional embodiments or sub-embodiments of the inventions disclosed and claimed herein to be obvious, and that they can be made without departing from the scope of the inventions disclosed herein. The claims hereinafter appended define some of those embodiments.

Additional Working Example Embodiments

Example 23

Synthesis of "Bis(CN-NDI10)BTTZ"

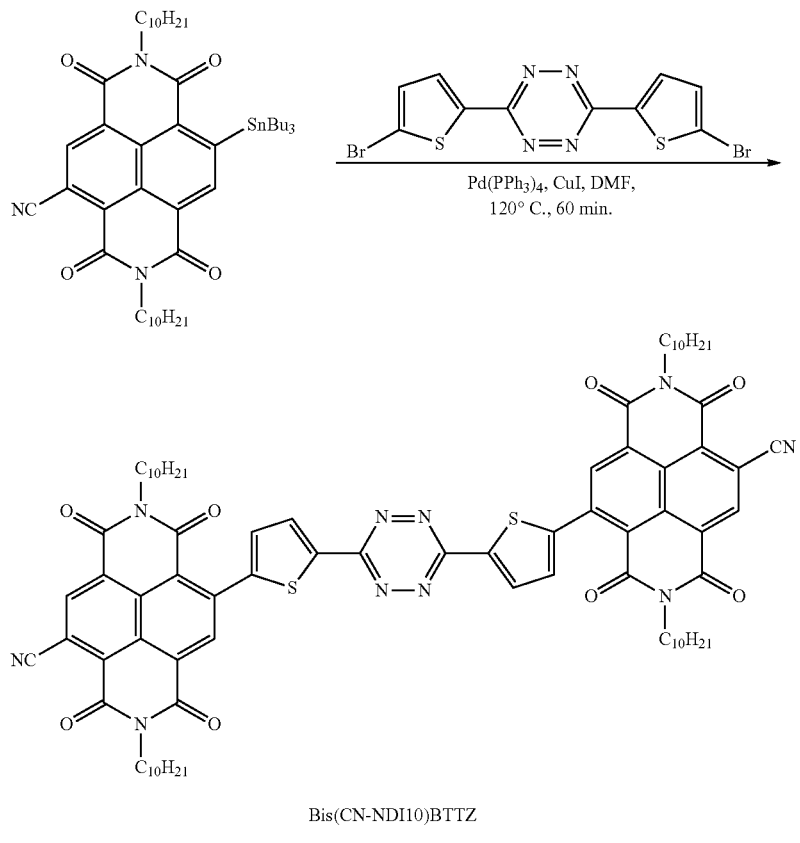

Bis(CN-NDI10)BTTZ

A solution of 3,6-bis(5-bromothiophen-2-yl)-1,2,4,5-tetrazine (0.103 g, 0.255 mmol), N,N'-di-n-decyl-2-(tri-n-butylstannyl)-6-cyano-naphthalene-1,8:4,5-bis(dicarboximide) (0.450 g, 0.523 mmol), and copper(I)iodide (0.005 g, 0.025 mmol) in DMF (5.5 mL) was degassed with nitrogen for 5 min. Tetrakis(triphenylphosphine)palladium (0.029 g, 0.025 mmol) was added and the reaction mixture was heated to 120° C. under nitrogen for 60 min. After cooling, the reaction mixture was dropped into methanol (50 mL), and red precipitate was collected by filtration. The crude product was purified by column chromatography (silica, 4% ethyl acetate in dichloromethane) and multiple recrystallizations from dichloromethane. Yield: 0.160 g (45%).

$^1$NMR (300 MHz, CDCl$_3$) δ: 9.01 (s, 2H), 8.85 (s, 2H), 8.38 (d, J=3.9 Hz, 2H), 7.42 (d, J=3.9 Hz, 2H), 4.21 (t, J=7.5 Hz, 4H), 4.11 (t, J=7.5 Hz, 4H), 1.81-1.60 (m, 8H), 1.48-1.22 (m, 58H), 0.84 (q, J=5.1 Hz, 12H). $^{13}$C{$^1$H} NMR (100 MHz, 1,1,2,2-tetrachloroethane-d$_2$, 60° C.) δ: 161.22, 160.89, 160.83, 160.58, 160.19, 146.84, 141.30, 138.27, 137.32, 135.12, 131.45, 131.05, 128.72, 128.31, 127.07, 126.43, 125.56, 123.72, 116.32, 114.22, 41.53, 41.42, 31.66, 31.65, 29.33, 29.31, 29.08, 29.06, 29.04, 27.82, 26.90, 22.47, 22.45, 13.93. LRMS (MALDI) m/z [M]$^+$ calc for 1386; found 1387. Anal. Calcd. for C$_{80}$H$_{92}$N$_{10}$O$_8$S$_2$: C, 69.34; H, 6.69; N, 10.11. Found: C, 69.11; H, 6.70; N, 9.97.

Example 24A

Synthesis of "Bis(CN-NDI)DTP & Bis(CN-NDI)"

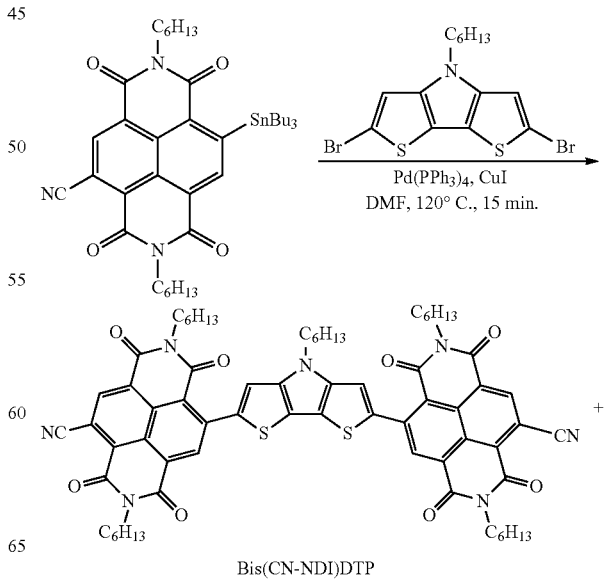

Bis(CN-NDI)DTP

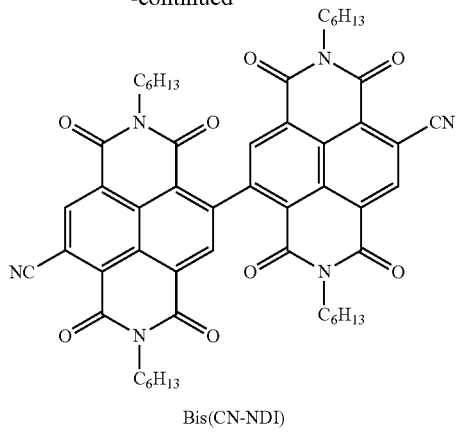

Bis(CN-NDI)

A solution of 2,6-dibromo-4-hexyl-4H-dithieno[3,2-b:2', 3'-d]pyrrole (0.08 g, 0.19 mmol), N,N'-di-n-hexyl-2-(tri-n-butylstannyl)-6-cyano-naphthalene-1,8:4,5-bis(dicarboximide) (0.30 g, 0.385 mmol), and copper(I)iodide (0.004 g, 0.019 mmol) in DMF (3.0 mL) was degassed with nitrogen for 10 min. Tetrakis(triphenylphosphine)palladium (0.022 g, 0.019 mmol) was added and the reaction mixture was then heated at 120° C. under nitrogen for 15 min. After cooling, the reaction mixture was diluted with methanol (30 mL), and a green precipitate was collected by filtration. The crude products were separated by column chromatography (silica gel) with $CH_2Cl_2$ as eluent to afford bis(CN-NDI) a yellow solid (0.056 g, 32%), while bis(CN-NDI)DTP was eluted with 2% ethyl acetate in dichloromethane to yield a green solid (0.096 g, 43%).

Bis(CN-NDI)DTP: $^1$H NMR (300 MHz, $CDCl_3$) δ 8.954 (s, 2H), 8.951 (s, 2H), 7.46 (s, 2H), 4.28 (t, J=6.9 Hz, 2H), 4.21 (t, J=7.8 Hz, 4H), 4.14 (t, J=7.5 Hz, 4H), 2.00-1.91 (q, J=3.5 Hz, 2H), 1.79-1.64 (m, 8H), 1.43-1.23 (m, 30H), 0.90-0.84 (m, 15H). $^{13}$C NMR {1H} NMR (100 MHz, $CDCl_3$) δ 161.94, 161.76, 161.37, 160.92, 146.81, 143.75, 139.97, 138.21, 135.47, 129.92, 128.49, 127.07, 126.27, 125.33, 121.95, 120.10, 116.88, 114.45, 113.64, 48.12, 41.87, 31.84, 31.80, 30.75, 28.33, 28.26, 27.19, 27.10, 27.05, 22.92, 22.88, 14.38 (Five aliphatic carbon signals were not observed due to overlapping resonances). HRMS (MALDI) m/z calcd for $C_{68}H_{71}N_7O_8S_2$, (MH$^+$), 1178.482; found, 1178.488. Anal. Calcd. for $C_{68}H_{71}N_7O_8S_2$: C, 69.30; H, 6.07; N, 8.31. Found: C, 69.18; H, 5.98; N, 8.36.

Bis(CN-NDI): $^1$H NMR (300 MHz, $CDCl_3$) δ 9.03 (s, 2H), 8.52 (s, 2H), 4.2 (t, J=7.7, 4H), 3.92 (t, J=7.7, 4H), 1.70-1.61 (m, 4H), 1.21-1.53 (m, 28H), 0.88 (t, J=6.9, 6H), 0.79 (t, J=6.9 Hz, 6H). $^{13}$C {1H} NMR (100 MHz, $CDCl_3$) δ 162.39, 161.48, 161.23, 160.69, 148.27, 135.66, 133.79, 129.04, 128.71, 127.39, 126.83, 126.81, 122.80, 116.60, 114.93, 42.01, 41.67, 31.76, 31.64, 28.23, 28.10, 27.03, 26.91, 22.86, 22.81, 14.35, 14.26. HRMS (EI) m/z calcd for $C_{54}H_{56}N_6O_8$, (M$^+$), 916.4152; found, 916.4160. Anal. Calcd. for $C_{54}H_{56}N_6O_8$: C, 70.72; H, 6.15; N, 9.16. Found: C, 70.67; H, 6.24; N, 9.12.

Example 24B

In a related example, Bis(CN-NDI)DTP was prepared except that the hexyl groups on the NDI moiety was replaced by the fluorinated alkyl group, $C_3F_7$ (called Bis(NDI-$C_3F_7$) DTP). This fluorinated compound was more easily reduced (−0.21V) than its alkylated version.

Example 25

Synthesis of "Bis(CN-NDI12)BTTZ"

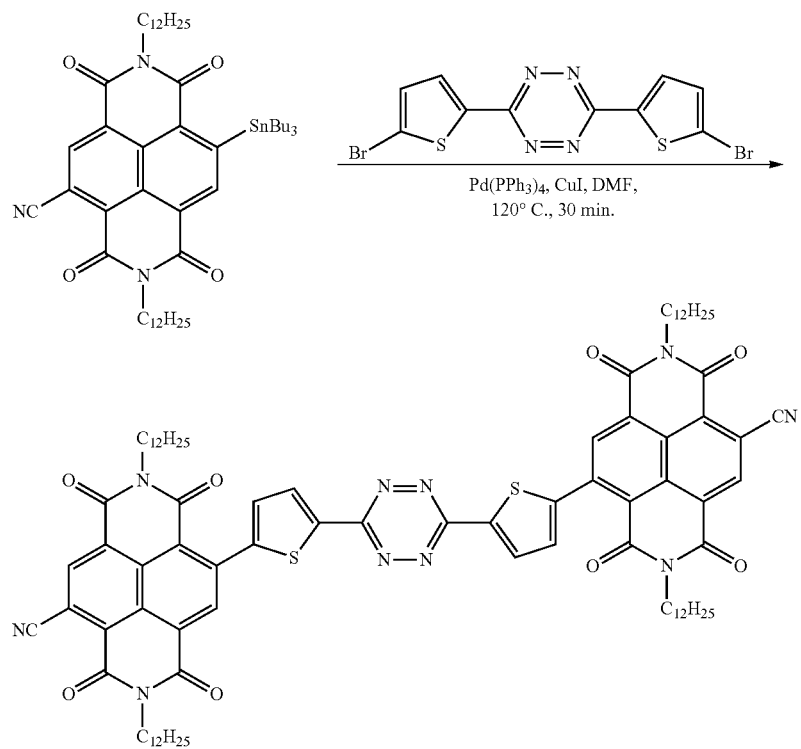

Bis(CN-NDI12)BTTZ

A solution of 3,6-bis(5-bromothiophen-2-yl)-1,2,4,5-tetrazine (0.064 g, 0.158 mmol), N,N'-di-n-dodecyl-2-(tri-n-butylstannyl)-6-cyano-naphthalene-1,8:4,5-bis(dicarboximide) (0.297 g, 0.325 mmol), and copper(I)iodide (0.002 g, 0.008 mmol) in DMF (3.5 mL) was degassed with nitrogen for 5 min. Tetrakis(triphenylphosphine)palladium (0.018 g, 0.025 mmol) was added and the reaction mixture was heated to 120° C. under nitrogen for 30 min. After cooling, the reaction mixture was dropped into methanol (60 mL), and red precipitate was collected by filtration. The crude product was purified by column chromatography (silica gel, 3% ethyl acetate in chloroform). The desired product was further purified by size-exclusion column chromatography with $CHCl_3$ as eluent, followed by recrystallization from dichloromethane. Yield: 0.110 g (46%).

$^1$H NMR (300 MHz, $CDCl_3$) δ: 9.01 (s, 2H), 8.85 (s, 2H), 8.37 (d, J=3.6 Hz, 2H), 7.42 (d, J=3.9 Hz, 2H), 4.20 (t, J=7.5 Hz, 4H), 4.13 (t, J=7.5 Hz, 4H), 1.80-1.62 (m, 8H), 1.47-1.10 (m, 72H), 0.84 (t, J=3.9 Hz, 12H). $^{13}$C {1H} NMR (100 MHz, $CDCl_3$, 40° C.) δ: 161.43, 161.16, 161.07, 160.77, 160.34, 147.00, 141.58, 138.39, 137.01, 135.26, 131.30, 130.44, 128.84, 128.54, 127.26, 126.65, 125.80, 124.05, 116.21, 114.67, 41.64, 41.59, 31.89, 29.61, 29.60, 29.56, 29.54, 29.50, 29.31, 29.30, 29.26, 27.98, 27.06, 27.04, 22.64, 14.03. HRMS (MALDI) m/z calcd for $C_{88}H_{108}N_{10}O_8S_2$, (M+2H$^+$), 1498.7950; found, 1498.7874. Anal. Calcd. for $C_{88}H_{108}N_{10}O_8S2$: C, 70.56; H, 7.27; N, 9.35. Found: C, 70.26; H, 7.38; N, 9.30

Example 26

Synthesis of "NDI-TzTz-NDI"

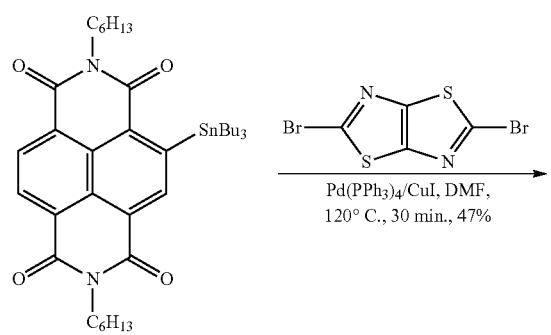

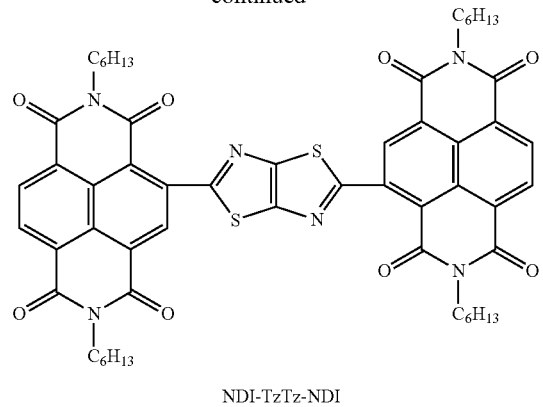

NDI-TzTz-NDI

A solution of 2,5-dibromothiazolo[5,4-d]thiazole (0.18 g, 0.60 mmol), N,N'-di-n-hexyl-2-(tri-n-butylstannyl)-naphthalene-1,8:4,5-bis(dicarboximide) (0.89 g, 1.23 mmol), and copper(I)iodide (0.006 g, 0.03 mmol) in DMF (12.5 mL) was degassed with nitrogen for 5 min. Tetrakis(triphenylphosphine)palladium (0.07 g, 0.06 mmol) was added and the reaction mixture was then heated at 120° C. under nitrogen for 30 min. After cooling, the reaction mixture was diluted with methanol (30 mL), and reddish brown precipitate was collected by filtration. The crude product was purified by column chromatography (silica gel, 3% ethyl acetate in chloroform) and size-exclusion column chromatography (S-X1 Bio beads, $CHCl_3$) to afford NDI-TzTz-NDI as an orange solid. Yield: 0.28 g (47%).

$^1$H NMR (300 MHz, $CDCl_3$) δ: 8.91 (s, 2H), 8.85 (d, J=7.5 Hz, 2H), 8.81 (d, J=7.5 Hz, 2H), 4.19 (t, J=7.8 Hz, 4H), 4.11 (t, J=7.8 Hz, 4H), 1.78-1.63 (m, 8H), 1.48-1.20 (m, 24H), 0.90-0.83 (m, 12H). $^{13}$C {1H} NMR (75 MHz, $CDCl_3$) δ 166.42, 162.52, 162.20, 162.06, 161.80, 152.30, 138.12, 134.37, 131.97, 131.91, 127.30, 127.12, 127.05, 126.73, 125.86, 124.76, 41.36, 41.13, 31.48, 28.01, 27.97, 26.75, 26.72, 22.57, 22.55, 14.05, 14.03 (one carbon signal was not observed due to overlap). HRMS (MALDI) m/z calcd for $C_{56}H_{58}N_6O_8S_2$, (MH$^+$), 1007.3836; found, 1007.3799. Anal. Calcd. for $C_{56}H_{58}N_6O_8S_2$: C, 66.78; H, 5.80; N, 8.34. Found: C, 66.63; H, 5.69; N, 8.39. DSC (° C.): 160 ($T_g$), 290 ($T_m$); TGA (° C.): 404 ($T_d$)

TABLE 1a

Summary of CV$^a$ data for NDI-based oligomers.

| Example | Structure | X | $E_{1/2}^{+/0}$ (V) | $E_{1/2}^{0/2-}$ (V) | $E_{1/2}^{2-/4-}$ (V) |
|---|---|---|---|---|---|
| 26 | NDI-X-NDI | TzTz | N/A | −0.96 | −1.40 |
| 23 | Bis(CN-NDI10)-X | BTTZ$^b$ | N/A | −0.76 | −1.28 |
| 24 | Bis(CN-NDI)-X | DTP | 0.65 | −0.75, −0.82 | −1.26 |

$^a$0.1M $^n$Bu$_4$NPF$_6$/CH$_2$Cl$_2$ in V vs FeCp$_2^{+/0}$;
$^b$THF

Example 27

Preparation of OFET Devices Using Spin Coating

Bottom contact top gate OFETs with a $CYTOP/Al_2O_3$ dielectric bilayer, as shown in FIG. 13, but with Au or Au/Ti electrodes in place of the Au or Al electrodes of FIG. 13 were prepared via spin coating in the same manner as Example 19.

Figure 33C:
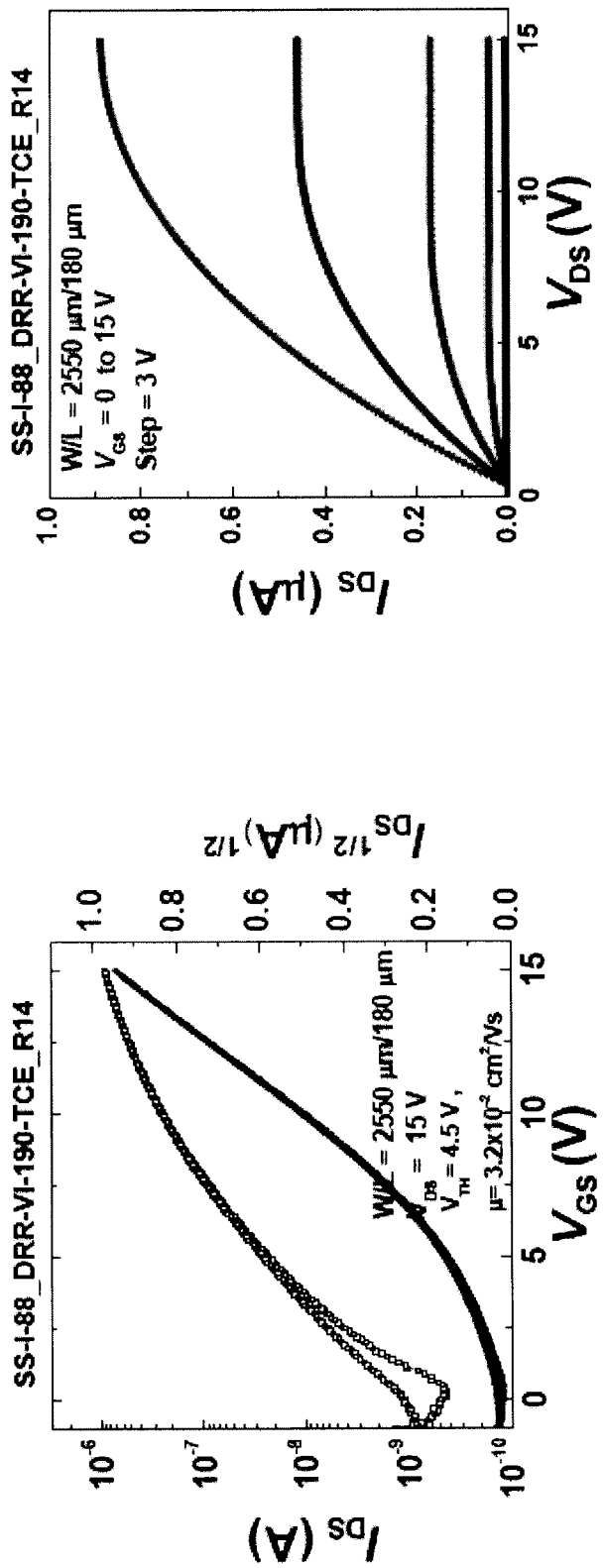
FIG. 33c illustrates OFET results for NDI-Tz-Tz-NDI in Table 2a, No. 6.

The results are summarized in Table 2a and FIGS. 32 and 33.

TABLE 2a

Summary of device data for NDI-based oligomers.

| No. | Compound | W/L | $C_{in}$ (nF/cm$^2$) | Solvent | S/D electrode | μ (cm$^2$/Vs) | $V_{TH}$ (V) | $I_{on/off}$ |
|---|---|---|---|---|---|---|---|---|
| 1 | Bis(CN-NDI)DTP | 2550 μm/180 μm | 35.2 | 1,1,2,2 tetrachloroethane | Au/Ti | 0.18 (±0.01) | 5.4 (±0.1) | $2 \times 10^3$ |
| 2 | Bis(CN-NDI)DTP | 2550 μm/180 μm | 35.2 | Orth xylene | Au/Ti | NO FET behavior | | |
| 3 | Bis(CN-NDI)DTP | 2550 μm/180 μm | 35.2 | chloroform | Au | $5.2 (\pm1.7) \times 10^{-3}$ | 4.1 (±0.3) | $1 \times 10^3$ |
| 4 | Bis(CN-NDI)DTP | 2550 μm/180 μm | 35.2 | chlorobenzene | Au | $1.3 (\pm0.1) \times 10^{-2}$ | 5.62 (±0.04) | $3 \times 10^3$ |
| 5 | NDI-Tz-Tz-NDI | 2550 μm/180 μm | 35.2 | chloroform | Au | $1.6 (\pm0.2) \times 10^{-2}$ | 6.1 (±0.9) | $1 \times 10^3$ |
| 6 | NDI-Tz-Tz-NDI | 2550 μm/180 μm | 35.2 | chlorobenzene | Au | 0.11 (±0.01) | 6 (±1) | $2 \times 10^4$ |
| 7 | NDI-Tz-Tz-NDI | 2550 μm/180 μm | 35.2 | 1,1,2,2 tetrachloroethane | Au | $2.7 (\pm0.3) \times 10^{-2}$ | 3.4 (±0.6) | $2 \times 10^3$ |

Example 28

Preparation of OFET Devices for NDI-Based Oligomers and Blends

Figure 34A:
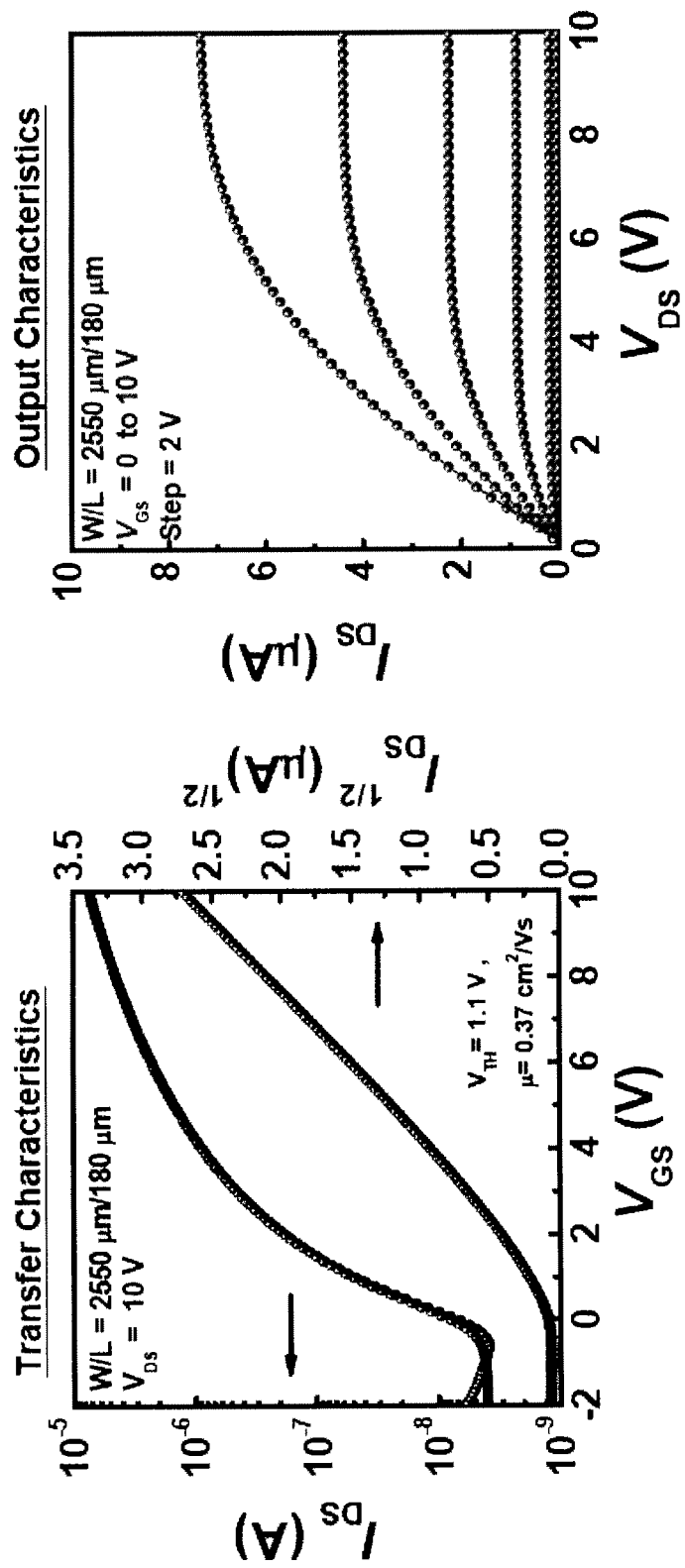
FIG. 34a illustrates OFET results for Bis(CN-NDI12) BTTZ in Table 3a, No. 1.
Figure 34B:
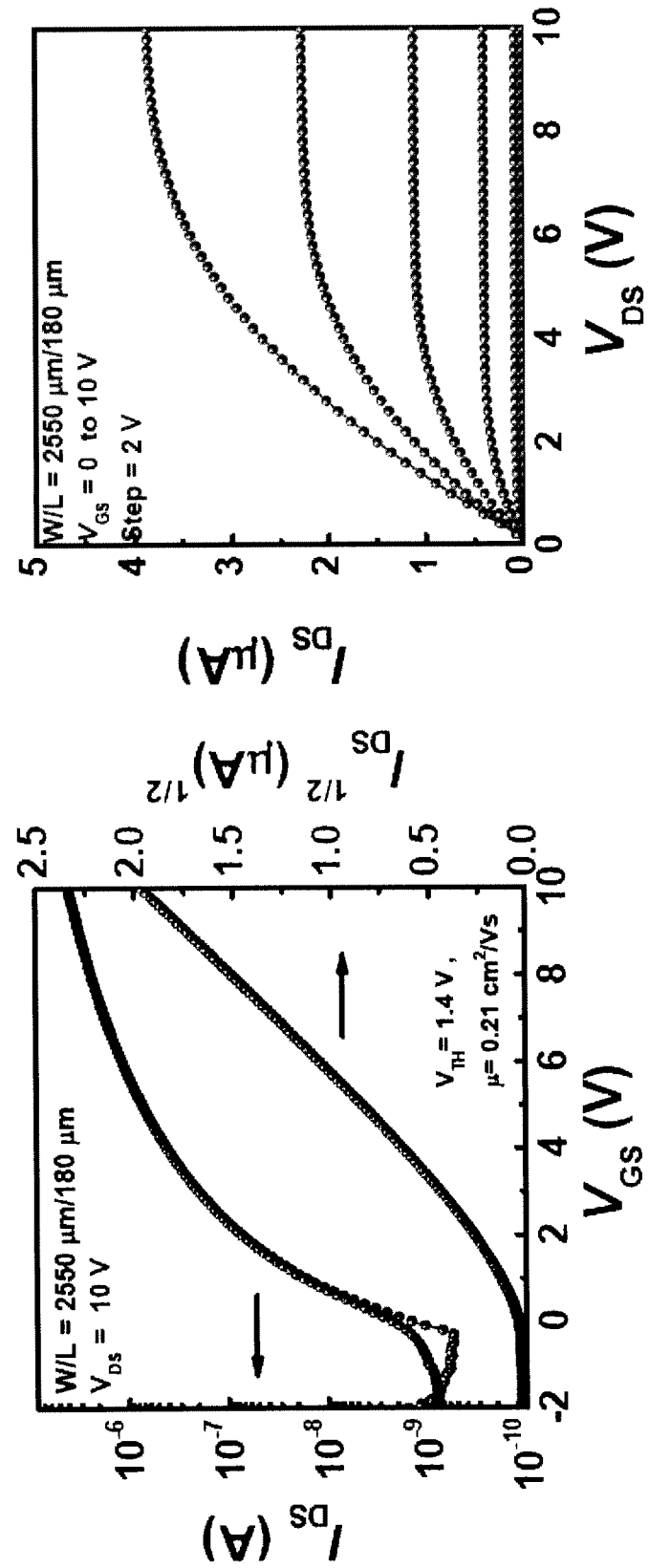
FIG. 34b illustrates OFET results for Bis(CN-NDI12) BTTZ/PS blend in Table 3a, No. 2.
Figure 35A:
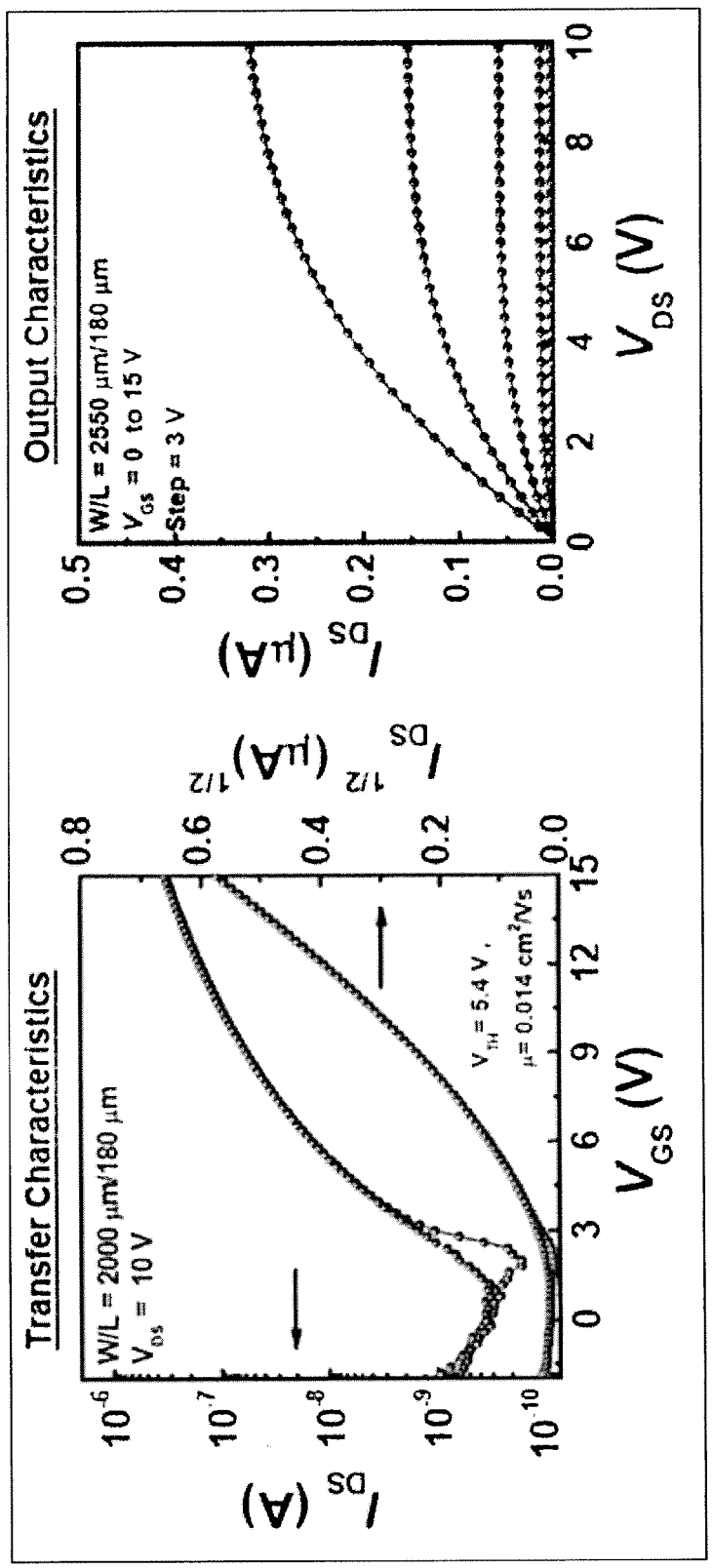
FIG. 35a illustrates OFET results for Bis(CN-NDI)DTP in Table 3a, No. 3.
Figure 35B:
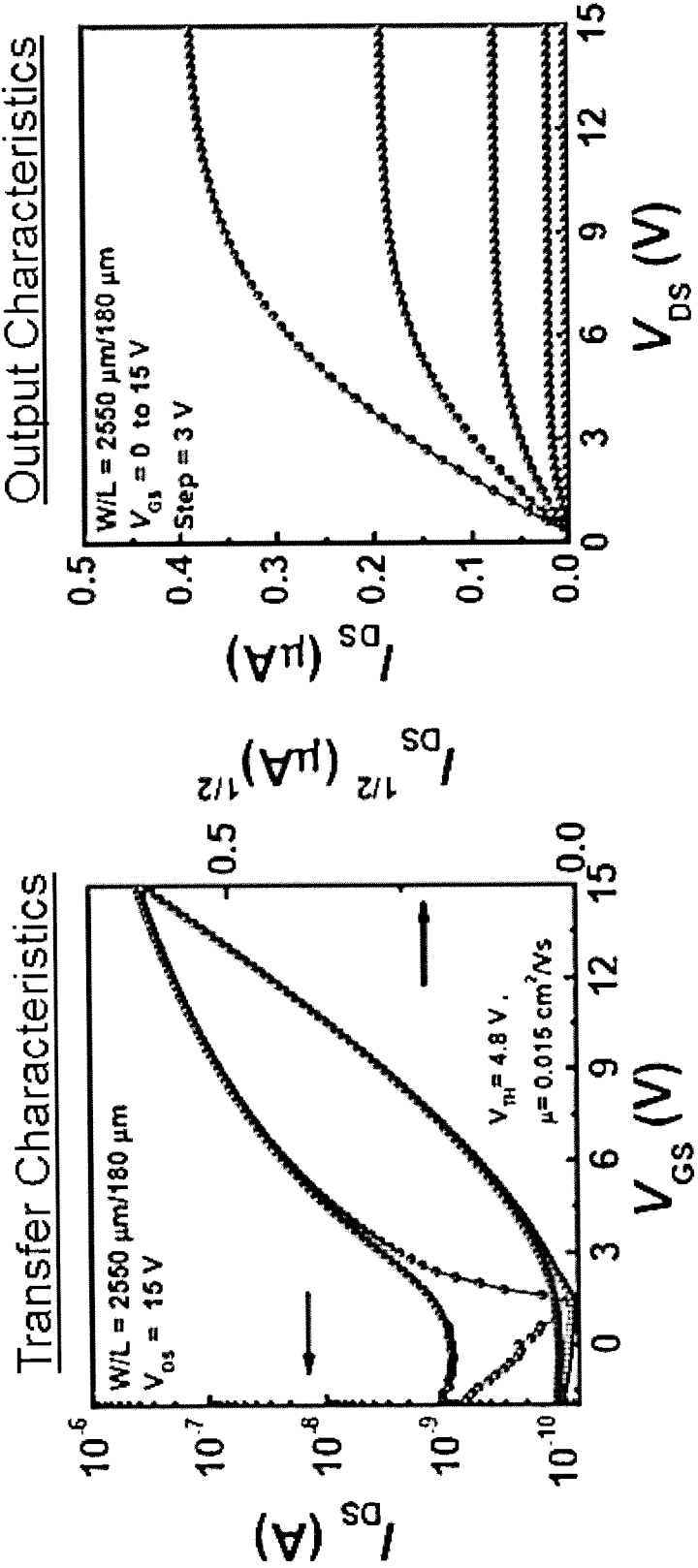

Bottom contact top gate OFETs with a CYTOP/Al$_2$O$_3$ dielectric bilayer, as shown in FIG. 13, but with Au or Au/Ti electrodes in place of the Au or Al electrodes of FIG. 13 were prepared via spin coating in the same manner as Example 19. The semiconductor layers, summarized in Table 3a, were also prepared as a blend composition with polystyrene (M$_w$: 390 kDa) ("PS"). Table 3a summarizes the results obtained in the same manner as obtained in Example 19. FIGS. 34-35 also demonstrates the device performance.

TABLE 3a

Summary of device data for NDI-based oligomers and blends.

| No. | Compound | W/L | $C_{in}$ (nF/cm$^2$) | Solvent | S/D electrode | μ (cm$^2$/Vs) | $V_{TH}$ (V) | $I_{on/off}$ |
|---|---|---|---|---|---|---|---|---|
| 1 | Bis(CN-NDI12) BTTZ | 2550 μm/180 μm | 35.2 | Dichlorobenzene (20 mg/ml) | Au | 0.28 (±0.11) | 1.3 (±0.1) | $10^3$ |
| 2 | Bis(CN-NDI12) BTTZ/PS$^a$ (1:1 ratio) | 2550 μm/180 μm | 35.2 | Dichlorobenzene (10 mg/ml) | Au | 0.20 (±0.2) | 1.4 (±0.1) | $10^3$ |
| 3 | Bis(CN-NDI) DTP | 2550 μm/180 μm | 35.2 | Dichlorobenzene (20 mg/ml) | Au/Ti | 0.011 (±0.003) | 5.1 (±0.7) | $10^3$ |
| 4 | Bis(CN-NDI) DTP/PS$^a$ (1:1 ratio) | 2550 μm/180 μm | 35.2 | Dichlorobenzene (20 mg/ml) | Au/Ti | 0.013(±0.001) | 5.2 (±0.2) | $10^3$ |

$^a$PS = polystyrene (M$_w$: 390 kDa)

Example 29

Environmental Stability of OFET Devices

Figure 36:
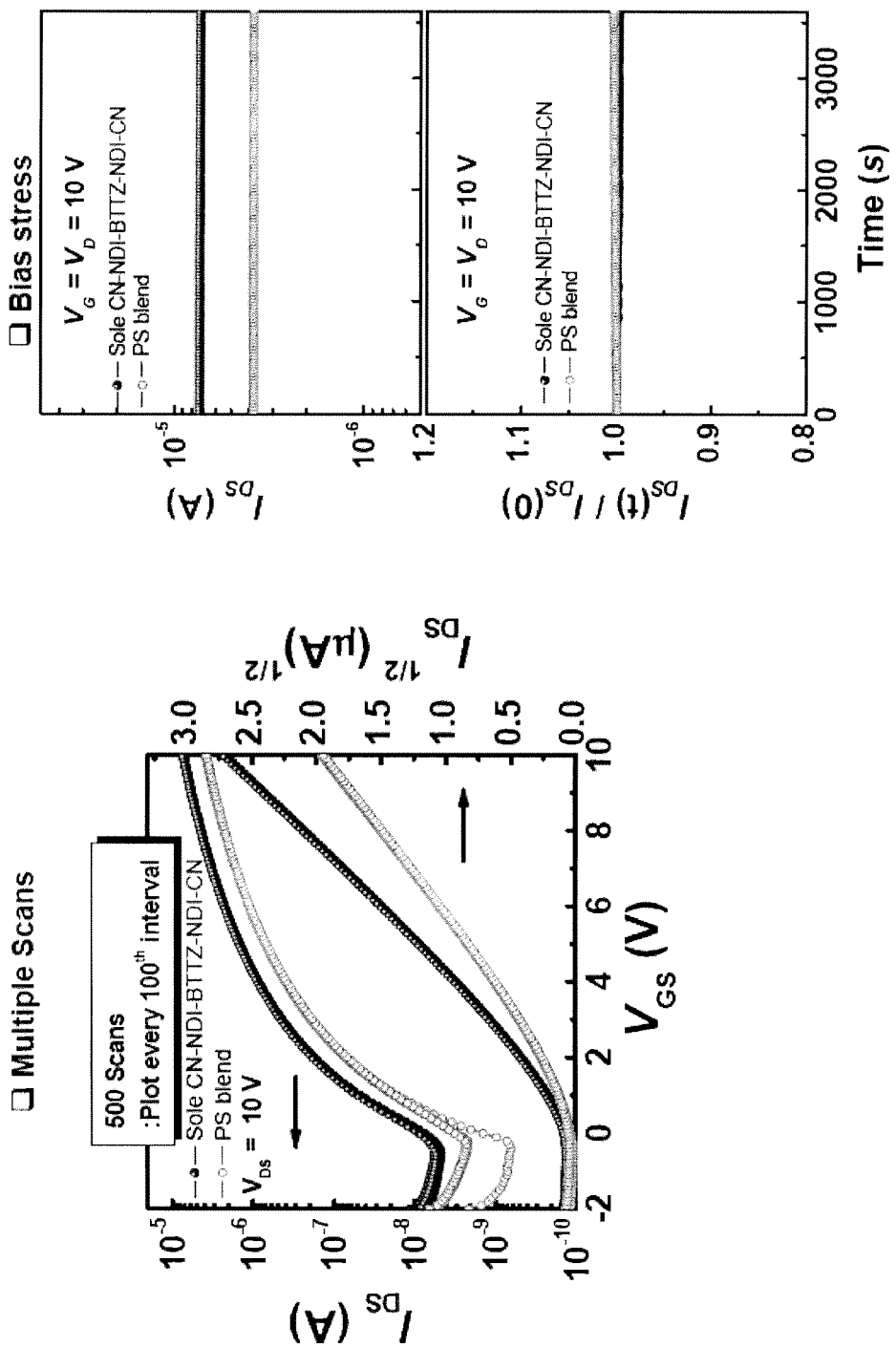
FIG. 36 illustrates the operational stability of Bis(CN-NDI12) BTTZ and Bis(CN-NDI12) BTTZ/PS blend.
Figure 38B:
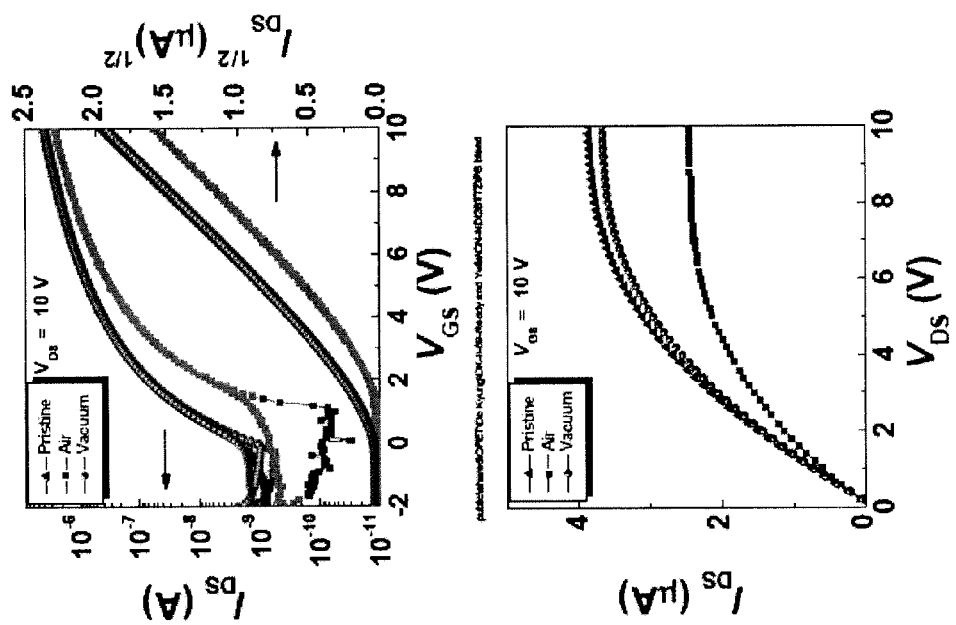
FIG. 38 illustrates OFET performance with respect to air stability of Bis(CN-NDI12) BTTZ and Bis(CN-NDI12) BTTZ/PS blend.
Figure 38A:
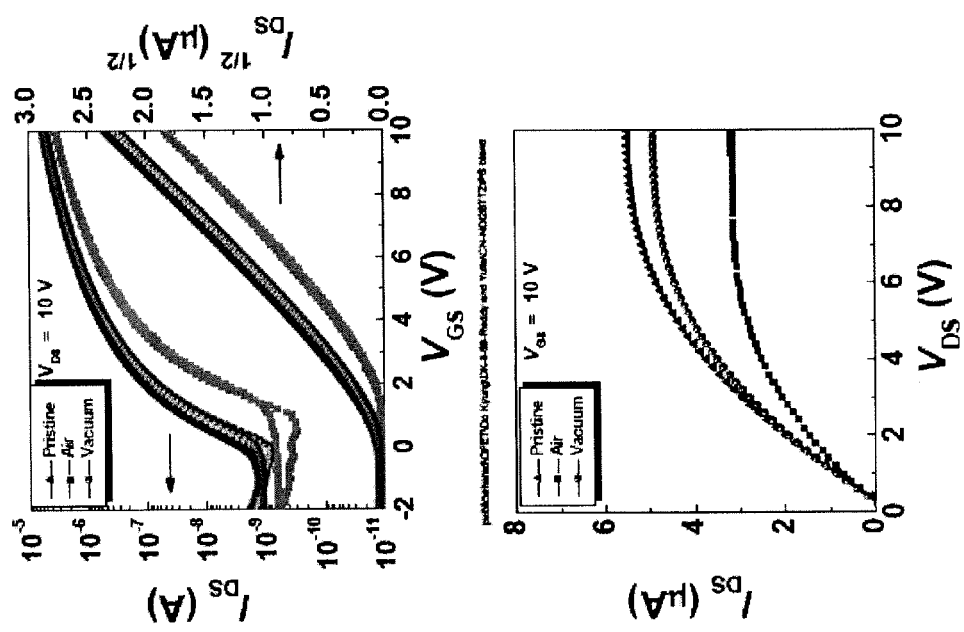

To study their environmental stability, the Bis(CN-NDI12) BTTZ and Bis(CN-NDI12) BTTZ/PS devices of Example 28 were exposed to a normal ambient condition with a relative humidity between 30 and 50%. After two weeks in air, gradual decrease of the average value of μ was observed, as summarized in Table 4a and FIGS. 36-38.

Figure 39B:
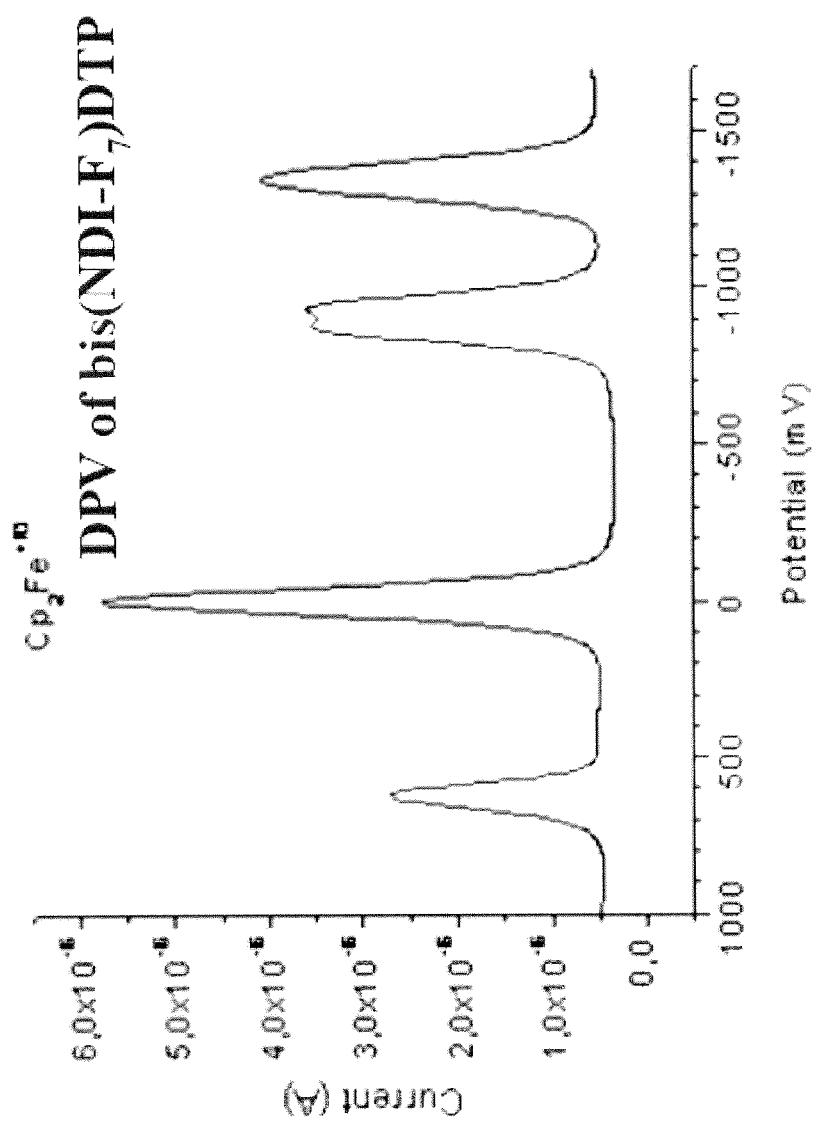
FIG. 39b illustrates DPV results for Bis(NDI-F7)DTP.
Figure 40A:
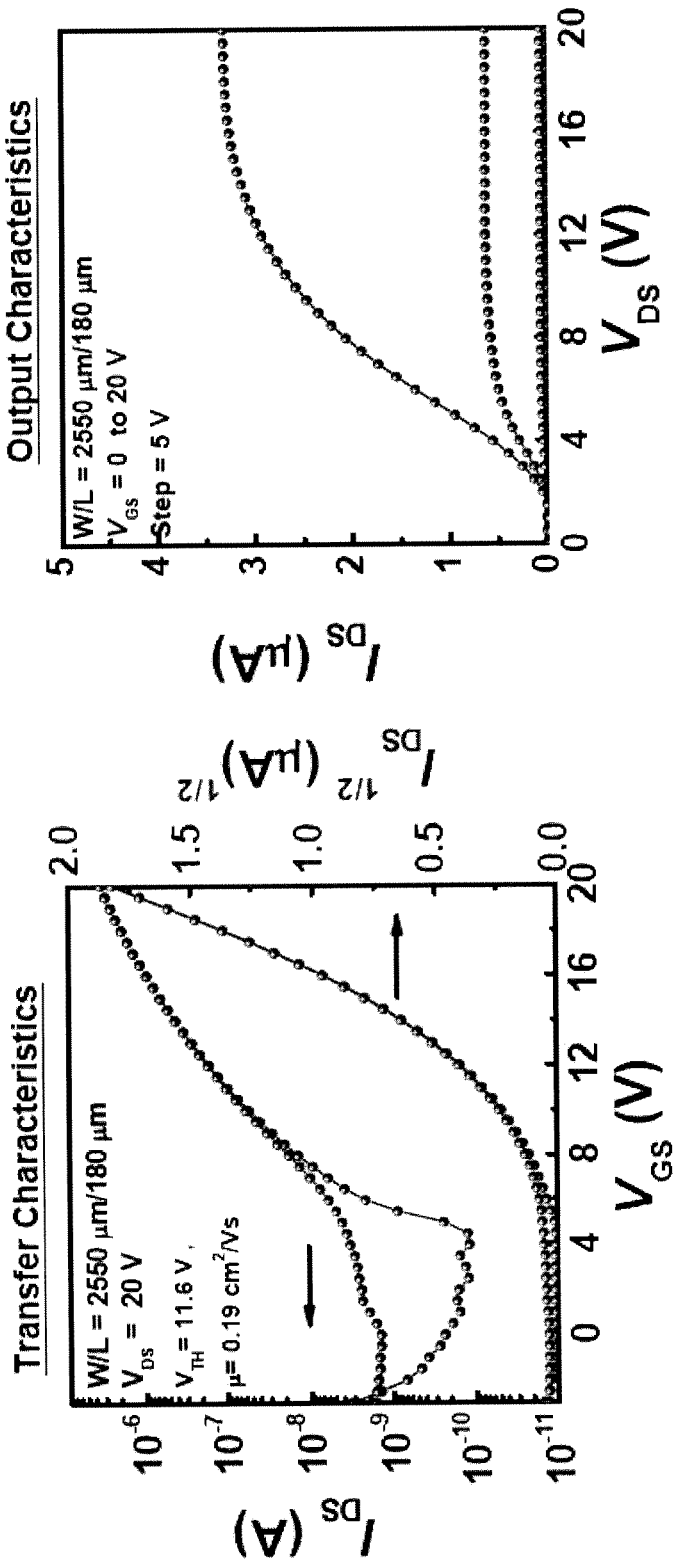
FIG. 40a-e illustrates OFET results from devices utilizing five different mono-ketone bridge NDI semiconducting compounds.
Figure 40B:
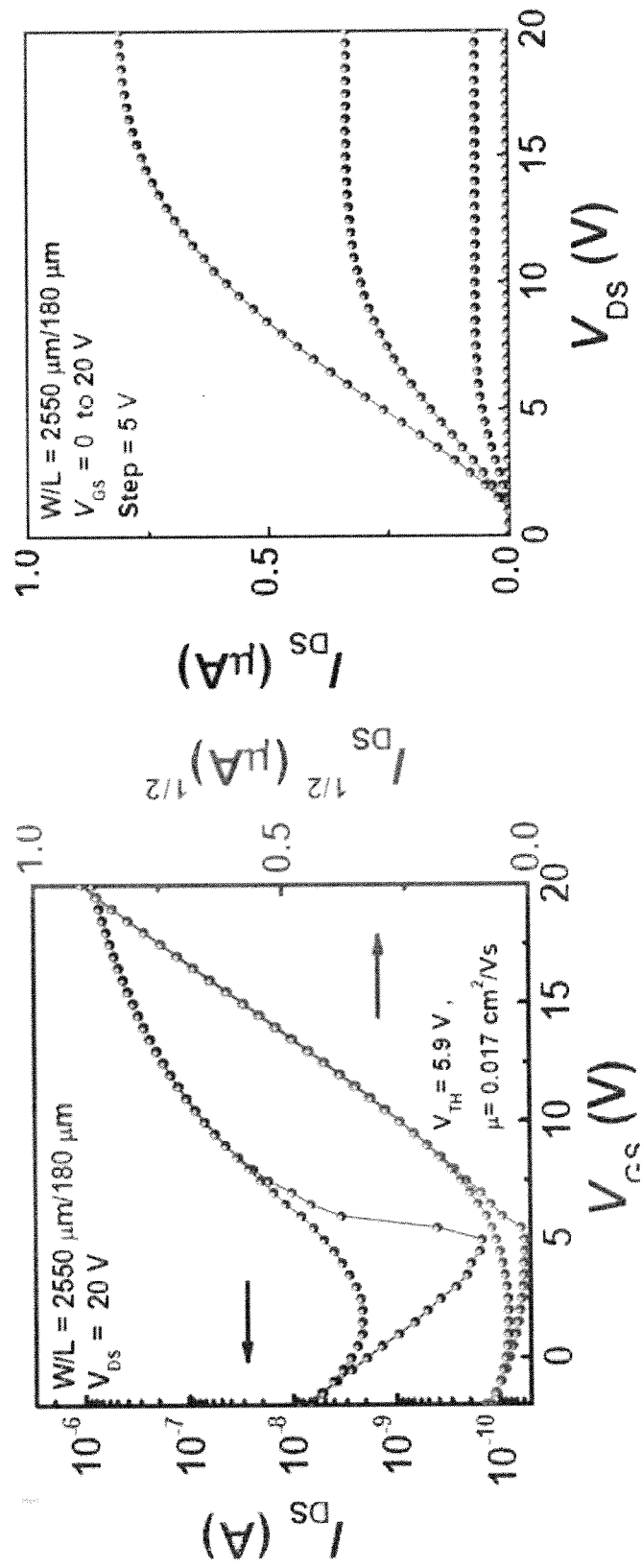
Figure 40C:
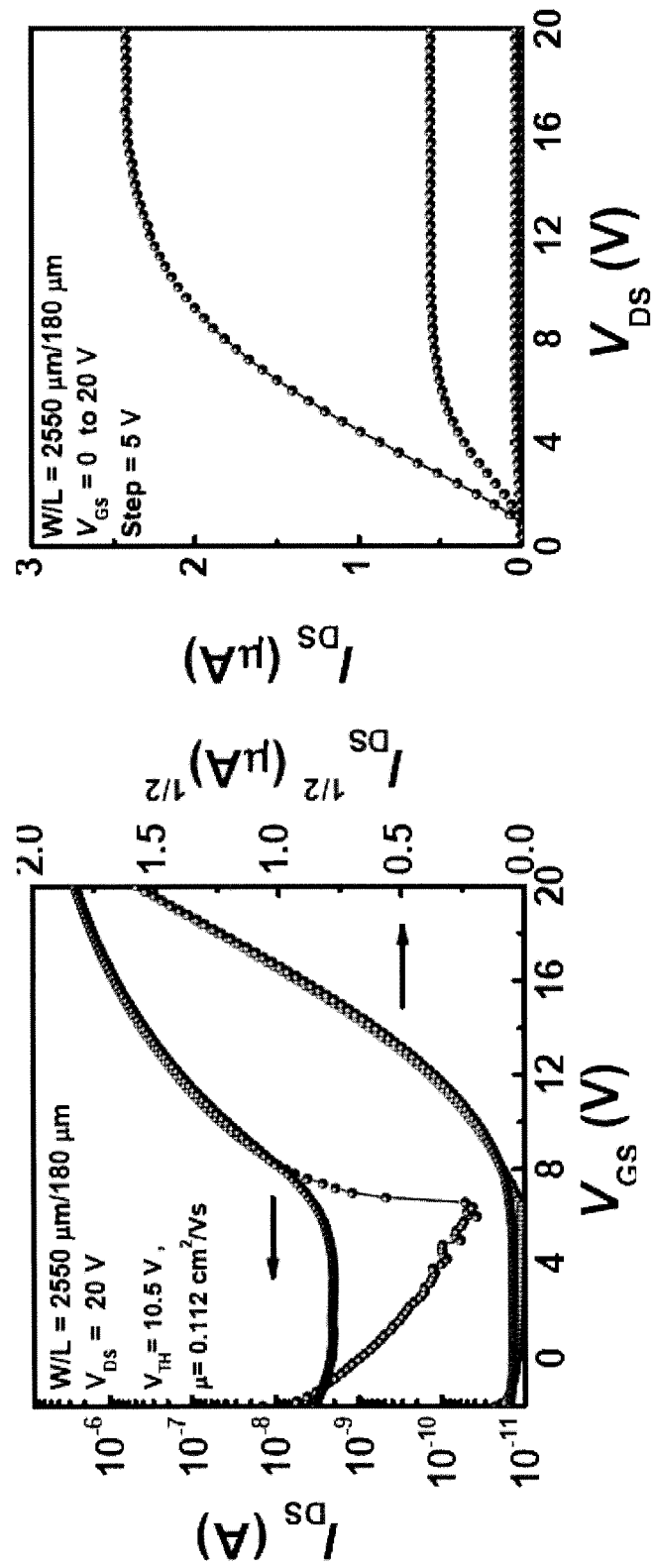
Figure 40D:
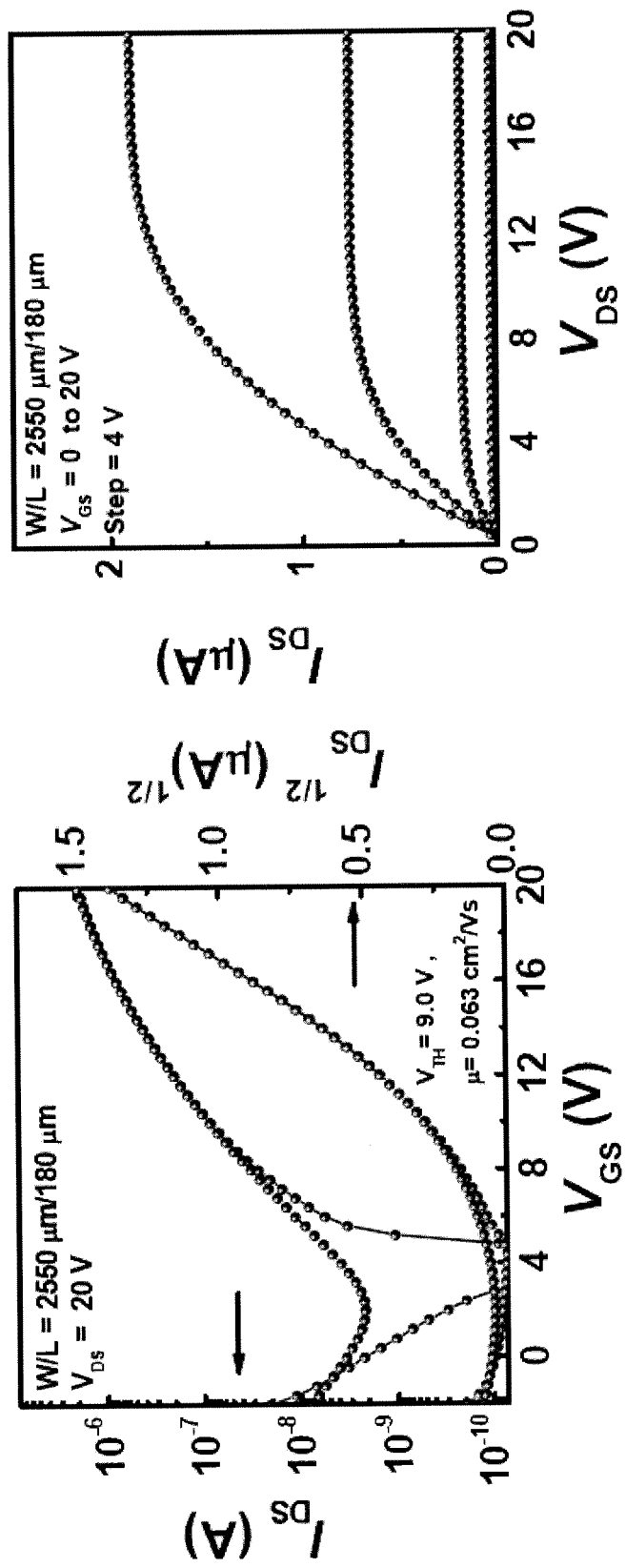
Figure 40E:
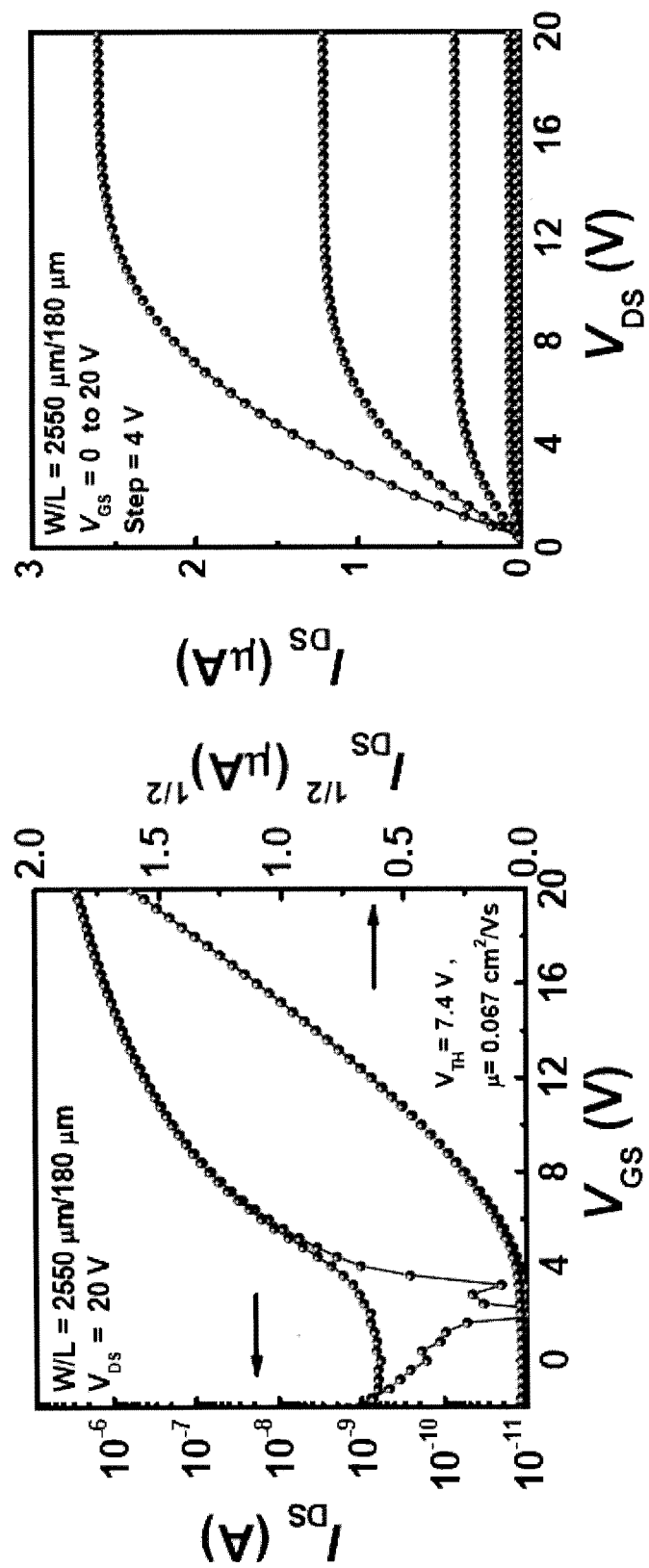
Figure 41A:
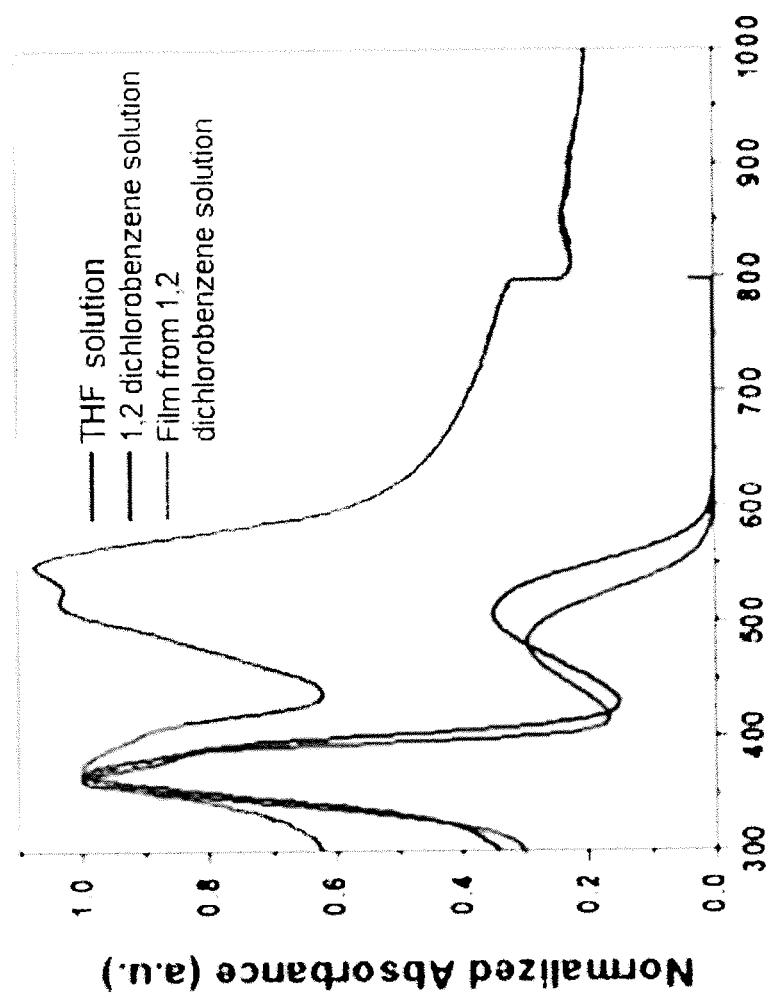
FIG. 41a illustrates absorbace from device utilizing Bis (CN-NDI12) BTTZ semiconductor.
Figure 41B:
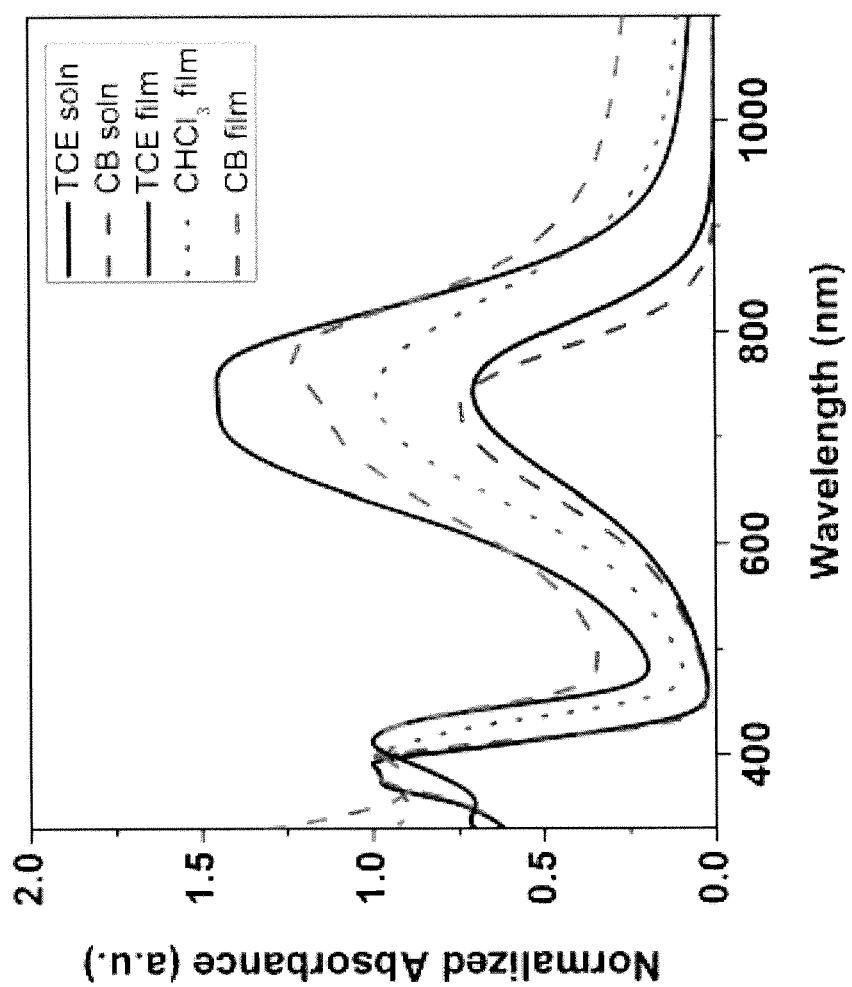
FIG. 41b illustrates absorbace from device utilizing Bis(CN-NDI)DTP semiconductor.
Figure 41C:
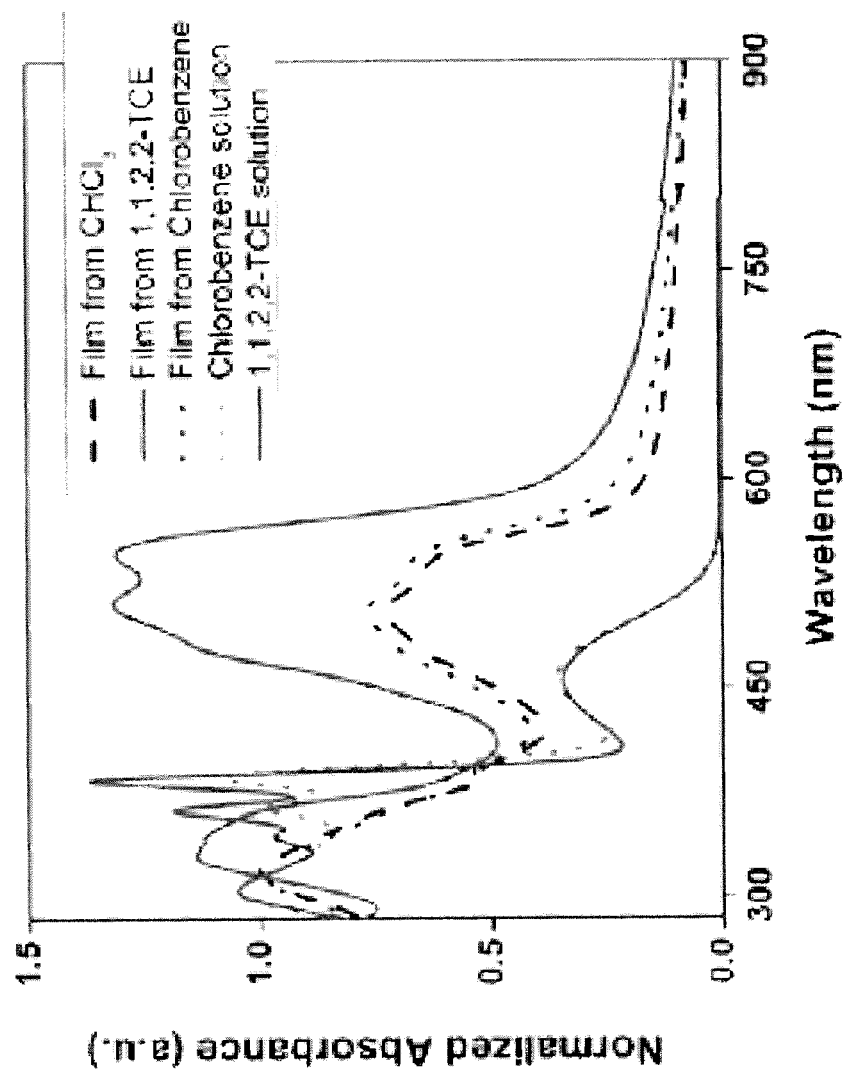
FIG. 41c illustrates absorbace from device utilizing NDI-Tz-Tz-NDI semiconductor.

Bis(NDI-F7)DTP was prepared in the same manner as NDI-DTP-NDI in Example 6, however, the corresponding NDI starting material contained —$CH_2C_3F_7$ N-substitution. Bis(NDI-F7)DTP was analyzed by DPV (0.1 M $nBu_4$ $NPF_6$/$CH_2Cl_2$ in V vs. $FeCp_2^{+/0}$) and found to have $E_{1/2}$ ($DTP^{+/0}$): 0.62; $E_{1/2}$ ($NDI^{0/-}$): −0.88(1), −0.93(1); $E_{1/2}$ ($NDI^{-/2-}$): −1.34 (2). The results are summarized in Table 5a and FIG. 39.

TABLE 5a

Summary of device data for NDI-based oligomers.

| No. | Compound | W/L | $C_{in}$ (nF/cm$^2$) | Solvent | S/D electrode | μ (cm$^2$/Vs) | $V_{TH}$ (V) | $I_{on/off}$ |
|---|---|---|---|---|---|---|---|---|
| 1 | Bis(NDI-F7) DTP | 2550 μm/ 180 μm | 35.2 | 1,1,2,2 tetrachloroethane | Au | 2.9 × 10$^{-4}$ | 4.3 | 3 × 10$^2$ |
| 2 | Bis(NDI-F7) DTP | 2550 μm/ 180 μm | 35.2 | 1,1,2,2 tetrachloroethane | Au | 1.9 (±0.7) × 10$^{-4}$ | 3.9 (±0.4) | 3 × 10$^2$ |

TABLE 4a

Summary of air stability

| | Bis(CN-NDI12) BTTZ | | | Bis(CN-NDI12) BTTZ/PS[a] (1:1 ratio) | | |
|---|---|---|---|---|---|---|
| Conditions | $C_{in}$ (nF/cm$^2$) | μ (cm$^2$/Vs) | $V_{TH}$ (V) | | μ (cm$^2$/Vs) | $V_{TH}$ (V) |
| Pristine | 35.2 | 0.28 (±0.11) | 1.3 (±0.1) | | 0.20 (±0.02) | 1.5 (±0.1) |
| Air (2 weeks) | 35.2 | 0.23 (±0.12) | 2.7 (±0.2) | | 0.17 (±0.01) | 2.6 (±0.5) |
| Vacuum | 35.2 | 0.26 (±0.13) | 1.7 (±0.1) | | 0.18 (±0.02) | 1.5 (±0.1) |

[a]PS = polystyrene ($M_w$: 390 kDa)

Example 30

Electrochemical Properties of Bis(NDI-F$_7$)DTP

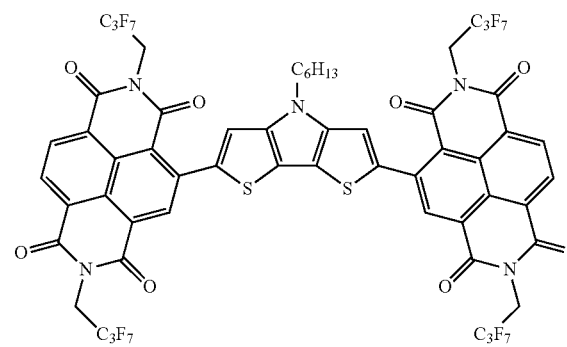

0.05 g, $^1$H, $^{13}$C, MALDI. EA
Bis(NDI-C$_3$F$_7$)DTP

Example 31

Electrochemical Properties of Additional Compounds

The following five compounds were made by selecting the appropriate NDI precursor and mono-ketone bridge precursor according to the synthetic methods disclosed herein. The compounds were then used as semiconducting material in devices built in the same manner as Example 19. The results are summarized in Table 6a and FIG. 40.

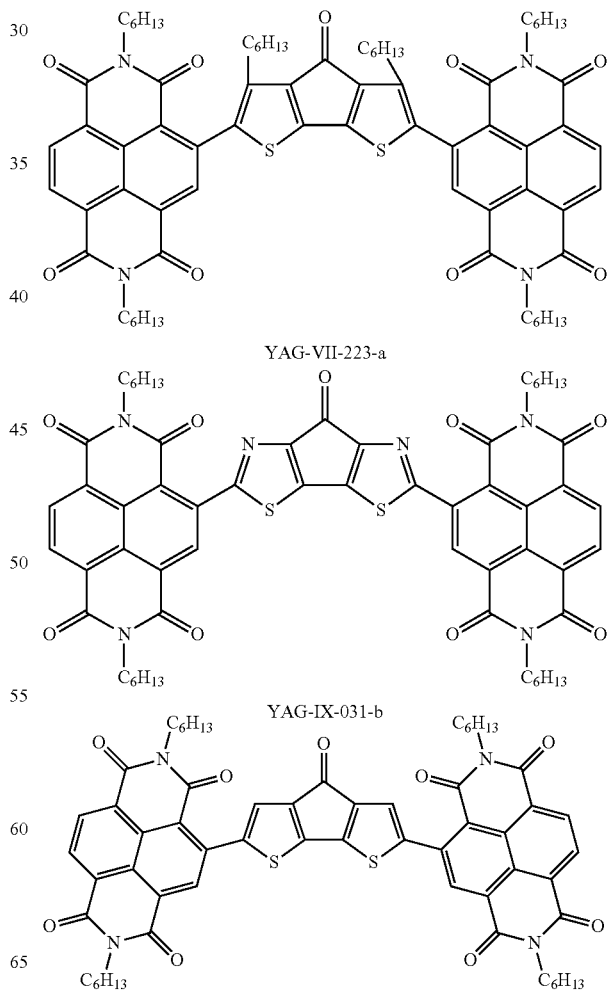

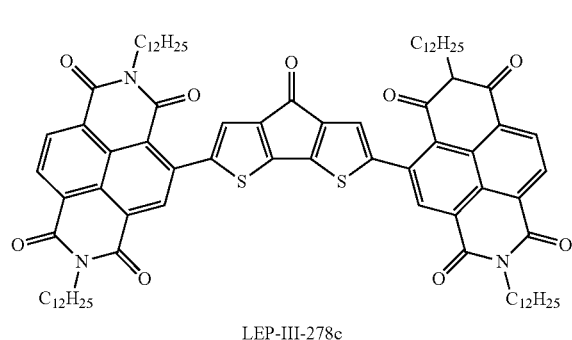

LEP-III-278c

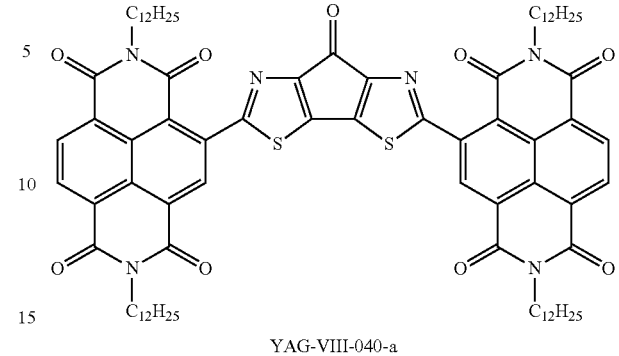

YAG-VIII-040-a

TABLE 6a

Summary of device data for NDI-based oligomers.

| No. | Compound | W/L | $C_{in}$ (nF/cm$^2$) | Solvent | S/D electrode | μ (cm$^2$/Vs) | $V_{TH}$ (V) | $I_{on/off}$ |
|---|---|---|---|---|---|---|---|---|
| 1 | LEP-III-1661 | 2550 μm/ 180 μm | 35.2 | Tetrachloroethane | Au | 0.17 ± 0.01 (Best: 0.19) | 11.5 ± 0.3 | 5 × 10$^3$ |
| 2 | YAG-VII-223-a | 2550 μm/ 180 μm | 35.2 | Tetrachloroethane | Au | 0.014 ± 0.003 (Best: 0.017) | 6.7 ± 0.8 | 10$^3$ |
| 3 | LEP-III-278c | 2550 μm/ 180 μm | 35.2 | Tetrachloroethane | Au | 0.086 ± 0.025 (Best: 0.112) | 12.5 ± 0.9 | 5 × 10$^3$ |
| 4 | YAG-VIII-040-a | | | Tetrachloroethane | Au | 0.046 ± 0.009 (Best: 0.063) | 9.1 ± 0.5 | 5 × 10$^3$ |
| 5 | YAG-IX-031-b | 2550 μm/ 180 μm | 35.2 | Tetrachloroethane (20 mg/ml) | Au/Ti | 0.059 ± 0.004 (Best: 0.067) | 7.3 ± 0.6 | 10$^4$ |

What is claimed is:

1. A bis(naphthalene diimide) compound or a mixture thereof having the structure:

wherein
a) hAr is a heteroaryl selected from:

wherein
i) "a" is an integer 1, 2, 3, or 4;
ii) each X and X' is independently selected from O, S, Se, or $NR^6$, wherein $R^6$ is a $C_1$-$C_{30}$ organic group independently selected from normal, branched, or cyclic alkyl, fluoroalkyl, aryl, heteroaryl, alkyl-aryl, and alkyl-heteroaryl groups optionally substituted with one or more fluoro, cyano, alkyl, alkoxy groups;
iii) each Y, Y', Y" and Y'" is independently selected from N, and $CR^7$, where $R^7$ is hydrogen, fluoro, or a $C_1$-$C_{30}$ organic group independently selected from cyano, normal, branched, or cyclic alkyl, perfluoroalkyl, alkoxy, perfluoroalkoxy, aryl, heteroaryl, alkyl-aryl, and alkyl-heteroaryl groups, optionally substituted with one or more fluoride, cyano, alkyl, alkoxy groups;
iv) each Z and Z' is independently selected from O, S, Se, $C(R^8)_2$, $Si(R^8)_2$, $NR^8$, (CO), $(CO)_2$ or $C=C(CN)_2$, wherein $R^8$ is a $C_1$-$C_{30}$ organic group independently selected from normal, branched, or cyclic alkyl, perfluoroalkyl, aryl, heteroaryl, alkyl-aryl, and alkyl-heteroaryl groups, optionally substituted with one or more fluoro, cyano, alkyl, alkoxy groups;

b) each $R^1$ and $R^{1'}$ is a $C_1$-$C_{30}$ organic group independently selected from a normal, branched, or cyclic alkyl, aryl, heteroaryl, alkyl-aryl, or alkyl-heteroaryl group optionally substituted with one or more halide, cyano, alkyl, or alkoxy groups;

c) $R^2$, $R^3$, and $R^4$ are independently selected from hydrogen, halide, or a $C_1$-$C_{30}$ organic group independently selected from cyano, normal, branched, or cyclic alkyl, fluoroalkyl, aryl, heteroaryl, alkyl-aryl, acyl- and alkyl-heteroaryl groups, optionally substituted with one or more fluoro, cyano, alkyl, alkoxy groups.

2. The compound of claim 1, wherein $R^1$, $R^{1'}$ is a $C_1$-$C_{30}$ normal, branched, or cyclic alkyl or fluoroalkyl group.

3. The compound of claim 1, wherein $R^2$, $R^3$, and $R^4$ are independently selected from hydrogen, fluoro and cyano.

4. The compound of claim 1, wherein hAr is a heteroaryl selected from:

5. The compound of claim 1, wherein hAr is a heteroaryl selected from:

6. The compound of claim 1, wherein X and X' are S.

7. The compound of claim 1, wherein Y, Y', Y" and Y'" are N or CH.

8. The compound of claim 1, wherein hAr has one of the structures:

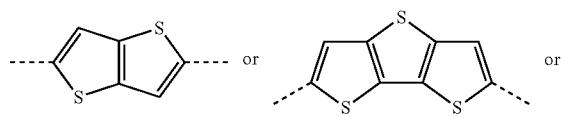

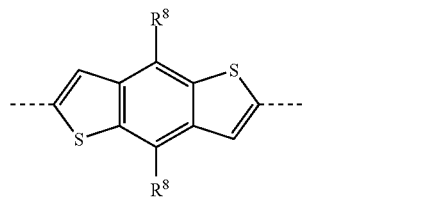

wherein R⁸ is hydrogen, cyano, or a $C_1$-$C_{12}$ normal, branched alkyl, perfluoroalkyl, alkoxy, or perfluoroalkoxy group;

or

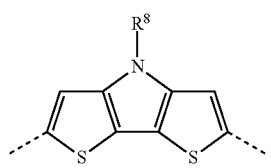

wherein R⁸ is a $C_1$-$C_{20}$ normal or branched, alkyl, perfluoroalkyl, aryl, heteroaryl, alkyl-aryl, and alkyl-heteroaryl group, optionally substituted with one or more fluoro, cyano, alkyl, alkoxy groups;

or

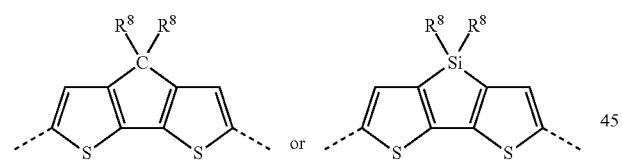

or wherein R⁸ is hydrogen, or a $C_1$-$C_{12}$ normal or branched alkyl or perfluoroalkyl group;

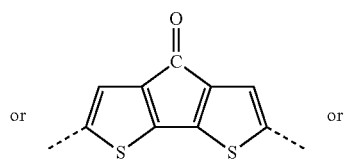 or

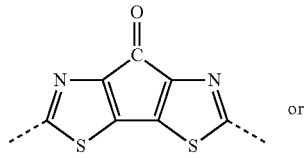 or

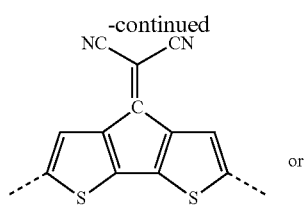 or

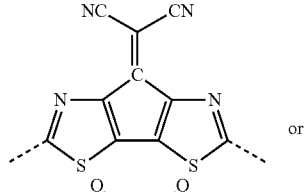 or

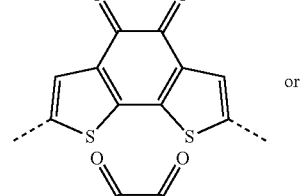 or

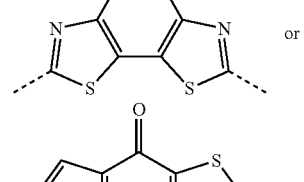 or

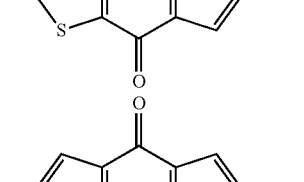 or

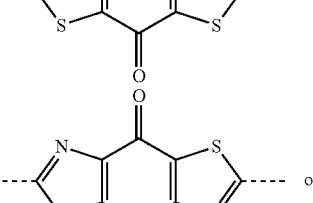 or

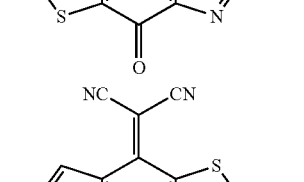 or

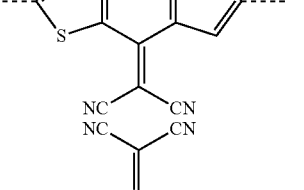 or

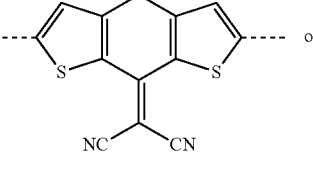 or

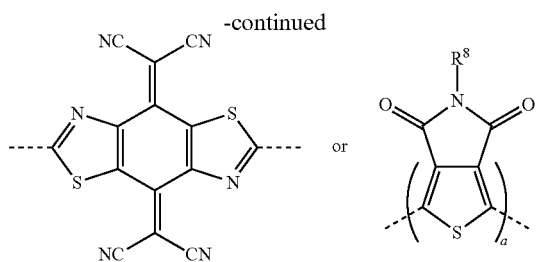

-continued or wherein $R^8$ is a $C_1$-$C_{20}$ normal or branched, alkyl or perfluoroalkyl group, wherein the alkyl group is optionally substituted with one or more fluoro, cyano, alkyl, alkoxy groups.

9. The compound of claim 1, wherein hAr has the structure:

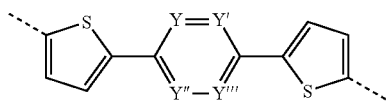

wherein Y, Y', Y" and Y'" are N or $CR^7$, and $R^7$ is hydrogen or a $C_1$-$C_{20}$ normal or branched, alkyl or perfluoroalkyl group, wherein the alkyl group is optionally substituted with one or more fluoro, cyano, alkyl, alkoxy groups.

10. An electronic device comprising one or more compounds according to claim 1.

11. The electronic device of claim 10, wherein the device is a transistor.

12. The electronic device of claim 11, wherein the transistor is a top gate-bottom contact transistor.

13. The electronic device of claim 12, wherein the top gate comprises an organic polymer dielectric layer in contact with the one or more compounds, and a high dielectric constant metal oxide dielectric layer in contact with the organic polymer dielectric layer.

14. The electronic device of claim 10, wherein the device is a complementary-like inverter.

15. A method for making the electronic device of claim 10, wherein the method of making comprises at least one step comprising depositing an organic semiconductor layer by inkjet printing.

16. The method according to claim 15, wherein the organic semiconducting layer is deposited on a flexible substrate by inkjet printing.

17. The compound of claim 1, wherein the bis(naphthalene diimide) compound has the structure

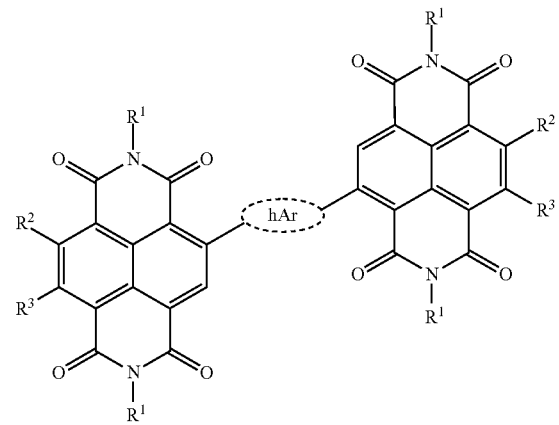

wherein $R^3$ is are independently selected from fluoro, cyano, and trifluoroalkyl group.

* * * * *